United States Patent
Rigo et al.

(10) Patent No.: US 12,013,403 B2
(45) Date of Patent: Jun. 18, 2024

(54) COMPOSITIONS AND METHODS FOR DETECTION OF SMN PROTEIN IN A SUBJECT AND TREATMENT OF A SUBJECT

(71) Applicant: Biogen MA Inc., Cambridge, MA (US)

(72) Inventors: Frank Rigo, Carlsbad, CA (US); Katherine M. Bishop, San Diego, CA (US)

(73) Assignee: BIOGEN MA INC., Cambridge, MA (US)

( * ) Notice: Subject to any disclaimer, the term of this patent is extended or adjusted under 35 U.S.C. 154(b) by 175 days.

(21) Appl. No.: 17/365,365

(22) Filed: Jul. 1, 2021

(65) Prior Publication Data

US 2021/0389335 A1 Dec. 16, 2021

Related U.S. Application Data

(60) Continuation of application No. 17/100,073, filed on Nov. 20, 2020, now abandoned, which is a continuation of application No. 16/829,760, filed on Mar. 25, 2020, now abandoned, which is a continuation of application No. 16/538,422, filed on Aug. 12, 2019, now abandoned, which is a division of application No. 15/509,642, filed as application No. PCT/US2015/049598 on Sep. 11, 2015, now Pat. No. 10,436,802.

(60) Provisional application No. 62/062,074, filed on Oct. 9, 2014, provisional application No. 62/049,983, filed on Sep. 12, 2014.

(51) Int. Cl.
*C07H 21/04* (2006.01)
*C12N 15/113* (2010.01)
*G01N 33/566* (2006.01)
*G01N 33/68* (2006.01)

(52) U.S. Cl.
CPC ....... *G01N 33/6896* (2013.01); *C12N 15/113* (2013.01); *G01N 33/566* (2013.01); *G01N 33/6854* (2013.01); *G01N 33/6887* (2013.01); *C12N 2310/11* (2013.01); *C12N 2310/315* (2013.01); *C12N 2310/322* (2013.01); *C12N 2310/3341* (2013.01); *C12N 2320/32* (2013.01); *C12N 2320/35* (2013.01); *G01N 2333/47* (2013.01); *G01N 2800/28* (2013.01); *G01N 2800/2878* (2013.01); *G01N 2800/52* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,751,219 A | 6/1988 | Kemoen et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Soielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,176,996 A | 1/1993 | Hogan et al. |
| 5,177,196 A | 1/1993 | Mever, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |

(Continued)

FOREIGN PATENT DOCUMENTS

| | | |
|---|---|---|
| CL | 2021001136 | 1/2022 |
| EP | 1910395 | 10/2012 |

(Continued)

OTHER PUBLICATIONS

PCT International Preliminary Report on Patentability in International Appln. No. PCT/US2020/042312, dated Feb. 3, 2022, 8 pages.
U.S. Appl. No. 16/837,349, filed Apr. 1, 2020, Rigo.
Ciafaloni et al., "Nusinersen for SMA," Neurology, 2019, 92(21):985-986.
European Search Report in European Application No. EP 22206076, dated Apr. 6, 2023, 12 pages.
Agrawal et al., "Modified oligonucleotides and therapeutic and diagnostic agents," Curr Opin Biotechn, 1995, 6:12-19.

(Continued)

*Primary Examiner* — Kimberly Chong
(74) *Attorney, Agent, or Firm* — McCarter & English LLP; Xin Zhang

(57) ABSTRACT

Disclosed herein are compounds, compositions and methods for modulating splicing of SMN2 mRNA in a subject. Also provided are uses of disclosed compounds and compositions in the manufacture of a medicament for treatment of diseases and disorders, including spinal muscular atrophy. Also provided are kits for detecting the amount of SMN protein in a sample of cerebrospinal fluid.

17 Claims, No Drawings
Specification includes a Sequence Listing.

(56) References Cited

U.S. PATENT DOCUMENTS

| | | |
|---|---|---|
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,294,564 A | 3/1994 | Karapiperis et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,627,274 A | 5/1997 | Kole et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Sunuuerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,811,534 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,172,216 B1 | 1/2001 | Bennett et al. |
| 6,210,892 B1 | 4/2001 | Bennett et al. |
| 6,214,986 B1 | 4/2001 | Bennett et al. |
| 6,268,490 B1 | 7/2001 | Imanishi et al. |
| 6,300,319 B1 | 10/2001 | Manoharau |
| 6,376,508 B1 | 4/2002 | Li et al. |
| 6,383,812 B1 | 5/2002 | Chen et al. |
| 6,426,220 B1 | 7/2002 | Bennett et al. |
| 6,525,031 B2 | 2/2003 | Manoharau et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,620,916 B1 | 9/2003 | Takahara et al. |
| 6,660,720 B2 | 12/2003 | Manoharan |
| 6,670,461 B1 | 12/2003 | Wengel et al. |
| 6,753,423 B1 | 6/2004 | Cook et al. |
| 6,770,633 B1 | 8/2004 | Robbins et al. |
| 6,770,748 B2 | 8/2004 | Imanishi et al. |
| 6,794,499 B2 | 9/2004 | Wengel et al. |
| 6,906,182 B2 | 6/2005 | Ts'o et al. |
| 6,908,903 B1 | 6/2005 | Theodore et al. |
| 6,962,906 B2 | 11/2005 | Efimov et al. |
| 6,998,259 B1 | 2/2006 | Davis et al. |
| 7,015,315 B1 | 3/2006 | Cook et al. |
| 7,034,009 B2 | 4/2006 | Pavco et al. |
| 7,034,133 B2 | 4/2006 | Wengel et al. |
| 7,053,207 B2 | 5/2006 | Wengel |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,572,582 B2 | 8/2009 | Wengel et al. |
| 7,582,744 B2 | 9/2009 | Manoharan et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,838,657 B2 | 11/2010 | Singh et al. |
| 7,851,615 B2 | 12/2010 | Manoharan et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,034,909 B2 | 10/2011 | Wengel et al. |
| 8,080,644 B2 | 12/2011 | Wengel et al. |
| 8,088,746 B2 | 1/2012 | Seth et al. |
| 8,088,904 B2 | 1/2012 | Swayze et al. |

(56) References Cited

U.S. PATENT DOCUMENTS

| | | |
|---|---|---|
| 8,106,022 B2 | 1/2012 | Manoharan et al. |
| 8,110,560 B2 | 2/2012 | Singh et al. |
| 8,124,745 B2 | 2/2012 | Allerson et al. |
| 8,137,695 B2 | 3/2012 | Rozema et al. |
| 8,153,365 B2 | 4/2012 | Wengel et al. |
| 8,158,601 B2 | 4/2012 | Chen et al. |
| 8,183,002 B2 | 5/2012 | Adamczyk et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,313,772 B2 | 11/2012 | Rozema et al. |
| 8,344,125 B2 | 1/2013 | Manoharan et al. |
| 8,349,308 B2 | 1/2013 | Yurkovetskiy et al. |
| 8,361,977 B2 | 1/2013 | Baker et al. |
| 8,394,932 B2 | 3/2013 | Melki et al. |
| 8,404,862 B2 | 3/2013 | Manoharan et al. |
| 8,435,491 B2 | 5/2013 | Wang et al. |
| 8,440,803 B2 | 5/2013 | Swayze et al. |
| 8,450,467 B2 | 5/2013 | Manoharan et al. |
| 8,501,805 B2 | 8/2013 | Seth et al. |
| 8,501,930 B2 | 8/2013 | Rozema et al. |
| 8,530,640 B2 | 9/2013 | Seth et al. |
| 8,541,548 B2 | 9/2013 | Rozema et al. |
| 8,546,556 B2 | 10/2013 | Seth et al. |
| 8,552,163 B2 | 10/2013 | Lee et al. |
| 8,586,559 B2 | 11/2013 | Singh et al. |
| 8,609,065 B2 | 12/2013 | Kuik-Romeijn et al. |
| RE44,779 E | 2/2014 | Imanishi et al. |
| 8,779,128 B2 | 7/2014 | Hanson et al. |
| 8,796,437 B2 | 8/2014 | Swayze et al. |
| 8,802,642 B2 | 8/2014 | Singh et al. |
| 8,828,956 B2 | 9/2014 | Manoharan et al. |
| 8,946,183 B2 | 2/2015 | Baker et al. |
| 8,962,269 B2 | 2/2015 | Melki et al. |
| 8,980,853 B2 | 3/2015 | Bennett et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,161,948 B2 | 10/2015 | Hanson et al. |
| 9,181,549 B2 | 11/2015 | Prakash et al. |
| 9,217,147 B2 | 12/2015 | Singh et al. |
| 9,290,760 B2 | 3/2016 | Rajeev et al. |
| 9,476,042 B2 | 10/2016 | Singh et al. |
| 9,518,259 B2 | 12/2016 | Rigo et al. |
| 9,717,750 B2 | 8/2017 | Bennett et al. |
| 9,765,338 B2 | 9/2017 | Bennett et al. |
| 9,862,946 B2 | 1/2018 | Hanson et al. |
| 9,926,559 B2 | 3/2018 | Bennett et al. |
| 10,059,941 B2 | 8/2018 | Krieg et al. |
| 10,174,328 B2 | 1/2019 | Krieg et al. |
| 10,266,822 B2 | 4/2019 | Singh et al. |
| 10,436,802 B2 | 10/2019 | Rigo et al. |
| 11,198,867 B2 | 12/2021 | Rigo et al. |
| 11,299,737 B1 | 4/2022 | Rigo |
| 11,525,848 B2 | 12/2022 | Rigo et al. |
| 2001/0049436 A1 | 12/2001 | Zhou |
| 2001/0053519 A1 | 12/2001 | Fodor et al. |
| 2003/0077829 A1 | 4/2003 | MacLachlan |
| 2003/0100505 A1 | 5/2003 | Scharschmidt et al. |
| 2003/0119724 A1 | 6/2003 | Ts'o et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2005/0130923 A1 | 6/2005 | Bhat et al. |
| 2005/0164235 A1 | 7/2005 | Manoharan et al. |
| 2005/0214288 A1 | 9/2005 | Bell et al. |
| 2006/0148740 A1 | 7/2006 | Platenburg |
| 2006/0183886 A1 | 8/2006 | Tso et al. |
| 2007/0031844 A1 | 2/2007 | Khvorova et al. |
| 2007/0292408 A1 | 12/2007 | Singh et al. |
| 2007/0299021 A1 | 12/2007 | Dunckley et al. |
| 2008/0039618 A1 | 2/2008 | Allerson et al. |
| 2008/0045456 A1 | 2/2008 | Greenway et al. |
| 2008/0064084 A1 | 3/2008 | Muller et al. |
| 2008/0108801 A1 | 5/2008 | Manoharan et al. |
| 2008/0206869 A1 | 8/2008 | Smith et al. |
| 2008/0281041 A1 | 11/2008 | Rozema et al. |
| 2008/0281044 A1 | 11/2008 | Monahan et al. |
| 2009/0203132 A1 | 8/2009 | Swayze et al. |
| 2009/0203135 A1 | 8/2009 | Forst et al. |
| 2009/0286973 A1 | 11/2009 | Manoharan et al. |
| 2010/0081627 A1 | 4/2010 | Sampath et al. |
| 2010/0087511 A1 | 4/2010 | Singh et al. |
| 2010/0190837 A1 | 7/2010 | Migawa et al. |
| 2010/0197762 A1 | 8/2010 | Swayze et al. |
| 2010/0216238 A1 | 8/2010 | Baker et al. |
| 2010/0240730 A1 | 9/2010 | Beigelman et al. |
| 2011/0097264 A1 | 4/2011 | Wang et al. |
| 2011/0097265 A1 | 4/2011 | Wang et al. |
| 2011/0123520 A1 | 5/2011 | Manoharan et al. |
| 2011/0207799 A1 | 8/2011 | Rozema et al. |
| 2011/0269814 A1 | 11/2011 | Manoharan et al. |
| 2011/0269820 A1 | 11/2011 | Singh et al. |
| 2011/0294868 A1 | 12/2011 | Mania et al. |
| 2012/0021515 A1 | 1/2012 | Swayze et al. |
| 2012/0035115 A1 | 2/2012 | Manoharan et al. |
| 2012/0059042 A1 | 3/2012 | Platenburg et al. |
| 2012/0087869 A1 | 4/2012 | Thakker et al. |
| 2012/0095075 A1 | 4/2012 | Manoharan et al. |
| 2012/0101148 A1 | 4/2012 | Akinc et al. |
| 2012/0128760 A1 | 5/2012 | Manoharan et al. |
| 2012/0136042 A1 | 5/2012 | Manoharan et al. |
| 2012/0149756 A1 | 6/2012 | Schumoerli et al. |
| 2012/0149757 A1 | 6/2012 | Krainer et al. |
| 2012/0157509 A1 | 6/2012 | Hadwiger et al. |
| 2012/0165393 A1 | 6/2012 | Rozema et al. |
| 2012/0165394 A1 | 6/2012 | Singh et al. |
| 2012/0190728 A1 | 7/2012 | Bennett et al. |
| 2012/0230938 A1 | 9/2012 | Rozema et al. |
| 2013/0004427 A1 | 1/2013 | El-Sayed et al. |
| 2013/0109091 A1 | 5/2013 | Baker et al. |
| 2013/0109817 A1 | 5/2013 | Yurkovetskiv et al. |
| 2013/0121954 A1 | 5/2013 | Wakefield et al. |
| 2013/0130378 A1 | 5/2013 | Manoharan et al. |
| 2013/0178512 A1 | 7/2013 | Manoharan et al. |
| 2013/0203836 A1 | 8/2013 | Rajeev et al. |
| 2013/0236968 A1 | 9/2013 | Manoharan et al. |
| 2013/0289092 A1 | 10/2013 | Rigo et al. |
| 2014/0107330 A1 | 4/2014 | Freier et al. |
| 2014/0113956 A1 | 4/2014 | Charbonnier et al. |
| 2014/0128449 A1 | 5/2014 | Liu et al. |
| 2014/0155363 A1 | 6/2014 | Marom et al. |
| 2014/0296323 A1 | 10/2014 | Leumauu et al. |
| 2014/0323552 A1 | 10/2014 | Burghes et al. |
| 2014/0329772 A1 | 11/2014 | Liusey et al. |
| 2014/0343127 A1 | 11/2014 | Kammler |
| 2014/0357558 A1 | 12/2014 | Hua et al. |
| 2014/0367278 A1 | 12/2014 | Zaworski et al. |
| 2015/0018540 A1 | 1/2015 | Prakash et al. |
| 2015/0073140 A1 | 3/2015 | Hanson et al. |
| 2015/0164901 A1 | 6/2015 | Rubin et al. |
| 2015/0184153 A1 | 7/2015 | Freier et al. |
| 2015/0191727 A1 | 7/2015 | Migawa et al. |
| 2015/0252364 A1 | 9/2015 | Krieg et al. |
| 2015/0267195 A1 | 9/2015 | Seth et al. |
| 2015/0275212 A1 | 10/2015 | Albaek et al. |
| 2015/0315582 A1 | 11/2015 | Singh et al. |
| 2015/0353929 A1 | 12/2015 | Baker et al. |
| 2016/0002627 A1 | 1/2016 | Bennett et al. |
| 2016/0068838 A1 | 3/2016 | Lorson et al. |
| 2016/0068845 A1 | 3/2016 | Isis et al. |
| 2016/0074474 A1 | 3/2016 | Genzyme Coro |
| 2017/0015995 A1 | 1/2017 | Bennett et al. |
| 2017/0037397 A1 | 2/2017 | Singh et al. |
| 2017/0044538 A1 | 2/2017 | Rigo et al. |
| 2017/0051277 A1 | 2/2017 | Wilton et al. |
| 2017/0088835 A1 | 3/2017 | Baker et al. |
| 2017/0363643 A1 | 12/2017 | Rigo et al. |
| 2018/0028554 A1 | 2/2018 | Theodora et al. |
| 2018/0273954 A1 | 9/2018 | Linsley et al. |
| 2018/0291376 A1 | 10/2018 | Baker et al. |
| 2018/0298384 A1 | 10/2018 | Krieg et al. |

(56) References Cited

U.S. PATENT DOCUMENTS

| | | |
|---|---|---|
| 2019/0030058 A1 | 1/2019 | Bennett et al. |
| 2019/0040384 A1 | 2/2019 | Bennett et al. |
| 2019/0211330 A1 | 7/2019 | Hua et al. |
| 2020/0181613 A1 | 6/2020 | Baker et al. |
| 2020/0376018 A1 | 12/2020 | Bennett et al. |
| 2021/0032624 A1 | 2/2021 | Rigo et al. |
| 2021/0315918 A1 | 10/2021 | Prakash et al. |
| 2022/0064638 A1 | 3/2022 | Rigo et al. |
| 2022/0073914 A1 | 3/2022 | Rigo et al. |
| 2022/0073930 A1 | 3/2022 | Nestorov et al. |
| 2022/0325282 A1 | 10/2022 | Loveday et al. |
| 2023/0183696 A1 | 6/2023 | Rigo et al. |

FOREIGN PATENT DOCUMENTS

| | | |
|---|---|---|
| EP | 2548560 | 6/2015 |
| EP | 3305302 | 4/2018 |
| EP | 3308788 | 4/2018 |
| JP | 2003063992 | 3/2003 |
| JP | 2004-344072 | 12/2004 |
| JP | 2016515123 | 5/2016 |
| JP | 6370860 | 3/2017 |
| JP | 2019525918 | 9/2019 |
| RU | 2385933 | 4/2010 |
| SG | 189598 | 5/2013 |
| WO | WO 1994/026887 | 11/1994 |
| WO | WO 1995/022980 | 8/1995 |
| WO | WO 1997020563 | 6/1997 |
| WO | WO 1997046098 | 12/1997 |
| WO | WO 1998013381 | 4/1998 |
| WO | WO 1999014226 | 3/1999 |
| WO | WO 2001/009311 | 2/2001 |
| WO | WO 2002/038738 | 5/2002 |
| WO | WO 2002043771 | 6/2002 |
| WO | WO 2002076455 | 10/2002 |
| WO | WO 2003037909 | 5/2003 |
| WO | WO 2004024757 | 3/2004 |
| WO | WO 2004101619 | 11/2004 |
| WO | WO 2004/113867 | 12/2004 |
| WO | WO 2004106356 | 12/2004 |
| WO | WO 2007/002390 | 1/2007 |
| WO | WO 2007089611 | 8/2007 |
| WO | WO 2007134181 | 11/2007 |
| WO | WO 2008098788 | 8/2008 |
| WO | WO 2008101157 | 8/2008 |
| WO | WO 2008157753 | 12/2008 |
| WO | WO 2009008725 | 1/2009 |
| WO | WO 2009068689 | 6/2009 |
| WO | WO 2009082607 | 7/2009 |
| WO | WO 2009/120700 | 10/2009 |
| WO | WO 2009126933 | 10/2009 |
| WO | WO 2009134487 | 11/2009 |
| WO | WO 2010054406 | 5/2010 |
| WO | WO 2010/091308 | 8/2010 |
| WO | WO 2010088537 | 8/2010 |
| WO | WO 2010/120820 | 10/2010 |
| WO | WO 2010/123594 | 10/2010 |
| WO | WO 2010115993 | 10/2010 |
| WO | WO 2010129709 | 11/2010 |
| WO | WO 2010/148249 | 12/2010 |
| WO | WO 2010144740 | 12/2010 |
| WO | WO 2010148013 | 12/2010 |
| WO | WO 2011/032109 | 3/2011 |
| WO | WO 2011038356 | 3/2011 |
| WO | WO 2011100131 | 8/2011 |
| WO | WO 2011120053 | 9/2011 |
| WO | WO 2011133876 | 10/2011 |
| WO | WO 2011/159836 | 12/2011 |
| WO | WO 2011150408 | 12/2011 |
| WO | WO 2011163121 | 12/2011 |
| WO | WO 2012012443 | 1/2012 |
| WO | WO 2012037254 | 3/2012 |
| WO | WO 2012058462 | 5/2012 |
| WO | WO 2012068187 | 5/2012 |
| WO | WO 2012083046 | 6/2012 |
| WO | WO 2012083185 | 6/2012 |
| WO | WO 2012089352 | 7/2012 |
| WO | WO 2012089602 | 7/2012 |
| WO | WO 2012138487 | 10/2012 |
| WO | WO 2012150960 | 11/2012 |
| WO | WO 2012/178146 | 12/2012 |
| WO | WO 2012177947 | 12/2012 |
| WO | WO 2013/009703 | 1/2013 |
| WO | WO 2013033230 | 3/2013 |
| WO | WO 2013053928 | 4/2013 |
| WO | WO 2013/068441 | 5/2013 |
| WO | WO 2013075035 | 5/2013 |
| WO | WO 2013082551 | 6/2013 |
| WO | WO 2013086207 | 6/2013 |
| WO | WO 2013119916 | 8/2013 |
| WO | WO 2013165816 | 11/2013 |
| WO | WO 2013166121 | 11/2013 |
| WO | WO 2013173638 | 11/2013 |
| WO | WO 2014059341 | 4/2014 |
| WO | WO 2014/110291 | 7/2014 |
| WO | WO 2014113540 | 7/2014 |
| WO | WO 2014169243 | 10/2014 |
| WO | WO 2014179620 | 11/2014 |
| WO | WO 2015014838 | 2/2015 |
| WO | WO 2015023941 | 2/2015 |
| WO | WO 2015035460 | 3/2015 |
| WO | WO 2015051283 | 4/2015 |
| WO | WO 2015106128 | 7/2015 |
| WO | WO 2015161170 | 10/2015 |
| WO | WO 2015193651 | 12/2015 |
| WO | WO 2016/040748 | 3/2016 |
| WO | WO 2016164896 | 10/2016 |
| WO | WO 2017/00594 | 1/2017 |
| WO | WO 2017040271 | 3/2017 |
| WO | WO 2017053995 | 3/2017 |
| WO | WO 2017075030 | 5/2017 |
| WO | WO 2017218454 | 12/2017 |
| WO | WO 2017218884 | 12/2017 |
| WO | WO 2017223258 | 12/2017 |
| WO | WO 2018/014041 | 1/2018 |
| WO | WO 2018007475 | 1/2018 |
| WO | WO 2018014042 | 1/2018 |
| WO | WO 2018014043 | 1/2018 |
| WO | WO 2018055577 | 3/2018 |
| WO | WO 2018150196 | 8/2018 |
| WO | WO 2018193428 | 10/2018 |
| WO | WO 2018215563 | 11/2018 |
| WO | WO 2019075357 | 4/2019 |
| WO | WO 2019084050 | 5/2019 |
| WO | WO 2019168558 | 9/2019 |
| WO | WO 2019169203 | 9/2019 |
| WO | WO 2021/016032 | 1/2021 |
| WO | WO 2021174019 | 9/2021 |
| WO | WO 2021174031 | 9/2021 |

OTHER PUBLICATIONS

Albæk al., "Analogues of a Locked Nucleic Acid with Three-Carbon 2',4'-Linkages: Synthesis by Ring-Closing Metathesis and Influence on Nucleic Acid Duplex Stability and Structure," J. Org. Chem., Sep. 2006, 71(20):7731-7740.

Avila et al., "Trichostatin A increases SMN expression and survival in a mouse model of spinal muscular atrophy," J. Clin. Inves., Mar. 2007, 117(3):659-671.

Bennett et al., "Antisense Oligonucleotides as a tool for gene functionalization and target validation," Biochimica et Bionhvsics Acta., Dec. 1999, 1489(1):19-30.

Biessen et al., "Novel hepatotrophic prodrugs of the antiviral nucleoside 9-(2-phosphonylmethoxyethyl)adenine with improved pharmacokinetics and antiviral activity" FASEB J., Sep. 2000, 14(12)1784-1792.

Biessen et al., "Synthesis of Cluster Galactosides with High Affinity for the Hepatic Asialoglycoprotein Receptor," J Med Chem., Apr. 1995, 38(9):1538-1546.

Biessen et al., "The Cholesterol Derivative of a Triantennary Galactoside with High Affinity for the Hepatic Asialoglycoprotein Receptor: a Potent Cholesterol Lowering Agent," J Med. Chem., 1995, 38(11):1846-1852.

(56) References Cited

OTHER PUBLICATIONS

Bosch-Marce et al., "Increased IGF-1 in muscle modulates the phenotype of severe SMA mice," Human Molecular Genetic, Feb. 2011, 20(9):1844-1853.
Braasch et al., "Novel Antisense and Peptide Nucleic Acid Strategies for Controlling Gene Expression," Biochemistry, Apr. 2002, 41(14):4503-4510.
Briese et al., "SMN, the product of the spinal muscular atrophy-determining gene, is expressed widely but selectively in the developing human forebrain," J Comp. Neurol., Jun. 2006, 497(5):808-816.
Chen et al., "Genetics of amyotrophic lateral sclerosis: an update," Molecular Neurodegeneration, Aug. 2013, 8:28.
Connolly et al., "Binding and Endocytosis of Cluster Glycosides by Rabbit Hepatocytes, " J Biol. Chem., Jan. 1982, 257(2):939-945.
Crooke et al., "Pharmacokinetic Properties of Several Novel Oligonucleotide Analogs in mice, " J. Pharmacol. Exp. Ther., May 1996, 277(2):923-937.
Crooke, "Antisense Drug Technology," Second Edition, CRC Press, 2008, Chapters 1-28.
Douglas et al., "Splicing therapy for neuromuscular disease," Mal. Cell Neurosci., Sep. 2013, 56:169-185.
Duff et al., "Intrabody Tissue-Specific Delivery of Antisense Conjugates in Animals: Ligand-Linker-Antisense Oligomer Conjugates," Methods Enzymol., 2000, 313:297-321.
D'Ydewalle et al., "The Antisense Transcript SMN-AS1 Regulates SMN Expression and Is a Novel Therapeutic Target for Spinal Muscular Atrophy," Neuron, Jan. 2017, 93(1):66-79.
D'Ydewalle et al., "The long non-coding RNA SMN-AS1 as therapeutic target for SMA," 2016, FightSMA 25th Anniversary Conference Presentation, 36 pages.
D'Ydewalle, "Possible functions of SMN-associated long non-coding RNAs," Johns Hopkins Medicine, Apr. 10, 2014, 40 pages.
D'Ydewalle, "LncRNA as therapeutic target for SMA," [online] Jan. 30, 2015, retrieved Aug. 11, 2015, by ISA/US, 2 pages.
Egli et al., "Synthesis, improved antisense activity and structural rationale for the divergent RNA affinities of 3'-fluoro hexitol nucleic acid (FHNA and Ara-FHNA) modified oligonucleotides," J. Am. Chem., Oct. 2011, 133(41):16642-16649.
European Extended Search Report in European Application No. 17814164.4, dated Jun. 5, 2020, 20 pages.
European Extended Search Report in European Application No. 17828627.4, dated Feb. 18, 2020, 8 pages.
European Partial Search Report in European Application No. 17814164.4, dated Jan. 23, 2020, 18 pages.
European Partial Search Report in European Application No. 17828626.6, dated Feb. 17, 2020, 16 pages.
European Search Report in European Application No. 22195398, dated Mar. 1, 2023, 8 pages.
Freier et al., "The ups and downs of nucleic acid duplex stability: structure-stability studies on chemically modified DNA:RNA duplexes," Nucleic Acids Research, Nov. 1997, 25(22):4429-4443.
Frieden et al., "Expanding the design horizon of antisense oligonucleotides with alpha-L-LNA," Nucleic Acids Research, Nov. 2003, 31(21):6365-6372.
Gautsch et al., "Activity of a Novel bcl-2/bcl-xL-Bispecific Antisense Oligonucleotide Against Tumors of Diverse Histologic Origins," J. Natl. Cancer Inst., Mar. 2001, 93(6):463-471.
Gen bank Accession No. NT 006713.14, "*Homo sapiens* chromosome 5 genomic contig, reference assembly," truncated from nucleotides 19939708 to 19967777, Feb. 29, 2008, 4 pages.
Genbank Accession No. BC045789 .1, "*Homo sapiens* cDNA clone IMAGE:4796324," Jul. 21, 2005, 2 pages.
Hao et al., "Generation and Characterization of a genetic zebrafish model of SMA carrying the human SMN2 gene," Mol. Neurodegeneration, Mar. 2011, 6(24):1-9.
Haynes et al., "Proleme Analysis: Biological Assay or Data Archive?," Electrophoresis, Aug. 1998, 19(11):1862-1871.
Hsieh-Li et al., "A mouse model for spinal muscular atrophy," Nature Genet., Jan. 2000, 24(1):66-70.
Inclan et al., "Review of nine cases of chronic progressive muscular atrophy treated with growth hormone by the endoarterial route," Medicina., 1958) 26(2):347-351, 1 page.
International Search Report and Written Opinion in International Application No. PCT/US2015/026326, dated Nov. 3, 2015, 10 pages.
International Search Report and Written Opinion in International Application No. PCT/US2016/026928, dated Sep. 27, 2016, 15 pages.
International Search Report and Written Opinion in International Application No. PCT/US2017/037862, dated Oct. 20, 2017, 12 pages.
International Search Report and Written Opinion in International Application No. PCT/US2017/042463, dated Nov. 27, 2017, 12 pages.
International Search Report and Written Opinion in International Application No. PCT/US2017/042465, dated Oct. 12, 2017 , 11 pages.
International Search Report and Written Opinion in International Application No. PCT/US2021/019934, dated Aug. 13, 2021, 12 pages.
Jayaprakash et al., "Non-Nucleoside Building Blocks for Copper-Assisted and Copper-Free Click Chemistry for the Efficient Synthesis of RNA Conjugates," Org. Lett., Dec. 2010, 12(23):5410-5413.
Kabanov et al., "A new class of antivirals: antisense oligonucleotides combined with a hydrophobic substituent effectively inhibit influenza vims reproduction and synthesis of virus-specific proteins in MDCK cells," FEBS Lett., Jan. 1990, 259(2):327-330.
Kato et al., "N-acetylgalactosamine incorporation into a peptide containing consecutive threonine residues by UDP-N-acetyl-D-galactosaminide:Polypetide N-acetylgalactosaminyltransferases," Glycobiol, Oct. 2001, 11(10):821-829.
Kempf et al., "The transforming growth factor-ß superfamily member growth- differentiation factor-15 protects the heart from ischemia/reperfusion injury," Circulation Research, Feb. 2006, 98(3):351-360.
Khorev et al., "Trivalent, Gal/GalNAc-containing ligands designed for the asialoglycoprotein receptor" Bioorg. Med. Chem., May 2008, 16(9):5216-5231.
Kim et al., "Oligomeric Glycopeptidomimetics Bearing the Cancer Related TN-Antigen, " Tetrahedron Lett., May 1997, 38(20):3487-3490.
Kornilova et al., "Development of a fluorescence polarization binding assay for asialoglycoprotein receptor," Analyt Biochem., Jun. 2012, 425(1):43-46.
Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition," Tetrahedron, Apr. 1998, 54(14):3607-3630.
Kramer et al., "Raise the Roof: Boosting the Efficacy of a Spinal Muscular Atrophy Therapy," Neuron, Jan. 2017, 93(1): 3-5.
Kumar et al., "Design, synthesis, biophysical and primer extension studies of novel acyclic butyl nucleic acid (BuNA)," Org. Biomol. Chem., Sep. 2013, 11(35):5853-5865.
Kumar et al., "The First Analogues ofLNA (Locked Nucleic Acids): Phosphorothioate-LNA and 2'-thio-LNA," Bioorg. Med. Chem. Lett., Aug. 1998, 8(16):2219-2222.
Lee et al., "Facile Synthesis of a High-Affinity Ligand for Mammalian Hepatic Lectin Containing Three Terminal N-Acetylgalactosamine Residues," Bioconjug. Chem., Sep. 1997, 8:762-765.
Lee et al., "New and more efficient multivalent glyco-ligands for asialoglycoprotein receptor of mammalian hepatocytes," Bioorg. Med. Chem., Apr. 2011, 19(8):2494-2500.
Lee et al., "New Synthetic Cluster Ligands for Galactose/N-Acetylgalactosamine-Specific Lectin of Mammalian Liver," Biochem., Aug. 1984, 23(18):4255-4261.
Lee et al., "Preparation of Cluster Glycosides ofN-Acetylgalactosamine that have Subnanomolar Binding Constants Towards the Mammalian Hepatic Gal/GalNAc-specific Receptor," Glycoconiuzate J., Dec. 1987, 4:317-328.

(56) References Cited

OTHER PUBLICATIONS

Lee et al., "Protein microarrays to study carbohydrate-recognition events," Bioorg. Med. Chem. Lett., Oct. 2006, 16(19):5132-5135.

Lee et al., "Synthesis of Multivalent Neoglycoconjugates of MU C1 by the Conjugation of Carbohydrate-Centered, Triazole-Linked Glvcoclusters to MUC1 Peptides Using Click Chemistry," J. Org. Chem., Aug. 2012, 77(17):7564-7571.

Lee et al., "Synthesis of Peptide-Based Trivalent Scaffold for Preparation of Cluster Glycosides," Methods Enzymol., 2003, 362:38-43.

Lee, "Synthesis of some cluster glycosides suitable for attachment to proteins or solid matrices," Carbohydr. Res., Dec. 1978, 67:509-514.

Letsinger et al., "Cholesteryl-conjugated oligonucleotides: Synthesis, properties, and activity as inhibitors of replication of human immunodeficiency vims in cell culture," Proc. Natl. Acad. Sci. USA, Sep. 1989, 86(17):6553-6556.

Leumann, "DNA Analogues: From Supramolecular Principles to Biological Properties, " Bioorg. & Med. Chem., Apr. 2002, 10(4):841-854.

Maher et al., "Comparative hybrid arrest by tandem antisense oligodeoxyribonucleotides or oligodeoxyribonucleoside methylpbosphonates in a cell-free system," Nucl. Acid. Res., Apr. 1988, 16(8):3341-3358.

Maier et al., "Synthesis of Antisense Oligonucleotides Conjugated to a Multivalent Carbohydrate Cluster for Cellular Targeting," Bioconjugate Chem., Dec. 2003, 14(1):18-29.

Maierhofer et al., "Probing multivalent carbohydrate-lectin interactions by an enzyme-linked lectin assay employing covalently immobilized carbohydrates," Bioorg. Med. Chem., Dec. 2007, 15(24):7661-7676.

Manoharan et al., "Chemical Modifications to Improve Uptake and Bioavailability of Antisense Oligonucleotides, " Ann. N.Y. Acad. Sci., Oct. 1992, 660:306-309.

Manoharan et al., "Cholic Acid-Oligonucleotide Conjugates for Antisense Applications, " Bioorg. Med. Chem. Lett., Apr. 1994, 4(8):1053-1060.

Manoharan et al., "Introduction of a Lipophilic Thioether Tether in the Minor Groove of Nucleic Acids for Antisense Applications," Bioorg Med. Chem. Lett., Dec. 1993, 3(12):2765-2770.

Manoharan et al., "Lipidic Nucleic Acids," Tetrahedron Lett., May 1995, 36(21):3651-3654.

Manoharan et al., "Oligonucleotide Conjugates: Alteration of the Pharmacokinetic Properties of Antisense Agents," Nucleosides & Nucleotides, Feb. 1995, 14(3-5):969-973.

Manoharan, "Oligonucleotide Conjugates as Potential Antisense Drugs with Improved Uptake, Biodistribution, Targeted Delivery, and Mechanism of Action," Antisense Nucleic Acid Drug Dev., Apr. 2002, 12(2):103-128.

Mattis et al., "Detection of human survival motor neuron (SMN) protein in mice containing the SMN2 transgene: applicability to preclinical therapy development for spinal muscular atrophy," J. Neurosci. Methods, Oct. 2008, 175(1):36-43.

Mattis et al., "Subcutaneous administration of TC007 reduces disease severity in an animal model of SMA," BioMed Central Neuroscience, Nov. 2009, 10: 1-6.

Merwin et al., "Targeted Delivery of DNA Using YEE(GalNAcAH)3, a Synthetic Glycopeptide Ligand for the Asialoglycoprotein Receptor," Bioconjugate Chem., 1994, 5:612-620.

Mishra et al., "Improved leishmanicidal effect of phosphorotioate antisense oligonucleotides by LDL-mediated delivery," Biochim. Biophys. Acta., 1995, 1264:229-237.

Ngo et al., "Computational Complexity, Protein Structure Predication and the Levinthal Paradox," The Protein Folding Problem and Tertiary Structure Prediction, 1994, 433-440 and 492-495, 12 pages.

Nishina et al., "Chimeric Antisense Oligonucleotide Conjugated to a-Tocopherol," Molecular Therapy Nucleic Acids, 2015, 4(e220):1-10.

Nishina et al., "Efficient In Vivo Delivery of siRNA to the Liver by Conjugation of α-Tocopherol," Molecular Therapy ,2008, 16, 734-740.

Oberhauser et al., "Effective incorporation of 2'-O-methyl-oligonucleotides into liposomes and enhanced cell association through modification with thiocholesterol," Nucl. Acids Res., 1992, 20(3):533-538.

Ogino et al., "New insights on the evolution of the SMN1 and SMN2 region: simulation and meta-analysis for allele and haplotype frequency calculations," Eur. J. Human Genetics, 2004, 12:1015-1023.

Ozaki et al., "Synthesis and Properties of Oligodeoxyribonucleotides Bearing a Ploy amino Group at the 2' Position via 2'-O-Carbamoylmethyl and 2'-S-Carbamoylmethyl groups" Nucleosides, Nucleotides, and Nucleic Acids, 2009, 28(10):943-952.

Pattanayek et al., "Structural rationalization of a large difference in RNA affinity despite a small difference in chemistry between two 2'-O-modified nucleic acid analogues," J Am Chem. Soc, 2004, 126:15006-15007.

Pavia et al., "Synthetic TN glycopeptide related to human glycophorin AM" Int J Pep Protein Res., 1983, 22:539-548.

Pei et al., "Guided genetic screen to identify genes essential in the regeneration of hair cells and other tissues," NPJ Regenerative Medicine, 2018, 11:1-11.

Prakash et al., "2'-O-[2-(Amino)-2-oxoethyl] Oligonucleotides," Org. Lett., 2003, 5, 403-6.

Prakash et al., "An overview of sugar-modified oligonucleotides for antisense therapeutics," Chem Biodivers, 2011, 8:1616-1641.

Prakash et al., "Comparing In Vitro and In Vivo Activity of2'-O-[2-(Methylamino)-2-oxoethyl]-and 2'-0-Methoxvethvl-Modified Antisense Oligonucleotides" J. Med. Chem., 2008, 51:2766-2776.

Pujol et al., "A Sulfur Tripod Glycoconjugate that Releases a High-Affinity Copper Chelator in Hepatocytes," Angew. Chemie. Int. Ed. Engl., 2012, 51:7445-7448.

Rajur et al., "Covalent Protein-Oligonucleotide Conjugates for Efficient Delivery of Antisense Molecules," Bioconjug. Chem., 1997, 8:935-940.

Ramos et al., "Age-dependent SMN expression in disease-relevant tissue and implications for SMA treatment," J. Clin. Invest., 2019, 129:4817-4831.

Rensen et al., "Design and Synthesis of Novel N-Acetylgalactosamine-Terminated Glycolipids for Targeting of Lipoproteins to the Hepatic Asialoglycoprotein Receptor," J. Med. Chem., 2004, 47:5798-5808.

Rensen et al., "Determination of the Upper Size Limit for Uptake and Processing of Ligands by the Asialoglycoprotein Receptor on Hepatocytes in Vitro and in Vivo," J. Biol. Chem., 2001, 276:37577-37584.

Rensen et al., "Stimulation of Liver-Directed Cholesterol Flux in Mice by Novel N-Acetylgalactosamine-Terminated Glycolipids with High Affinity for the Asialoglycoprotein Receptor," Arterioscler. Thromb. Vase. Biol., 2006, 26:169-175.

Riessland et al., "SAHA ameliorates the SMA phenotype in two mouse models for spinal muscular atrophy," Human Molecular Genetics, 2010, 19(8):1492-1506.

Rochette et al., "SMN gene duplication and the emergence of the SMN2 gene occurred in distinct hominids: SMN2 is unique to *Homo sapiens*," Hum. Genet., 2001, 108:255-266.

Saison-Behmoaras et al., "Short modified antisense oligonucleotides directed against Ha-ras point mutation induce selective cleavage of the mRNA and inhibit T24 cells proliferation, " EMBO J., 1991, 10:1111-1118.

Sato et al., "Glycoinsulins: Dendritic Sialyloligosaccharide-Displaying Insulins Showing a Prolonged Blood-Sugar-Lowering Activity," J. Am. Chem. Soc., 2004, 126:14013-14022.

Seth et al., "Short Antisense Oligonucleotides with Novel 2'-4' Conformationaly Restricted Nucleoside Analogues Show Improved Potency Without Increased Toxicity in Animals, " J. Med. Chem., 2009, 52:10-13.

Shea et al., "Synthesis, hybridization properties and antiviral activity of lipid-oligodeoxynucleotide conjugates, " Nucl. Acids Res., 1990, 18:3777-3783.

(56) References Cited

OTHER PUBLICATIONS

Sheng et al., "Comparison of the efficacy of MOE and PMO modifications of systemic antisense oligonucleolides in a severe SMA mouse model," Nucleic Acids Res, 2020, 48:2853-2865.
Singh et al., "LNA (locked nucleic acids): synthesis and high-affinity nucleic acid recognition," Chem. Commun., 1998, 4:455-456.
Singh et al., "Synthesis of 2'-Amino-LNA: A Novel Conformationally Restricted High-Affinity Oligonucleotide Analogue with a Handle," J. Org. Chem., 1998, 63:10035-10039.
Skolnick et al., "From genes to protein structure and function: novel Applications of computational approaches in the genomic era," Trends in Biotech., 2000, 18:34-39.
Sliedregt et al., "Design and Synthesis of Novel Amphiphilic Dendritic Galactosides for Selective Targeting of Liposomes to Hepatic Asialoglycoprotein Receptor," J. Med. Chem., 1999, 42:609-618.
Spicer et al., "The altered expression of neurofilament in mouse models and patients with spinal muscular atrophy," Annals of Clinical and Translational Neurology, 2021, 8(4):866-876.
Srivastava et al., "Five- and Six-Membered Conformationally Locked 2', 4'-Carbocyclic ribo-Thymidines: Synthesis, Structure, and Biochemical Studies," J Am. Chem. Soc., 2007, 129:8362-8379.
Svinarchuk et al., "Inhibition of HIV proliferation in MT-4 cells by antisense oligonucleotide conjugated to lipophilic groups," Biochimie., 1993, 75:49-54.
Tokuriki et al., "Stability effects of mutations and protein evolvability," Current Opinion in Structural Biology, 2009, 19:596-604.
Tomiya et al., "Liver-targeting of primaquine-( poly-γ-glutamic acid) and its degradation in rat hepatocytes," Bioorg. Med. Chem., 2013, 21:5275-5281.
Toyokuni et al., "Synthetic Vaccines: I. Synthesis of Multivalent Tn Antigen Cluster-Lysyllysine Conjugates," Tetrahedron Lett., 1990, 31:2673-2676.
Valentijn et al., "Solid-phase Synthesis of Lysine-Based Cluster Galactosides with High Affinity for the Asialoglycoprotein Receptor," Tetrahedron, 1997, 53:759-770.
Van Rossenberg et al., "Stable polyplexes based on arginine-containing oligopeptides for in vivo gene delivery" Gene Ther., 2004, 11:457-464.
Veldink et al., "SMN genotypes producing less SMN protein increase susceptibility to and severity of sporadic ALS," Neurology, 2005, 65(6):820-825.
Wahlestedt et al., "Potent and nontoxic antisense oligonucleotides containing locked nucleic acids, " PNAS, 2000, 97(10):5633-5638.
Westerlind et al., "Ligands of the asialoglycoprotein receptor for targeted gene delivery, part 1: Synthesis of and binding studies with biotinylated cluster glycosides containing N-acetylgalactosamine," Glycoconj. J., 2004, 21:227-241.
Wilcox et al., "Immobilization and Utilization of the Recombinant Fusion Proteins Trypsin—Streptavidin and Streptavidin—Transglutaminase for Modification of Whey Protein Isolate Functionality," Journal of agricultural and food chemistry, 2002, 50(13):3723-3730.
Woo et al., "Gene activation of SMN by selective disruption of lncRNA-mediated recruitment of PRC2 for the treatment of spinal muscular atrophy," PNAS USA, 2017, 114:E1509-E1518.
Woolf et al., "Specificity of antisense oligonucleotides in vivo," PNAS, 1992, 89:7305-7309.
Yamamoto et al., "Antisense drug discovery and development," Future Med. Chem., 2011, 3:339-365.
Zhou et al., "Fine Tuning of Electrostatics around the Intenucleotidic Phosphate through Incorporation of Modified 2',4'-Carbocyclic-LNAs and-ENAs Leads to Significant Modulation of Antisense Properties," J. Org. Chem., 2009, 74:118-134.
Zhou et al., "Targeting RNA-splicing for SMA Treatment," Molecules and Cells, 2012, 33:223-228.
U.S. Appl. No. 17/991,995, filed Nov. 22, 2022, Rigo.
EMA.europa.eu [online], "Annex I, Technical Sheet or Summary of Product Features—Spinraza, INN-nusinersen", 2022, retrieved on Sep. 6, 2022, retrieved from URL <https://www.ema.europa.eu/en/documents/product-information/spinraza-epar-product-information_en.pdf>, 31 pages.
Martinez-Hernandez et al., "Synaptic defects in type I spinal muscular atrophy in human development," J. Pathol., Jan. 2013, 229(1):49-61.
Ncbi.nlm.nih,gov [online], "Spinal Muscular Atrophy," Feb. 24, 2000, Updated Dec. 3, 2020, retrieved on Sep. 6, 2022, retrieved from URL <https://www.ncbi.nlm.nih.gov/books/NBK1352/>, 36 pages.
Wikimedia.org [online], "Nusinersen Sodium Colored," Mar. 2017, retrieved on Sep. 6, 2022, retrieved from URL <https://commons.wikimedia.org/w/index.php?curid=57063945>, 4 pages.
U.S. Appl. No. 15/931,887, filed May 14, 2020, Benentt.
U.S. Appl. No. 61/168,885, filed Apr. 13, 2008, Hua et al.
U.S. Appl. No. 61/218,031, filed Jun. 17, 2009, Bennett et al.
Batrakova et al., "Mechanism of Plutonic Effect on P-Glycoprotein Efflux System in Blood-Brain Barrier: Contributions of Energy Depletion and Membrane Fluidization" The Journal of Pharmacology and Experimental Therapeutics (2001) 299(2):483-493.
Baughan et al., "Delivery of bifunctional RNAs that target an intronic repressor and increase SMN levels in an animal model of spinal muscular atrophy" Human Molecular Genetics (2009) 18(9): 1600-1611.
Branch et al., "A good antisense molecule is hard to find," TIBS (1998) 23:45-50.
Brichta et al., "Valproic acid increases the SMN2 protein level: a well-known drug as a potential therapy for spinal muscular atrophy" Human Molecular Genetics (2003) 12(19):2481-2489.
Cartegni et al., "Correction of disease-associated exon skipping by synthetic exon-specific activators" Nat. Struct. Biol. (2003) 10:120-125.
Cartegni et al., "Disruption of an SF2/ASF-dependent exonic splicing enhancer in SMN2 causes spinal muscular atrophy in the absence of SMN1," Nat. Genet. 30:377-384 (2002).
Cartegni et al., "Listening to silence and understanding nonsense: exonic mutations that affect splicing," Nat. Rev. Genet. 3:285-298 (2002).
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Chinese Office Action in Chinese Patent Application No. 201710003678.9, dated Jan. 29, 2019, 23 pages (with English Translation).
Cifuentes-Diaz et al., "Neurofilament Accumulation at the Motor Endplate and Lack of Axonal Sprouting in a Spinal Muscular Atrophy Mouse Model" Human Molecular Genetics, Jun. 2002, 11(12):1439-1447.
Coady et al., "Development of a single vector system that enhances trans-splicing of SMN2 transcripts," PLoS ONE :(10):e3468 (2008).
Crooke et al., "Basic Principles of Antisense Therapeutics" Antisense Research and Application (1998) Chapter 1:1-50.
Crooke, "Antisense strategies" Cut. Mol. Med. (2004) 4(5):465-487.
Davis et al., "Potent inhibition of microRNA in vivo without degradation", Nucleic Acids Research, (2009) 37(1):71-77.
Derendorf et al., "Modeling of Pharmacokinetic/Pharmacodynamic (PK/PD) Relationships: Concepts and Perspectives", Pharmaceutical Research, Feb. 1999, 16(2):176-185.
Dokka et al., "Novel non-endocyte delively of antisense oligonucleotides" Advanced Drug Delivery Reviews (2000) 44:35-49.
Dominski et al., "Restoration of correct splicing in thalassemic pre-mRNA by antisense oligonucleotides" PNAS (1993) 90:8673-8677.
Dunckley et al., "Modification of splicing in the dystrophin gene in cultured mdx muscle cells by antisense oligoribonucleotides" Human Mol. Genetics (1998) 7(7):1083-1090.
Dunckley et al., "Modulation of Splicing in the DMD Gene by Antisense Oligoribonucleotides" Nucleosides & Nucleotides (1997) 16(7-9):1665-1668.
Efimov et al., "Phosphono Peptide Nucleic Acids with a Constrained Hydroxproline-Based Backbone" Nucleosides, Nucleotides & Nucleic Acids (2003) 22(5-8):593-599.

(56) References Cited

OTHER PUBLICATIONS

EP Notice of Opposition in European Application No. 17203901 3.3, dated Jun. 19, 2019, 19 pages.
European Extended Search Report in EP Appln. No. 20192937.9, dated Feb. 19, 2021, 7 pages.
European Search Report for application EP 06773838 dated Aug. 11, 2010, 7 pages.
European Search Report for application EP 10790221 dated Sep. 4, 2013, 12 pages.
European Search Report for application EP 14737605 dated Jun. 10, 2016, 8 pages.
European Search Report for application EP 2943225 dated Jun. 10, 2016, 9 pages.
European Search Report for European Application No. 15780586.2, dated Oct. 26, 2017, 8 pages.
European Search Report for European Application No. 17151519.0, dated Jul. 18, 2017, 5 pages.
European Search Report for European Application No. 18185820.0, dated Jan. 4, 2019, 11 pages.
European Search Report for European Application No. 18192730.2, dated Feb. 2, 2019, 7 pages.
European Search Report in EP Appln. No. 20192937.9, dated Feb. 19, 2021, 7 pages.
Extract from Remington: The Science and Practice of Pharmacy, 19th Edition (1995), 6 pages.
Finkel et al., "Nusinersen Versus Sham Control in Infantile-Onset Spinal Muscular Atrophy", New England Journal of Medicine, Nov. 2017, 377(18):1723-1732.
Finkel et al., "Treatment of Infantile-Onset Spinal Muscular Atrophy with Nusinersen: A Phase 2, Open-Label, Dose-Escalation Study", The Lancet, Dec. 7, 2016, 388(10063):3017-3026.
Forte et al., "Small interfering RNAs and Antisense Oligonucleotides for Treatment of Neurological Diseases" Current Drug Targets (2005) 6:21-29.
Friedman et al., "Correction of Aberrant Splicing of the Cystic Fibrosis Transmembrane Conductance Regulator (CFTR) Gene by Antisense Oligonucleotides" J. Biol. Chem. (1999) 274:36193-36199.
Gravrilina et al., "Neuronal SMN expression corrects spinal muscular atrophy in severe SMA mice while muscle-specific SMN expression has no phenotypic effect," Hum Mol Genet., 17(8):1063-1075 (2008).
Heasman, "Morpholino Oligos: Making Sense of Antisense?" Developmental Biology (2002) 243:209-214.
Hofmann et al., "Htra2-betal stimulates an exonic splicing enhancer and can restore full-length SMN expression to survival motor neuron 2 (SMN2)" PNAS (2000) 97(17):9618-9623.
Hua et al., "Antisense correction of SMN2 splicing in the CNS rescues necrosis in a type III SMA mouse model" Genes Dev. (2010) 24: 1634-1644.
Hua et al., "Antisense masking of an hnRNP A1/A2 inronic splicing silencer corrects SMN2 splicing in transgenic mice" American Journal of Human Genetics (2008) 82(4):834-848.
Hua et al., "Enhancement of SMN2 exon 7 inclusion by antisense oligonucleotides targeting the exon" PLOS Biology (2007) 5(4):E73.
Hua et al., "Peripheral SMN restoration in essential for long-term rescue of a severe spinal muscular atrophy mouse model," Nature, 478:123-26 (2011).
International Search Report and Written Opinion for application PCT/US2015/026326 dated Nov. 3, 2015, 10 pages.
International Search Report and Written Opinion for application PCT/US2015/049598 dated Jan. 19, 2016, 10 pages.
Ittig et al., "Nuclear antisense effects in cyclophilin A pre-rnRNA splicing by oligonucleotides: a comparison of tricyclo-DNA with LNA" Nucleic Acids Research (2004) 32(10:346-353.
Jaeger et al., "Transport of Antisense Across the Blood-Brain Barner" Methods in Molecular Medicine (2005) vol. 106: Antisense Therapeutics, Second Edition, I. Phillips (Ed.) Humana Press, Inc. Totowa, N.J., Cht. 12:237-251.

Kashima et al., "A negative element in SMN2 exon 7 inhibits splicing in spinal muscular atrophy." Nature Genetics (2003) 34(4):460-463.
Khoo and Krainer, "Splicing Therapeutics in SMN2 and APOB", Curr Opin Mol Therapy, 2009: 11(2): 108-115.
Király et al., "Expression of human cationic trypsinogen with an authentic N terminus using intein-mediated splicing in aminopeptidase P deficient *Escherichia coli*," Protein expression and purification, 2006, 48(1)104-111.
Kobayashi et al., "Evaluation of peripheral blood mononuclear cell processing and analysis for Survival Motor Neuron protein," PLoS One, 2012, 7(11):e50763.
Kobayashi et al., "Utility of Survival Motor Neuron ELISA for Spinal Muscular Atrophy Clinical and Preclinical Analyses," PLoS ONE 6:e24269 pp. 1-15 (2011).
Kole et al., "RNA modulation, repair and remodeling by splice switching oligonucleotides" Acta Biochemical Polonica (2004) 51(2):373-378.
Kole, "Modification of pre-mRNA splicing by antisense oligonucleotides" Acta Biochemical Polonica (1997) 44(2):231-238.
Koller et al., "Use of a Chemically Modified Antisense Oligunucleotide Library to Identify and Validate Eg5 (Kinesin-Like 1) as a Target for Antineoplastic Drug Development", Cancer Research, (2006) 66(4):2059-2066.
Krawczak et al., "The mutational spectrum of single base-pair substitutions in mRNA splice junctions of human genes: causes and consequences," Hum. Genet. 90:41-54 (1992).
Kurreck, "Antisense Technologies Improvement Through Novel Chemical Modifications" European Journal of Biochemistry (2003) 270(8):1628-1644.
Lacerra et al., "Restoration of hemoglobin A synthesis in erythroid cells from peripheral blood of thalassemic patients" PNAS (2000) 97(17):9591-9596.
Le et al., "SMNdelta7, the major product of the centromeric survival motor neuron (SMN2) gene, extends survival in mice with spinal muscular atrophy and associates with full-length SMN" Human Molecular Genetics (2005) 14(6):845-857.
Lefebvre et al., "The Role of the SMN Gene in Proximal Spinal Muscular Atrophy" Hum. Mol. Genet. (1998) 7(10):1531-1536.
Lim et al., "Modulation of Survival Motor Neuron Pre-mRNA Splicing by Inhibition of Alternative 3'Splice Site Pairing" J. Biol. Chem. (2001) 276(48):45476-45483.
Lorson et al., "A single nucleotide in the SMN gene regulates splicing and is responsible for spinal muscular atrophy" PNAS (1999) 96:6307-6311.
Lu et al., "Systemic delivery of antisense oligoribonucleotide restores dystrophin expression in body-wide skeletal muscles" PNAS (2005) 102(1):198-203.
Madocsai et al., "Correction of SMN2 Pre-mRNA Splicing by Antisense U7 Small Nuclear RN As" Molecular Therapy (2005) 12(6):1013-1022.
Matsuzawa et al., "Age-related volumetric changes of brain gray and white matter in healthy infants and children," Cereb. Cortex, 11(4):335-342 (2001).
Mei, "Fundamentals and Application of Biotechnology Pharmaceutical Formulations," Edt., Chemical Industry Press, 2004, 51-55 (Relevance explained in Chinese Office Action in Chinese Patent Application No. 201710003678.9, dated Jan. 29, 2019.
Miller et al., "Gene-Targeted Therapies for the Central Nervous System", Arch Neurol, 2008:65(4):447-451.
Miyajima et al., "Identification of a Cis-Acting Element for the Regulation of SMN Exon 7 Splicing" J. Biol. Chem. (2002) 277(26):23271-23277.
Miyaso et al., "An Intronic Splicing Enhancer Element in Survival Motor Neuron (SMN) Pre-mRNA" J. Biol. Chem. (2003) 278(18):15825-15831.
New England Biolabs 1998/99 Catalog (cover page and pp. 121 and 284).
Nguyen Thi Man et al., "A two-site ELISA can quantify upregulation of SMN protein by drugs for spinal muscular atrophy," Neurology, 2008, 71(22):1757-1763.

(56) References Cited

OTHER PUBLICATIONS

Ouagazzal, Abdel-Mouttalib., "Reducing Gene Expression in the Brain via Antisense Methods," Current Protocols in Neuroscience, Hoboken: John Wiley & Sons, 2001. N. Chapter 5, 15 pages.
Passini et al., "Antisense Oligonucleotides Delivered to the Mouse CNS Ameliorate Symptoms of Severe Spinal Muscular Atrophy," Science Translational Medicine, 72:72ra18-72ra18 (2011).
Passini et al., "CNS-targeted gene therapy improves survival and motor function in a mouse model of spinal muscular atrophy," J Clin Invest., 120(4):1253-64 (2010).
PCT International Search Report and Written Opinion in International Appln. No. PCT/US2020/042312, dated Oct. 14, 2020, 16 pages.
PCT International Search Report for application PCT/US06/24469 dated Sep. 13, 2007, 2 pages.
PCT International Search Report for application PCT/US2010/30940 dated Jul. 13, 2010, 3 pages.
PCT International Search Report for application PCT/US2010/39077 dated Aug. 17, 2010 2 pages.
PCT International Search Report in International Application No. PCT/EP2009/066903, dated Mar. 26, 2010, 5 pages.
Piepers, "Quantification of SMN protein in leucocytes from spinal muscular atrophy patients: effects of treatment with valproic acid," Journal of Neurology, Neurosurgery & Psychiatry, 2011, 82(8):850-852.
Rebuffat et al., "Gene delivery by a steroid-peptide nucleic acid conjugate" FASEB J. (2002) 19(11):1426-1428.
Reynolds et al., "Rational siRNA design for RNA intelference" Nature Biotechnology (2004) 22(3):326-330.
Rigo et al., "Pharmacology of a central nervous system delivered 2'-O-methoxyethyl-modified survival of motor neuron splicing oligonucleotide in mice and nonhuman primates," Journal of Pharmacology and Experimental Therapeutics, 2014, 350(1):46-55.
Sanghvi et al., "Heterocyclic Base Modifications in Nucleic Acids and Their Applications in Antisense Oligonucleotides" Antisense Research and Applications (1993) pp. 273-288.
Sazani et al., "Therapeutic potential of antisense oligonucleotides as modulators of alternative splicing" The Journal of Clinical Investigation (2003) 112(4):481-486.
Schmid et al., "Animal models of spinal muscular atrophy" Journal of Child Neurology (2007) 22(8):1004-1012.
Shukla et al., "Quantitative determination of human interleukin 22 (IL-22) in serum using Singulex-Erenna® technology," Journal of immunological methods, 2013, 390(1-2):30-34.
Sierakowska et al., "Repair of thalassemic human J3-globin mRNA in mammalian cells by antisense oligonucleotides" PNAS (1996) 93:12840-12844.
Sierakowska et al., "Restoration of B-Globin Gene Expression in Manunalian Cells by Antisense Oligonucleotides That Modify the Aberrant Splicing Patiems of Thalassemic Pre-mRNAs" Nucleosides & Nucleotides (1997) 16(7-9): 1173-1182.
Singh et al., "A Short antisense oligonucleotide masking a unique intronic motif prevents skipping of a critical exon in spinal muscular atrophy," RNA Bio 6(3):341-350 (2009).
Singh et al., "An extended inhibitory context causes skipping of exon 7 of SMN2 in spinal muscular atrophy" Biochem. Biophys. Res. Comm. (2004) 315(2):381-388.
Singh et al., "In vivo selection reveals combinatorial controls that define a critical exon in the spinal muscular atrophy genes" RNA (2004) 10:1291-1305.
Singh et al., "Splicing of a critical exon of human Survival Motor Neuron is regulated by a unique silencer element located in the last intron" Molecular and Cellular Biology (2006) 26(4):1333-1346.
Skordis et al., "Bifunctional Antisense Oligonucleotides Provide a Trans-Acting Splicing Enhancer that Stimulated SMN2 Gene Expression in Patient Fibroblasts" PNAS (2003) 100(7):4114-4119.
Sloop et al., "Hepatic and glucagon-like peptide-1-mediated reversal of diabetes by glucagon receptor antisense oligonucleotide inhibitors", Journal of Clinical Investigation, (2004) 113(11):1571-1581.
Smith, "Antisense oligonucleotide therapy for neurodegenerative disease," Journal of Clinical Investigation, 116:2290-2296 (2006).
Sprinraza (nusinersen) injection, for intrathecal use, FDA Label, Dec. 2016, 13 pages.
Swoboda et al., "0.9 First-in-human phase I study to assess safety, tolerability, and dose for intrathecal injection of ISIS-SMNRx in SMA patients," Neuromuscular Disorders, 23:797-98 (2013).
Swoboda, K., et al. ("O. 9 First-in-human phase I study to assess safety, tolerability and dose for intrathecal injection of ISIS-SMNRx in SMA patients." Neuromuscular Disorders 23.9 (2013):797-798).
Takeshima et al., "Modulation of in vitro splicing of the upstream intron by modifying an intra-exon sequence which is deleted from the dystrophin gene in dystrophin Kobe." J. Clin. Invest. (1995) 95(2):515-520.
Taylor et al., "Induction of endogenous Bcl-xS through the control of Bcl-x pre-mRNA splicing by antisense oligonucleotides" Nat. Biotechnol. (1999) 17: 1097-1100.
Todd et al., "Ultrasensitive flow-based immunoassays using single-molecule counting," Clinical Chemistry, 2007, 53(11):1990-1995.
Translated abstract from JP 2004-344072, 1 page.
Vinogradov et al., "Nanogels for Oligonucleotide Delivery to the Brain" Bioconjugate Chem. (2004) 15:50-60.
Wang, "Antisense oligodeoxynucleotides selectively suppress expression of the mutant alpha 2(1) collagen allele in type IV osteogenesis imperfecta fibroblasts. A molecular approach to therapeutics of dominant negative disorders." J. Clin. Invest. (1996) 97(2):448-454.
Williams et al., "Oligonucleotide-mediated survival of motor neuron protein expression in CNS improves phenotype in a mouse model of Spinal Muscular Atrophy" Journal of Neuroscience (2009) 29(24):76-33-7638.
Wilton et al., "Specific removal of the nonsense mutation from the mdx dystrophin mRNA using antisense oligonucleotides" Neuromuscul. Disord (1999) 9:330-338.
Yeo et al., "Variation in sequences and organization of splicing regulatory elements in vertebrate genes," Proc. Natl. Acad. Sci., 101(44):15700-15705 (2004).
Zhang et al., "An in vivo reporter system for measuring increased inclusion of exon 7 in SMN2 mRNA: potential therapy of SMA," Gene Therapy, (2001), 8:1532-1538.
Zhang, "Modern Drug Design," Edt., China Medical Science and Technology Press, 2006, 271-276 (Relevance explained in Chinese Office Action in Chinese Patent Application No. 201710003678.9, dated Jan. 29, 2019).
Zhou et al., "Mixed-backbone oligonucleotides as second-generation antisense agents with reduced phosphorothioate-related side effects," Bioorganic & Medicinal Chemistry Letters, Nov. 1998, 8(22):3269-3274.
European Extended Search Report in European Application No. 21761502.0, dated Nov. 6, 2023, 5 pages.
U.S. Appl. No. 11/993,609, now U.S. Pat. No. 8,361,977, filed May 6, 2010, Baker.
U.S. Appl. No. 13/720,474, now U.S. Pat. No. 8,946,183, filed Dec. 19, 2012, Baker.
U.S. Appl. No. 14/584,112, filed Dec. 29, 2014, Baker.
U.S. Appl. No. 15/267,408, filed Sep. 16, 2016, Baker.
U.S. Appl. No. 15/818,073, filed Nov. 20, 2017, Baker.
U.S. Appl. No. 16/507,985, filed Jul. 10, 2019, Baker.
U.S. Appl. No. 17/206,762, filed Mar. 19, 2021, Baker.
U.S. Appl. No. 17/510,462, filed Oct. 26, 2021, Baker.
U.S. Appl. No. 17/835,027, filed Jun. 8, 2022, Baker.
U.S. Appl. No. 18/153,179, filed Jan. 11, 2023, Baker.
U.S. Appl. No. 18/474,900, filed Sep. 26, 2023, Baker.
U.S. Appl. No. 13/380,021, now U.S. Pat. No. 8,980,853, filed Apr. 12, 2012, Bennett.
U.S. Appl. No. 14/617,388, now U.S. Pat. No. 9,717,750, filed Feb. 9, 2015, Bennett.
U.S. Appl. No. 15/630,445, filed Jun. 22, 2017, Bennett.
U.S. Appl. No. 15/892,560, filed Feb. 9, 2018, Bennett.
U.S. Appl. No. 16/708,739, filed Dec. 10, 2019, Bennett.
U.S. Appl. No. 17/479,081, filed Sep. 20, 2021, Bennett.
U.S. Appl. No. 17/751,816, filed May 24, 2022, Bennett.
U.S. Appl. No. 18/068,823, filed Dec. 20, 2022, Bennett.
U.S. Appl. No. 18/494,445, filed Oct. 25, 2023, Bennett.

(56) References Cited

OTHER PUBLICATIONS

U.S. Appl. No. 14/760,171, now U.S. Pat. No. 9,926,559, filed Jul. 9, 2015, Bennett.
U.S. Appl. No. 15/907,970, filed Feb. 28, 2018, Bennett.
U.S. Appl. No. 15/931,887, filed May 14, 2020, Bennett.
U.S. Appl. No. 17/130,836, filed Dec. 22, 2020, Bennett.
U.S. Appl. No. 17/394,563, filed Aug. 5, 2021, Bennett.
U.S. Appl. No. 17/715,154, filed Apr. 7, 2022, Bennett.
U.S. Appl. No. 17/986,027, filed Nov. 14, 2022, Bennett.
U.S. Appl. No. 18/342,985, filed Jun. 28, 2023, Bennett.
U.S. Appl. No. 15/509,642, filed Mar. 8, 2017, Rigo.
U.S. Appl. No. 16/538,422, filed Aug. 12, 2019, Rigo.
U.S. Appl. No. 16/829,760, filed Mar. 25, 2020, Rigo.
U.S. Appl. No. 17/100,073, filed Nov. 20, 2020, Rigo.
U.S. Appl. No. 15/303,829, filed Oct. 13, 2016, Rigo.
U.S. Appl. No. 16/248,033, filed Jan. 15, 2019, Rigo.
U.S. Appl. No. 16/554,142, filed Aug. 28, 2019, Rigo.
U.S. Appl. No. 16/837,349, now U.S. Pat. No. 11,535,848, filed Apr. 1, 2020, Rigo.
U.S. Appl. No. 17/991,955, filed Nov. 22, 2022, Rigo.
U.S. Appl. No. 17/626,324, filed Jan. 11, 2022, Loveday.
U.S. Appl. No. 17/187,018, filed Feb. 26, 2021, Rigo.
U.S. Appl. No. 17/356,961, now U.S. Pat. No. 11,299,737, filed Jun. 24, 2021, Rigo.
U.S. Appl. No. 16/310,766, filed Dec. 17, 2018, Rigo.
U.S. Appl. No. 17/127,866, filed Dec. 18, 2020, Rigo.
U.S. Appl. No. 18/046,325, filed Oct. 13, 2022, Rigo.
U.S. Appl. No. 18/359,095, filed Jul. 26, 2023, Rigo.
U.S. Appl. No. 61/168,885, filed Apr. 13, 2009, Krainer et al.
Haynes et al., "Proteome Analysis: Biological Assay or Data Archive?," Electrophoresis, Aug. 1998, 19(11):1862-1871.

SEQUENCE LISTING

```
<160> NUMBER OF SEQ ID NOS: 28

<210> SEQ ID NO 1
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1
tcactttcat aatgctgg                                                  18

<210> SEQ ID NO 2
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 2
tttcataatg ctggc                                                     15

<210> SEQ ID NO 3
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 3
tgctggcaga cttac                                                     15

<210> SEQ ID NO 4
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 4
cataatgctg gcaga                                                     15

<210> SEQ ID NO 5
<211> LENGTH: 15
<212> TYPE: DNA
<213> ORGANISM: Artificial sequence
<220> FEATURE:
```

<223> OTHER INFORMATION: Synthetic oligonucleotide

<400> SEQUENCE: 5
tcataatgct ggcag                                                    15

<210> SEQ ID NO 6
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 6
ttcataatgc tggca                                                    15

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
attcactttc ataatgctgg                                               20

<210> SEQ ID NO 8
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 8
ctttcataat gctgg                                                    15

<210> SEQ ID NO 9
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 9
tcataatgct gg                                                       12

<210> SEQ ID NO 10
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 10
actttcataa tgctg                                                    15

<210> SEQ ID NO 11
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 11
ttcataatgc tg                                                       12

```
<210> SEQ ID NO 12
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 12
cactttcata atgct                                                    15

<210> SEQ ID NO 13
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 13
tttcataatg ct                                                       12

<210> SEQ ID NO 14
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 14
tcactttcat aatgc                                                    15

<210> SEQ ID NO 15
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 15
ctttcataat gc                                                       12

<210> SEQ ID NO 16
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 16
ttcactttca taatg                                                    15

<210> SEQ ID NO 17
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 17
actttcataa tg                                                       12

<210> SEQ ID NO 18
<211> LENGTH: 15
<212> TYPE: DNA
<213> ORGANISM: Artificial sequence
<220> FEATURE:
<223> OTHER INFORMATION: Synthetic oligonucleotide
```

-continued

<400> SEQUENCE: 18
attcactttc ataat                                                    15

<210> SEQ ID NO 19
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 19
cactttcata at                                                       12

<210> SEQ ID NO 20
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 20
gattcacttt cataa                                                    15

<210> SEQ ID NO 21
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 21
tcactttcat aa                                                       12

<210> SEQ ID NO 22
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 22
ttcactttca ta                                                       12

<210> SEQ ID NO 23
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 23
attcactttc at                                                       12

<210> SEQ ID NO 24
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 24
agtaagattc acttt                                                    15

<210> SEQ ID NO 25
<211> LENGTH: 7

```
<212> TYPE: PRT
<213> ORGANISM: Artificial sequence
<220> FEATURE:
<223> OTHER INFORMATION: polypeptide

<400> SEQUENCE: 25

Gly Gly Gly Val Pro Glu Gln
1               5

<210> SEQ ID NO 26
<211> LENGTH: 23
<212> TYPE: PRT
<213> ORGANISM: Artificial sequence
<220> FEATURE:
<223> OTHER INFORMATION: polypeptide

<400> SEQUENCE: 26

Met Ala Met Ser Ser Gly Gly Ser Gly Gly Gly Val Pro Glu Gln Glu
1               5                   10                  15

Asp Ser Val Leu Phe Arg Arg
            20

<210> SEQ ID NO 27
<211> LENGTH: 7
<212> TYPE: PRT
<213> ORGANISM: Artificial sequence
<220> FEATURE:
<223> OTHER INFORMATION: polypeptide

<400> SEQUENCE: 27

Asp Asn Ile Lys Pro Lys Ser
1               5

<210> SEQ ID NO 28
<211> LENGTH: 23
<212> TYPE: PRT
<213> ORGANISM: Artificial sequence
<220> FEATURE:
<223> OTHER INFORMATION: polypeptide

<400> SEQUENCE: 28

Ser Arg Ser Pro Gly Asn Lys Ser Asp Asn Ile Lys Pro Lys Ser Ala
1               5                   10                  15

Pro Trp Asn Ser Phe Leu Pro
            20
```

COMPOSITIONS AND METHODS FOR DETECTION OF SMN PROTEIN IN A SUBJECT AND TREATMENT OF A SUBJECT

SEQUENCE LISTING

The present application is being filed along with a Sequence Listing in electronic format. The Sequence Listing is provided as a file entitled CORE0123WOSEQ_ST25.txt, created Sep. 10, 2015, which is 8 Kb in size. The information in the electronic format of the sequence listing is incorporated herein by reference in its entirety.

BACKGROUND OF THE INVENTION

Newly synthesized eukaryotic mRNA molecules, known as primary transcripts or pre-mRNA are processed before translation. Processing of the pre-mRNAs includes addition of a 5' methylated cap and an approximately 200-250 base poly(A) tail to the 3' end of the transcript. Processing of mRNA from pre-mRNA also frequently involves splicing of the pre-mRNA, which occurs in the maturation of 90-95% of mammalian mRNAs. Introns (or intervening sequences) are regions of a pre-mRNA (or the DNA encoding it) that are not included in the coding sequence of the mature mRNA. Exons are regions of a primary transcript that remain in the mature mRNA. The exons are spliced together to form the mature mRNA sequence. Splice junctions are also referred to as splice sites with the 5' side of the junction often called the "5' splice site," or "splice donor site" and the 3' side the "3' splice site" or "splice acceptor site." In splicing, the 3' end of an upstream exon is joined to the 5' end of the downstream exon. Thus the unspliced pre-mRNA has an exon/intron junction at the 5' end of an intron and an intron/exon junction at the 3' end of an intron. After the intron is removed, the exons are contiguous at what is sometimes referred to as the exon/exon junction or boundary in the mature mRNA. Cryptic splice sites are those which are less often used but may be used when the usual splice site is blocked or unavailable. Alternative splicing, defined as the splicing together of different combinations of exons, often results in multiple mRNA transcripts from a single gene.

Up to 50% of human genetic diseases resulting from a point mutation result in aberrant pre-mRNA processing. Such point mutations can either disrupt a current splice site or create a new splice site, resulting in mRNA transcripts comprised of a different combination of exons or with deletions in exons. Point mutations also can result in activation of a cryptic splice site or disrupt regulatory cis elements (i.e. splicing enhancers or silencers) (Cartegni et al., Nat. Rev. Genet., 2002, 3, 285-298; Drawczak et al., Hum. Genet., 1992, 90, 41-54). Antisense oligonucleotides have been used to target mutations that lead to aberrant splicing in several genetic diseases in order to redirect splicing to give a desired splice product (Kole, *Acta Biochimica Polonica*, 1997, 44, 231-238).

Antisense compounds have also been used to alter the ratio of naturally occurring alternate splice variants such as the long and short forms of Bcl-x pre-mRNA (U.S. Pat. Nos. 6,172,216; 6,214,986; Taylor et al., Nat. Biotechnol. 1999, 17, 1097-1100) or to force skipping of specific exons containing premature termination codons (Wilton et al., Neuromuscul. Disord., 1999, 9, 330-338). U.S. Pat. No. 5,627,274 and WO 94/26887 disclose compositions and methods for combating aberrant splicing in a pre-mRNA molecule containing a mutation using antisense oligonucleotides which do not activate RNAse H.

Proximal spinal muscular atrophy (SMA) is a genetic, neurodegenerative disorder characterized by the loss of spinal motor neurons. SMA is an autosomal recessive disease of early onset and is currently the leading cause of death among infants. The severity of SMA varies among patients and has thus been classified into three types. Type I SMA is the most severe form with onset at birth or within 6 months and typically results in death within 2 years. Children with type I SMA are unable to sit or walk. Type II SMA is the intermediate form and patients are able to sit, but cannot stand or walk. Patients with type III SMA, a chronic form of the disease, typically develop SMA after 18 months of age (Lefebvre et al., Hum. Mol. Genet., 1998, 7, 1531-1536).

The molecular basis of SMA is caused by the loss of both copies of survival motor neuron gene 1 (SMN1), which may also be known as SMN Telomeric, a protein that is part of a multi-protein complex thought to be involved in snRNP biogenesis and recycling. A nearly identical gene, SMN2, which may also be known as SMN Centromeric, exists in a duplicated region on chromosome 5q13 and modulates disease severity. Expression of the normal SMN1 gene results solely in expression of survival motor neuron (SMN) protein. Although SMN1 and SMN2 have the potential to code for the same protein, SMN2 contains a translationally silent mutation at position +6 of exon 7, which results in inefficient inclusion of exon 7 in SMN2 transcripts. Thus, the predominant form of SMN2 is a truncated version, lacking exon 7, which is unstable and inactive (Cartegni and Krainer, Nat. Genet., 2002, 30, 377-384). Expression of the SMN2 gene results in approximately 10-20% of the SMN protein and 80-90% of the unstable/non-functional SMN-delta7 protein. SMN protein plays a well-established role in assembly of the spliceosome and may also mediate mRNA trafficking in the axon and nerve terminus of neurons.

Antisense technology is an effective means for modulating the expression of one or more specific gene products, including alternative splice products, and is uniquely useful in a number of therapeutic, diagnostic, and research applications. The principle behind antisense technology is that an antisense compound, which hybridizes to a target nucleic acid, modulates gene expression activities such as transcription, splicing or translation through one of a number of antisense mechanisms. The sequence specificity of antisense compounds makes them extremely attractive as tools for target validation and gene functionalization, as well as therapeutics to selectively modulate the expression of genes involved in disease.

Certain antisense compounds complementary to SMN2 are known in the art. See for example, WO 2007/002390; U.S. 61/168,885; Hua et al., American J. of Human Genetics (April 2008) 82, 1-15; Singh et al., RNA Bio. 6:3, 1-10 (2009). Certain antisense compounds and methods disclosed herein posses desirable characteristics compared to such compounds and methods known in the art. Chimeric peptide nucleic acid molecules designed to modulate splicing of SMN2 have been described (WO 02/38738; Cartegni and Krainer, Nat. Struct. Biol., 2003, 10, 120-125).

SUMMARY OF THE INVENTION

In certain embodiments, the present disclosure provides methods comprising measuring the amount of SMN protein in the cerebrospinal fluid of a subject. In certain embodiments, the subject has SMA. In certain embodiments, the method of determining the amount of SMN protein in a biological sample, e.g. cerebrospinal fluid, comprises (a) collecting a biological sample from a subject (e.g. cerebrospinal fluid), (b) contacting the biological sample with a capture antibody, (c) contacting the biological sample with a detection antibody, and (d) measuring the amount of detection antibody in the biological sample and calculating the amount of SMN protein in the biological sample.

In certain embodiments, the present disclosure provides methods for optimizing the treatment of a subject having SMA comprising measuring the amount of SMN protein in the cerebrospinal fluid of a subject and then adjusting the subsequent frequency of dosing. In certain embodiments, the present disclosure provides methods for optimizing the treatment of a subject having SMA comprising measuring the amount of SMN protein in the cerebrospinal fluid of a subject and then adjusting amount of subsequent doses administered to the subject. In certain embodiments, the subject is administered ISIS 396443. In certain embodiments, the frequency of dosing of ISIS 396443 is increased. In certain embodiments, the frequency of dosing of ISIS 396443 is decreased. In certain embodiments, the amount of ISIS 396443 administered to a patient is increased. In certain embodiments, the amount of ISIS 396443 administered to a patient is decreased. In certain embodiments, calculation of the amount of SMN protein in the biological sample informs a physician about the amount and frequency of subsequent doses of ISIS 396443.

In certain embodiments, the present disclosure provides methods of determining the dosing frequency of ISIS 396443 comprising:
  administering a first dose of ISIS 396443 to a subject in need thereof;
  detecting the amount of SMN2 protein in a sample of cerebrospinal fluid according to the methods described herein at the time a second dose is administered; and
  increasing or decreasing the frequency of any subsequent doses of ISIS 396443.

In certain embodiments, the present disclosure provides methods of determining the dosing frequency of ISIS 396443 comprising:
  administering a first dose of ISIS 396443 to a subject in need thereof;
  detecting the amount of SMN2 protein in a sample of cerebrospinal fluid according to the methods disclosed herein at the time the first dose is administered;
  detecting the amount of SMN2 protein in a sample of cerebrospinal fluid according to the methods disclosed herein at the time the second dose is administered; and
  increasing or decreasing the frequency of any subsequent doses of ISIS 396443.

In certain embodiments, the present disclosure provides a kit for detecting the amount of SMN protein in a sample of cerebrospinal fluid comprising: a capture antibody labeled with a magnetic microparticle; and a detection antibody labeled with a fluorophore.

In certain embodiments, the present disclosure provides a diagnostic kit for detecting the amount of SMN protein in a sample of cerebrospinal fluid comprising: a capture antibody labeled with a magnetic microparticle; a detection antibody labeled with a fluorophore.

In certain embodiments, the present disclosure provides a kit for detecting the amount of SMN protein in a sample of cerebrospinal fluid comprising: a capture antibody labeled with a magnetic microparticle configured to bind with high specificity to an SMN protein; a detection antibody labeled with a fluorophore configured to bind with high specificity to an SMN protein; a device configured to detect the detection antibody labeled with a fluorophore and to calculate the concentration of SMN protein in the sample of cerebrospinal fluid.

In certain embodiments, the present disclosure provides methods comprising administering to a subject an antisense compound comprising an antisense oligonucleotide complementary to intron 7 of a nucleic acid encoding human SMN2 pre-mRNA, wherein the antisense compound is administered into the cerebrospinal fluid. In certain embodiments, the administration is into the intrathecal space. In certain embodiments, the administration is into the cerebrospinal fluid in the brain. In certain embodiments, the administration comprises a bolus injection. In certain embodiments, the administration comprises infusion with a delivery pump.

The present disclosure provides the following non-limiting numbered embodiments:

Embodiment 1: A method of determining the amount of SMN protein in a biological sample comprising:
  a. collecting a biological sample from a subject;
  b. contacting the biological sample with a capture antibody;
  c. contacting the biological sample with a detection antibody;
  d. measuring the amount of detection antibody in the biological sample; and calculating the amount of SMN protein in the biological sample.

Embodiment 2: The method of embodiment 1, wherein the biological sample is cerebrospinal fluid.

Embodiment 3: The method of embodiment 1 or 2, wherein the biological sample is contacted with the capture antibody before it is contacted with the detection antibody.

Embodiment 4: The method of any of embodiments 1-3, comprising at least one wash step.

Embodiment 5: The method of any of embodiments 1-4, comprising at least one wash step prior to detecting the detection antibody.

Embodiment 6: The method of any of embodiments 1-5, wherein the capture antibody recognizes an N-terminal epitope of the SMN2 protein.

Embodiment 7: The method of any of embodiments 1-6, wherein the capture antibody specifically binds to a polypeptide sequence comprising SEQ ID NO: 25.

Embodiment 8: The method of any of embodiments 1-7, wherein the capture antibody specifically binds to the polypeptide of SEQ ID NO: 26.

Embodiment 9: The method of any of embodiments 1-8, wherein the capture antibody is labeled with a magnetic microparticle.

Embodiment 10: The method of any of embodiments 1-9, wherein the capture antibody is Millipore antibody MABE230.

Embodiment 11: The method of any of embodiments 1-10, wherein the detection antibody specifically binds to the polypeptide of SEQ ID NO: 27.

Embodiment 12: The method of any of embodiments 1-11, wherein the detection antibody specifically binds to the polypeptide of SEQ ID NO: 28.

Embodiment 13: The method of any of embodiments 1-12, wherein the detection antibody is labeled with a fluorophore.

Embodiment 14: The method of any of embodiments 1-13, wherein the detection antibody is ProteinTech antibody #60154-1-Ig.

Embodiment 15: The method of any of embodiments 1-14, wherein a salt and a surfactant are added to the sample of the cerebrospinal fluid under conditions selected to form an assay buffer.

Embodiment 16: The method of embodiment 15, wherein the salt is NaCl.

Embodiment 17: The method of any of embodiments 15-16, wherein the salt is present in a concentration of 100 to 1000 mM.

Embodiment 18: The method of any of embodiments 15-17, wherein the salt is present in a concentration of 150 mM.

Embodiment 19: The method of any of embodiments 15-18, wherein the surfactant is Triton-X detergent.

Embodiment 20: The method of any of embodiments 15-19, wherein the surfactant is between 0.1% and 1.5% of the total volume of the assay buffer.

Embodiment 21: The method of any of embodiments 15-20, wherein the surfactant is 0.25% of the volume of the assay buffer.

Embodiment 22: The method of any of embodiments 1-21, wherein a sandwich immunoassay is used to detect the amount of SMN2 protein.

Embodiment 23: The method of any of embodiments 1-22, wherein the Singulex Erenna system is used to detect the amount of SMN2 protein.

Embodiment 24: The method of any of embodiments 1-22, wherein an ELISA assay is used to detect the amount of SMN2 protein.

Embodiment 25: The method of any of embodiments 1-24, wherein the subject is an animal.

Embodiment 26: The method of embodiment 25, wherein the animal is a human.

Embodiment 27: The method of embodiment 25, wherein the animal is a mouse.

Embodiment 28: The method of embodiment 25, wherein the animal is a primate.

Embodiment 29: The method of any of embodiments 1-28, wherein the subject has spinal muscular atrophy (SMA).

Embodiment 30: The method of embodiment 29, wherein the subject has type I SMA.

Embodiment 31: The method of embodiment 29, wherein the subject has type II SMA.

Embodiment 32: The method of embodiment 29, wherein the subject has type III SMA.

Embodiment 33: The method of embodiment 29, wherein the subject has type IV SMA.

Embodiment 34: The method of any of embodiments 1-33, wherein the subject has received at least one dose of a pharmaceutical agent for the treatment of SMA.

Embodiment 35: The method of embodiment 34, wherein the pharmaceutical agent for the treatment of SMA is an antisense compound.

Embodiment 36: The method of embodiment 35, wherein the antisense compound is ISIS396443.

Embodiment 37: The method of any of embodiments 1 to 36, wherein the amount of SMN protein detected is between 0.1 pg/mL-10 pg/mL.

Embodiment 38: The method of any of embodiments 1 to 36, wherein the amount of SMN protein detected is between 0.2 pg/mL-10 pg/mL.

Embodiment 39: The method of any of embodiments 1 to 36, wherein the amount of SMN protein detected is between 0.3 pg/mL-10 pg/mL.

Embodiment 40: The method of any of embodiments 1 to 36, wherein the amount of SMN protein detected is between 0.4 pg/mL-10 pg/mL.

Embodiment 41: The method of any of embodiments 1 to 36, wherein the amount of SMN protein detected is between 0.5 pg/mL-10 pg/mL.

Embodiment 42: The method of any of embodiments 1 to 36, wherein the amount of SMN protein detected is between 0.6 pg/mL-10 pg/mL.

Embodiment 43: The method of any of embodiments 1 to 36, wherein the amount of SMN protein detected is between 0.7 pg/mL-10 pg/mL.

Embodiment 44: The method of any of embodiments 1 to 36, wherein the amount of SMN protein detected is between 0.5 pg/mL-9 pg/mL.

Embodiment 45: The method of any of embodiments 1 to 36, wherein the amount of SMN protein detected is between 0.5 pg/mL-8 pg/mL.

Embodiment 46: The method of any of embodiments 1 to 36, wherein the amount of SMN protein detected is between 0.5 pg/mL-7 pg/mL.

Embodiment 47: The method of any of embodiments 1 to 36, wherein the amount of SMN protein detected is between 0.5 pg/mL-6 pg/mL.

Embodiment 48: The method of any of embodiments 1 to 36, wherein the amount of SMN protein detected is between 0.5 pg/mL-5 pg/mL.

Embodiment 49: The method of any of embodiments 1 to 36, wherein the amount of SMN protein detected is less than 10 pg/mL.

Embodiment 50: The method of any of embodiments 1 to 36, wherein the amount of SMN protein detected is less than 9 pg/mL.

Embodiment 51: The method of any of embodiments 1 to 36, wherein the amount of SMN protein detected is less than 8 pg/mL.

Embodiment 52: The method of any of embodiments 1 to 36, wherein the amount of SMN protein detected is less than 7 pg/mL.

Embodiment 53: The method of any of embodiments 1 to 36, wherein the amount of SMN protein detected is less than 6 pg/mL.

Embodiment 54: The method of any of embodiments 1 to 36, wherein the amount of SMN protein detected is less than 5 pg/mL.

Embodiment 55: The method of any of embodiments 1 to 36, wherein the amount of SMN protein detected is less than 4 pg/mL.

Embodiment 56: The method of any of embodiments 1 to 36, wherein the amount of SMN protein detected is less than 3 pg/mL.

Embodiment 57: The method of any of embodiments 1 to 36, wherein the amount of SMN protein detected is less than 2 pg/mL.

Embodiment 58: The method of any of embodiments 1 to 36, wherein the amount of SMN protein detected is less than 1.0 pg/mL.

Embodiment 59: A method of treating a subject having SMA comprising:
  a. detecting the amount of SMN protein in a sample of cerebrospinal fluid according to the method of any of embodiments 1-58; and
  b. administering one or more doses of ISIS 396443.

Embodiment 60: A method of determining the dosing frequency of ISIS 396443 comprising:
  a. Administering a first dose of ISIS 396443 to a subject in need thereof;
  b. detecting the amount of SMN protein in a sample of cerebrospinal fluid according to the method of any of embodiments 1-58 at the time a second dose is administered; and
  c. increasing or decreasing the frequency of any subsequent doses of ISIS 396443.

Embodiment 61: A method of determining the dosing frequency of ISIS 396443 comprising:
  a. Administering a first dose of ISIS 396443 to a subject in need thereof;
  b. detecting the amount of SMN protein in a sample of cerebrospinal fluid according to the method of any of embodiments 1-58 at the time the first dose is administered;
  c. detecting the amount of SMN protein in a sample of cerebrospinal fluid according to the method of any of embodiments 1-58 at the time the second dose is administered; and
  d. increasing or decreasing the frequency of any subsequent doses of ISIS 396443.

Embodiment 62: The method of embodiment 60 or 61, wherein the frequency of the subsequent dose is increased.

Embodiment 63: The method of embodiment 60 or 61, wherein the frequency of the subsequent dose is decreased.

Embodiment 64: The method of any of embodiments 60-63, wherein the second dose is administered between 12 and 18 days after the first dose.

Embodiment 65: The method of any of embodiments 60-63, wherein the second dose is administered between 24 and 34 days after the first dose.

Embodiment 66: The method of any of embodiments 60-63, wherein the second dose is administered between 80-90 days after the first dose.

Embodiment 67: The method of any of embodiments 60-63, wherein the second dose is administered 12-18 days after the first dose, and wherein a subsequent dose is administered 25-35 days after the first dose.

Embodiment 68: The method of any of embodiments 60-63, wherein the second dose is administered 12-18 days after the first dose, and wherein a subsequent dose is administered 80-90 days after the first dose.

Embodiment 69: The method of any of embodiments 60-63, wherein the second dose is administered 25-35 days after the first dose, a third dose is administered 80-90 days after the first dose, and a fourth dose is administered 270-280 days after the first dose.

Embodiment 70: The method of any of embodiments 60-63, wherein the second dose is administered 25-35 days after the first dose, a third dose is administered 80-90 days after the first dose, a fourth dose is administered 270-280 days after the first dose, and each subsequent dose thereafter is administered at six month intervals.

Embodiment 71: The method of any of embodiments 60-63, wherein the second dose is administered 12-18 days after the first dose, a third dose is administered 25-35 days after the first dose, a fourth dose is administered 60-70 days after the first dose, a fifth dose is administered 178-188 days after the first dose, and a sixth dose is administered 298-308 days after the first dose is administered.

Embodiment 72: The method of any of embodiments 59-71, wherein the amount of SMN protein detected at the time the second dose is administered is 50% greater than the amount of SMN protein detected at the time the first dose was administered.

Embodiment 73: The method of any of embodiments 59-71, wherein the amount of SMN protein detected at the time the second dose is administered is 60% greater than the amount of SMN protein detected at the time the first dose was administered.

Embodiment 74: The method of any of embodiments 59-71, wherein the amount of SMN protein detected at the time the second dose is administered is 70% greater than the amount of SMN protein detected at the time the first dose was administered.

Embodiment 75: The method of any of embodiments 59-71, wherein the amount of SMN protein detected at the time the second dose is administered is 80% greater than the amount of SMN protein detected at the time the first dose was administered.

Embodiment 76: The method of any of embodiments 59-71, wherein the amount of SMN protein detected at the time the second dose is administered is 90% greater than the amount of SMN protein detected at the time the first dose was administered.

Embodiment 77: The method of any of embodiments 59-71, wherein the amount of SMN protein detected at the time the second dose is administered is 100% greater than the amount of SMN protein detected at the time the first dose was administered.

Embodiment 78: The method of any of embodiments 59-71, wherein the amount of SMN protein detected at the time the second dose is administered is at least 100% greater than the amount of SMN protein detected at the time the first dose was administered.

Embodiment 79: The method of any of embodiments 59-71, wherein the amount of SMN protein detected at the time the second dose is administered is at least 110% greater than the amount of SMN protein detected at the time the first dose was administered.

Embodiment 80: The method of any of embodiments 59-71, wherein the amount of SMN protein detected at the time the second dose is administered is at least 120% greater than the amount of SMN protein detected at the time the first dose was administered.

Embodiment 81: The method of any of embodiments 59-71, wherein the amount of SMN protein detected at the time the second dose is administered is at least 150% greater than the amount of SMN protein detected at the time the first dose was administered.

Embodiment 82: The method of any of embodiments 59-71, wherein the amount of SMN protein detected at the time the second dose is administered is at least 200% greater than the amount of SMN protein detected at the time the first dose was administered.

Embodiment 83: The method of any of embodiments 59-71, wherein the dose is about 1 milligram.

Embodiment 84: The method of any of embodiments 59-71, wherein the dose is about 2 milligrams.

Embodiment 85: The method of any of embodiments 59-71, wherein the dose is about 3 milligrams.

Embodiment 86: The method of any of embodiments 59-71, wherein the dose is about 4 milligrams.

Embodiment 87: The method of any of embodiments 59-71, wherein the dose is about 5 milligrams.

Embodiment 88: The method of any of embodiments 59-71, wherein the dose is about 6 milligrams.

Embodiment 89: The method of any of embodiments 59-71, wherein the dose is about 7 milligrams.
Embodiment 90: The method of any of embodiments 59-71, wherein the dose is about 8 milligrams.
Embodiment 91: The method of any of embodiments 59-71, wherein the dose is about 9 milligrams.
Embodiment 92: The method of any of embodiments 59-71, wherein the dose is about 10 milligrams.
Embodiment 93: The method of any of embodiments 59-71, wherein the dose is about 11 milligrams.
Embodiment 94: The method of any of embodiments 59-71, wherein the dose is about 12 milligrams.
Embodiment 95: The method of any of embodiments 59-71, wherein the dose is about 13 milligrams.
Embodiment 96: The method of any of embodiments 59-71, wherein the dose is about 14 milligrams.
Embodiment 97: The method of any of embodiments 59-71, wherein the dose is about 15 milligrams.
Embodiment 98: The method of any of embodiments 59-71, wherein the dose is less than 20 milligrams.
Embodiment 99: The method of any of embodiments 59-71, wherein the dose is less than 15 milligrams.
Embodiment 100: The method of any of embodiments 59-71, wherein the dose is less than 10 milligrams.
Embodiment 101: The method of any of embodiments 59-71, wherein the dose is less than 5 milligrams.
Embodiment 102: The method of any of embodiments 59-71, wherein the dose is about 4.8 milligrams.
Embodiment 103: The method of any of embodiments 59-71, wherein the dose is about 5.16 milligrams.
Embodiment 104: The method of any of embodiments 59-71, wherein the dose is about 5.4 milligrams.
Embodiment 105: The method of any of embodiments 59-71, wherein the dose is about 7.2 milligrams.
Embodiment 106: The method of any of embodiments 59-71, wherein the dose is about 7.74 milligrams.
Embodiment 107: The method of any of embodiments 59-71, wherein the dose is about 8.10 milligrams.
Embodiment 108: The method of any of embodiments 59-71, wherein the dose is about 9.60 milligrams.
Embodiment 109: The method of any of embodiments 59-71, wherein the dose is about 10.32 milligrams.
Embodiment 110: The method of any of embodiments 59-71, wherein the dose is about 10.80 milligrams.
Embodiment 111: The method of any of embodiments 59-71, wherein the dose is about 11.3 milligrams.
Embodiment 112: The method of any of embodiments 59-71, wherein the dose is about 12.88 milligrams.
Embodiment 113: The method of any of embodiments 59-71, wherein the dose is about 13.5 milligrams.
Embodiment 114: The method of any of embodiments 59-71, wherein the dose is about 14.13 milligrams.
Embodiment 115: The method of any of embodiments 59-71, wherein the dose is about 12.9 milligrams.
Embodiment 116: The method of any of embodiments 59-71, wherein the dose is about 13.5 milligrams.
Embodiment 117: The method of any of embodiments 59-71, wherein the dose is about 14.4 milligrams.
Embodiment 118: The method of any of embodiments 59-71, wherein the dose is about 15.5 milligrams.
Embodiment 119: The method of any of embodiments 59-71, wherein the dose is about 16.2 milligrams.
Embodiment 120: The method of any of embodiments 59-71, wherein the dose is about 17.0 milligrams.
Embodiment 121: The method of any of embodiments 59-71, wherein the dose is about 16 milligrams.
Embodiment 122: The method of any of embodiments 59-71, wherein the dose is about 18 milligrams.
Embodiment 123: The method of any of embodiments 1-22, wherein the dose is an equivalent dose.
Embodiment 124: The method of any of embodiments 1-22, wherein the dose is an adjusted dose.
Embodiment 125: The method of embodiment 124, wherein the adjusted dose is determined by CSF volume scaling.
Embodiment 126: A kit for detecting the amount of SMN protein in a sample of cerebrospinal fluid comprising:
a. a capture antibody labeled with a magnetic microparticle;
b. a detection antibody labeled with a fluorophore.
Embodiment 127: A diagnostic kit for detecting the amount of SMN protein in a sample of cerebrospinal fluid comprising:
a. a capture antibody labeled with a magnetic microparticle;
b. a detection antibody labeled with a fluorophore.
Embodiment 128: A kit for detecting the amount of SMN protein in a sample of cerebrospinal fluid comprising:
a. a capture antibody labeled with a magnetic microparticle configured to bind with high specificity to an SMN protein;
b. a detection antibody labeled with a fluorophore configured to bind with high specificity to an SMN protein;
c. a device configured to detect the detection antibody labeled with a fluorophore and to calculate the concentration of SMN protein in the sample of cerebrospinal fluid.
Embodiment 129: The kit of any of embodiments 126-128, wherein the capture antibody is Millipore antibody MABE230.
Embodiment 130: The kit of any of embodiments 126-129, wherein the detection antibody is ProteinTech antibody #60154-1-Ig.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

I. Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 18th edition, 1990; and "Antisense Drug Technology, Principles, Strategies, and Applications" Edited by Stanley T. Crooke, CRC Press, Boca Raton, Florida; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure herein are incorporated by reference in their entirety.

Unless otherwise indicated, the following terms have the following meanings:

"Nucleoside" means a compound comprising a heterocyclic base moiety and a sugar moiety. Nucleosides include, but are not limited to, naturally occurring nucleosides, modified nucleosides, and nucleosides having mimetic bases and/or sugar groups. Nucleosides may be modified with any of a variety of substituents.

"Sugar moiety" means a natural or modified sugar or sugar surrogate.

"Natural sugar" means a ribofuranose moiety of DNA (2'-H) or RNA (2'-OH).

"Modified sugar" means a ribofuranose moiety comprising at least one substituent other than that of a natural sugar.

"Sugar surrogate" means a structure other than a ribofuranose ring which is capable of substituting for the sugar of a nucleoside. Examples of sugar surrogates include, but are not limited to, open ring systems, 6-membered rings, sugars in which the oxygen is replace with, for example, sulfur or nitrogen. For example, sugar surrogates include, but are not limited to morpholinos and 4'-thio-containing sugars.

"Nucleobase" means the heterocyclic base portion of a nucleoside. Nucleobases may be naturally occurring or may be modified. In certain embodiments, a nucleobase may comprise any atom or group of atoms capable of hydrogen bonding to a nucleobase of another nucleic acid.

"Nucleotide" means a nucleoside comprising a phosphate linking group. As used herein, nucleosides include nucleotides.

"Modified nucleoside" a nucleoside comprising at least one modification compared to naturally occurring RNA or DNA nucleosides. Such modification may be at the sugar moiety and/or at the nucleobase.

"Bicyclic nucleoside" or "BNA" means a nucleoside wherein the sugar moiety of the nucleoside comprises a bridge connecting two carbon atoms of the sugar ring, thereby forming a bicyclic sugar moiety.

"4'-2' bicyclic nucleoside" means a bicyclic nucleoside comprising a furanose ring comprising a bridge connecting two carbon atoms of the furanose ring connects the 2' carbon atom and the 4' carbon atom of the sugar ring.

"2'-modified" or "2'-substituted" means a nucleoside comprising a sugar comprising a substituent at the 2' position other than H or OH.

"2'-OMe" or "2'-OCH$_3$" or "2'-O-methyl" each means a nucleoside comprising a sugar comprising an —OCH$_3$ group at the 2' position of the sugar ring.

"MOE" or "2'-MOE" or "2'-OCH$_2$CH$_2$OCH$_3$" or "2'-O-methoxyethyl" each means a nucleoside comprising a sugar comprising a —OCH$_2$CH$_2$OCH$_3$ group at the 2' position of the sugar ring.

"Oligonucleotide" means a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

"Oligonucleoside" means an oligonucleotide in which none of the internucleoside linkages contains a phosphorus atom. As used herein, oligonucleotides include oligonucleosides.

"Modified oligonucleotide" means an oligonucleotide comprising at least one modified nucleoside and/or at least one modified internucleoside linkage.

"Internucleoside linkage" means a covalent linkage between adjacent nucleosides of an oligonucleotide.

"Naturally occurring internucleoside linkage" means a 3' to 5' phosphodiester linkage.

"Modified internucleoside linkage" means any internucleoside linkage other than a naturally occurring internucleoside linkage.

"Oligomeric compound" means a compound comprising an oligonucleotide. In certain embodiments, an oligomeric compound consists of an oligonucleotide. In certain embodiments, an oligomeric compound further comprises one or more conjugate and/or terminal groups.

"Antisense compound" means an oligomeric compound, at least a portion of which is at least partially complementary to a target nucleic acid to which it hybridizes, wherein such hybridization results at least one antisense activity.

"Antisense oligonucleotide" means an antisense compound wherein the oligomeric compound consists of an oligonucleotide.

"Antisense activity" refers to any detectable and/or measurable effect attributable to the hybridization of an antisense compound to its target nucleic acid. In certain embodiments, such antisense activity is an increase or decrease in an amount of a nucleic acid or protein. In certain embodiments, such antisense activity is a change in the ratio of splice variants of a nucleic acid or protein. In certain embodiments, such antisense activity is a phenotypic change in a cell and/or subject.

"Detecting" or "measuring" of antisense activity may be direct or indirect. For example, in certain embodiments, antisense activity is assessed by detecting and/or measuring the amount of target nucleic acid or protein or the relative amounts of splice variants of a target nucleic acid or protein. In certain embodiments, antisense activity is detected by observing a phenotypic change in a cell or animal. In connection with any activity, response, or effect, the terms "detecting" and "measuring," indicate that a test for detecting or measuring is performed. Such detection and/or measuring may include values of zero. Thus, if a test for detection or measuring results in a finding of no activity (activity of zero), the step of detecting or measuring the activity has nevertheless been performed.

"Target nucleic acid" refers to any nucleic acid molecule the expression, amount, or activity of which is capable of being modulated by an antisense compound.

"Target mRNA" means a pre-selected RNA molecule that encodes a protein.

"Target pre-mRNA" means a pre-selected RNA transcript that has not been fully processed into mRNA. Notably, pre-mRNA includes one or more intron.

"Target protein" means a protein encoded by a target nucleic acid.

"Modulation" means to a perturbation of function or activity. In certain embodiments, modulation means an increase in gene expression. In certain embodiments, modulation means a decrease in gene expression.

"Expression" means any functions and steps by which a gene's coded information is converted into structures present and operating in a cell.

"Nucleobase sequence" means the order of contiguous nucleobases, in a 5' to 3' orientation, independent of any sugar, linkage, and/or nucleobase modification.

"Contiguous nucleobases" means nucleobases immediately adjacent to each other in a nucleic acid.

"Nucleobase complementarity" means the ability of two nucleobases to pair non-covalently via hydrogen bonding.

"Complementary" means that a first nucleic acid is capable of hybridizing to a second nucleic acid under stringent hybridization conditions. For example, an antisense compound is complementary to its target nucleic acid if it is capable of hybridizing to the target nucleic acid under stringent hybridization conditions.

"Fully complementary" means each nucleobase of a first nucleic acid is capable of pairing with a nucleobase at each corresponding contiguous position in a second nucleic acid.

"Percent complementarity" of an antisense compound means the percentage of nucleobases of the antisense compound that are complementary to an equal-length portion of a target nucleic acid. Percent complementarity is calculated by dividing the number of nucleobases of the antisense oligonucleotide that are complementary to nucleobases at corresponding contiguous positions in the target nucleic acid by the total length of the antisense compound.

"Percent identity" means the number of nucleobases in first nucleic acid that are identical to nucleobases at corresponding positions in a second nucleic acid, divided by the total number of nucleobases in the first nucleic acid.

"Hybridize" means the annealing of complementary nucleic acids that occurs through nucleobase complementarity.

"Mismatch" means a nucleobase of a first nucleic acid that is not capable of pairing with a nucleobase at a corresponding position of a second nucleic acid.

"Identical nucleobase sequence" means having the same nucleobase sequence, independent of any chemical modifications to the nucleosides.

"Different modifications" or "differently modified" refer to nucleosides or internucleoside linkages that have different nucleoside modifications or internucleoside linkages than one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified, unless otherwise indicated. For example, a nucleoside comprising a 2'-OMe modified sugar and an adenine nucleobase and a nucleoside comprising a 2'-OMe modified sugar and a thymine nucleobase are not differently modified.

"The same modifications" refer to nucleosides and internucleoside linkages (including unmodified nucleosides and internucleoside linkages) that are the same as one another. Thus, for example, two unmodified DNA nucleoside have "the same modification," even though the DNA nucleoside is unmodified.

"Type of modification" or nucleoside of a "type" means the modification of a nucleoside and includes modified and unmodified nucleosides. Accordingly, unless otherwise indicated, a "nucleoside having a modification of a first type" may be an unmodified nucleoside.

"Separate regions" of an oligonucleotide means a portion of an oligonucleotide wherein the nucleosides and internucleoside linkages within the region all comprise the same modifications; and the nucleosides and/or the internucleoside linkages of any neighboring portions include at least one different modification.

"Motif" means a pattern of modified and/or unmodified nucleobases, sugars, and/or internucleoside linkages in an oligonucleotide.

"Fully modified oligonucleotide" means each nucleobase, each sugar, and/or each internucleoside linkage is modified.

"Uniformly modified oligonucleotide" means each nucleobase, each sugar, and/or each internucleoside linkage has the same modification throughout the modified oligonucleotide.

"Alternating motif" means an oligonucleotide or a portion thereof, having at least four separate regions of modified nucleosides in a pattern $(AB)_nA_m$ where A represents a region of nucleosides having a first type of modification; B represent a region of nucleosides having a different type of modification; n is 2-15; and m is 0 or 1. Thus, in certain embodiments, alternating motifs include 4, 5, 6, 7, 8, 9, 10, 11, 12, 13, 14, 15, 16, 17, 18, 19, or 20 or more alternating regions. In certain embodiments, each A region and each B region independently comprises 1-4 nucleosides.

"Subject" means a human or non-human animal selected for treatment or therapy.

"Subject in need thereof" means a subject identified as in need of a therapy or treatment. In such embodiments, a subject has one or more indications of having or developing SMA.

"Administering" means providing a pharmaceutical agent or composition to a subject, and includes, but is not limited to, administering by a medical professional and self-administering.

"Parenteral administration," means administration through injection or infusion. Parenteral administration includes, but is not limited to, subcutaneous administration, intravenous administration, or intramuscular administration.

"Systemic administration" means administration to an area other than the intended locus of activity. Examples or systemic administration are subcutaneous administration and intravenous administration, and intraperitoneal administration.

"Subcutaneous administration" means administration just below the skin.

"Intravenous administration" means administration into a vein.

"Cerebrospinal fluid" or "CSF" means the fluid filling the space around the brain and spinal cord.

"Administration into the cerebrospinal fluid" means any administration that delivers a substance directly into the CSF.

"Intracerebroventricular" or "ICV" mean administration into the ventricular system of the brain.

"Intrathecal" or "IT" means administration into the CSF under the arachnoid membrane which covers the brain and spinal cord. IT injection is performed through the theca of the spinal cord into the subarachnoid space, where a pharmaceutical agent is injected into the sheath surrounding the spinal cord.

"Induction phase" means a dosing phase during which administration is initiated and steady state concentrations of active pharmaceutical agent are achieved in a target tissue. For example, an induction phase is a dosing phase during which steady state concentrations of antisense oligonucleotide are achieved in liver.

"Maintenance phase" means a dosing phase after target tissue steady state concentrations of drug have been achieved.

"Duration" means the period of time during which an activity or event continues. For example, the duration of an induction phase is the period of time during which induction doses are administered.

"Maintenance dose" means a dose administered at a single administration during the maintenance phase. As used herein, "induction dose" means a dose administered at a single administration during the induction phase.

"Co-administration" means administration of two or more pharmaceutical agents to a subject. The two or more pharmaceutical agents may be in a single pharmaceutical composition, or may be in separate pharmaceutical compositions. Each of the two or more pharmaceutical agents may be administered through the same or different routes of administration. Co-administration encompasses administration in parallel or sequentially.

"Therapy" means a disease treatment method. In certain embodiments, therapy includes, but is not limited to surgical therapies, chemical therapies, and physical interventions, such as assisted respiration, feeding tubes, and physical therapy for the purpose of increasing strength.

"Treatment" means the application of one or more specific procedures used for the cure or amelioration of a disease. In certain embodiments, the specific procedure is the administration of one or more pharmaceutical agents.

"Amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"Prevent the onset of" means to prevent the development a condition or disease in a subject who is at risk for developing the disease or condition. In certain embodiments, a subject at risk for developing the disease or condition receives treatment similar to the treatment received by a subject who already has the disease or condition.

"Delay the onset of" means to delay the development of a condition or disease in a subject who is at risk for developing the disease or condition.

"Slow the progression of" means that the severity of at least one symptom associated with a disease or condition worsens less quickly.

"Exon 7 amino acids" means the portion of an SMN protein that correspond to exon 7 of the SMN RNA. Exon 7 amino acids are present in SMN protein expressed from SMN RNA where exon 7 was not excluded during splicing.

"SMN protein" means normal full length survival motor neuron protein. SMN may be expressed from either an SMN1 gene or from an SMN2 gene, provided that exon 7 is present in the mature mRNA and the exon 7 amino acids are present in the SMN protein.

"Dose" means a specified quantity of a pharmaceutical agent provided in a single administration or over a specified amount of time. In certain embodiments, a dose may be administered in two or more boluses, tablets, or injections. For example, in certain embodiments, where subcutaneous or intrathecal or ICV administration is desired, the desired dose requires a volume not easily accommodated by a single injection. In such embodiments, two or more injections may be used to achieve the desired dose. In the setting of continuous infusion, dose may be expressed as the quantity of a pharmaceutical agent delivered per unit of time.

"Dosage unit" means a form in which a pharmaceutical agent is provided. In certain embodiments, a dosage unit is a vial containing lyophilized oligonucleotide. In certain embodiments, a dosage unit is a vial containing reconstituted oligonucleotide.

"Equivalent dose" means a dose amount that is used to calculate an adjusted dose, wherein the adjusted dose is based on the CSF volume, dose concentration, or any other criteria known to one having skill in the art. For example, in certain embodiments it may be desirable to administer an equivalent dose of 12 mg of ISIS 396443 to a patient having one or more symptoms of SMA, however based on the patient's age and estimated CSF volume the actual dose of ISIS 396443 may be adjusted to an amount less than 12 mg. For example, it may be desirable to administer an equivalent dose of 12 mg of ISIS 396443 to an SMA patient between 0 and 3 months of age, however based on the patient's age and estimated CSF volume, the actual adjusted dose of ISIS 396443 received by the SMA patient would be 9.6 mg. In certain embodiments, adjusted doses may be calculated based on a desired equivalent dose by using CSF volume scaling as described in Matsuzawa J, Matsui M, Konishi T, Noguchi K, Gur R C, Bilker W, Miyawaki T. Age-related volumetric changes of brain gray and white matter in healthy infants and children. Cereb Cortex 2001 April; 11(4):335-342, which is hereby incorporated by reference in its entirety).

"Adjusted dose" means a dose that is adjusted from a dose or equivalent dose. In certain embodiments and adjusted dose is based on one or more criteria known to those having skill in the art. In certain embodiments the adjusted dose is based on the patient's age, weight, or estimated CSF volume. In certain embodiments, an adjusted dose is derived from an equivalent dose. In certain embodiments, adjusted doses may be calculated based on a desired equivalent dose by using CSF volume scaling as described in Matsuzawa J, Matsui M, Konishi T, Noguchi K, Gur R C, Bilker W, Miyawaki T. Age-related volumetric changes of brain gray and white matter in healthy infants and children. Cereb Cortex 2001 April; 11(4):335-342, which is hereby incorporated by reference in its entirety).

"Therapeutically effective amount" means an amount of a pharmaceutical agent that provides a therapeutic benefit to an animal.

"Pharmaceutical composition" means a mixture of substances suitable for administering to an individual that includes a pharmaceutical agent. For example, a pharmaceutical composition may comprise a modified oligonucleotide and a sterile aqueous solution.

"Acceptable safety profile" means a pattern of side effects that is within clinically acceptable limits.

"Side effect" means a physiological response attributable to a treatment other than desired effects.

1. Certain Modified Oligonucleotides

In certain embodiments, the present invention provides methods and compositions involving antisense oligonucleotides comprising one or more modification compared to oligonucleotides of naturally occurring oligomers, such as DNA or RNA. Such modified antisense oligonucleotides may possess one or more desirable properties. Certain such modifications alter the antisense activity of the antisense oligonucleotide, for example by increasing affinity of the antisense oligonucleotide for its target nucleic acid, increasing its resistance to one or more nucleases, and/or altering the pharmacokinetics or tissue distribution of the oligonucleotide. In certain embodiments, such modified antisense oligonucleotides comprise one or more modified nucleosides and/or one or more modified nucleoside linkages and/or one or more conjugate groups.

a. Certain Modified Nucleosides

In certain embodiments, antisense oligonucleotides comprise one or more modified nucleosides. Such modified nucleosides may include a modified sugar and/or a modified nucleobase. In certain embodiments, incorporation of such modified nucleosides in an oligonucleotide results in increased affinity for a target nucleic acid and/or increased stability, including but not limited to, increased resistance to nuclease degradation, and or improved toxicity and/or uptake properties of the modified oligonucleotide.

i. Certain Nucleobases

The naturally occurring base portion of nucleosides are heterocyclic base, typically purines and pyrimidines. In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable to incorporation into the compounds described herein. In certain embodiments, a modified nucleobase is a nucleobase that is fairly similar in structure to the parent nucleobase, such as for example a 7-deaza purine, a 5-methyl cytosine, or a G-clamp. In certain embodiments, nucleobase mimetic include more complicated structures, such as for example a tricyclic phenoxazine nucleobase mimetic. Methods for preparation of the above noted modified nucleobases are well known to those skilled in the art.

ii. Certain Modified Sugars and Sugar Surrogates

Antisense oligonucleotides of the present invention can optionally contain one or more nucleosides wherein the sugar moiety is modified, compared to a natural sugar. Oligonucleotides comprising such sugar modified nucleosides may have enhanced nuclease stability, increased binding affinity or some other beneficial biological property. Such modifications include without limitation, addition of substituent groups, bridging of non-geminal ring atoms to form a bicyclic nucleic acid (BNA), replacement of the ribosyl ring oxygen atom with S, N(R), or $C(R_1)(R)_2$ (R=H, $C_1$-$C_{12}$ alkyl or a protecting group) and combinations of these such as for example a 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $O(CH_2)_2SCH_3$, O—$(CH_2)_2$—O—N($R_m$)($R_n$), and O—$CH_2$—C(=O)—N($R_m$)($R_n$), where each $R_m$ and $R_n$ is, independently, H or substituted or unsubstituted $C_1$-$C_{10}$ alkyl.

Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-β-D-($CH_2$)—O-2' (β-D-LNA); 4'-($CH_2$)—S-2'; 4'-α-L-($CH_2$)—O-2' (α-L-LNA); 4'-($CH_2$)$_2$—O-2' (ENA); 4'-C($CH_3$)$_2$—O-2' (see PCT/US2008/068922); 4'-CH($CH_3$)—O-2' and 4'-C—H($CH_2OCH_3$)—O-2' (see U.S. Pat. No. 7,399,845, issued on Jul. 15, 2008); 4'-$CH_2$—N($OCH_3$)-2' (see PCT/US2008/064591); 4'-$CH_2$—O—N($CH_3$)-2' (see published U.S. Patent Application US2004-0171570, published Sep. 2, 2004); 4'-$CH_2$—N(R)—O-2' (see U.S. Pat. No. 7,427,672, issued on Sep. 23, 2008); 4'-$CH_2$—C($CH_3$)-2' and 4'-$CH_2$—C(=$CH_2$)-2' (see PCT/US2008/066154); and wherein R is, independently, H, $C_1$-$C_{12}$ alkyl, or a protecting group.

In certain embodiments, the present invention provides modified nucleosides comprising modified sugar moieties that are not bicyclic sugar moieties. Certain such modified nucleosides are known. In certain embodiments, the sugar ring of a nucleoside may be modified at any position. Examples of sugar modifications useful in this invention include, but are not limited to compounds comprising a sugar substituent group selected from: OH, F, O-alkyl, S-alkyl, N-alkyl, or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. In certain such embodiments, such substituents are at the 2' position of the sugar.

In certain embodiments, modified nucleosides comprise a substituent at the 2' position of the sugar. In certain embodiments, such substituents are selected from among: a halide (including, but not limited to F), allyl, amino, azido, thio, O-allyl, O—$C_1$-$C_{10}$ alkyl, —$OCF_3$, O—$(CH_2)_2$—O—$CH_3$, 2'-$O(CH_2)_2SCH_3$, O—$(CH_2)_2$—O—N($R_m$)($R_n$), or O—$CH_2$—C(=O)—N($R_m$)($R_n$), where each $R_m$ and $R_n$ is, independently, H or substituted or unsubstituted $C_1$-$C_{10}$ alkyl.

In certain embodiments, modified nucleosides suitable for use in the present invention are: 2-methoxyethoxy, 2'-O-methyl (2'-O—$CH_3$), 2'-fluoro (2'-F).

In certain embodiments, modified nucleosides having a substituent group at the 2'-position selected from: O[($CH_2$)$_n$O]$_m$$CH_3$, O($CH_2$)$_n$$NH_2$, O($CH_2$)$_n$$CH_3$, O($CH_2$)$_n$$ONH_2$, $OCH_2$C(=O)N(H)$CH_3$, and O($CH_2$)$_n$ON[($CH_2$)$_n$$CH_3$]$_2$, where n and m are from 1 to about 10. Other 2'-sugar sub stituent groups include: $C_1$ to $C_{10}$ alkyl, substituted alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an oligomeric compound, and other substituents having similar properties.

In certain embodiments, modified nucleosides comprise a 2'-MOE side chain (Baker et al., J. Biol. Chem., 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, P., Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926).

In certain embodiments, 2'-sugar substituent groups are in either the arabino (up) position or ribo (down) position. In certain such embodiments, a 2'-arabino modification is 2'-F arabino (FANA). Similar modifications can also be made at other positions on the sugar, particularly the 3' position of the sugar on a 3' terminal nucleoside or in 2'-5' linked oligonucleotides and the 5' position of 5' terminal nucleotide.

In certain embodiments, nucleosides suitable for use in the present invention have sugar surrogates such as cyclobutyl in place of the ribofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

In certain embodiments, the present invention provides nucleosides comprising a modification at the 2'-position of the sugar. In certain embodiments, the invention provides nucleosides comprising a modification at the 5'-position of the sugar. In certain embodiments, the invention provides nucleosides comprising modifications at the 2'-position and the 5'-position of the sugar. In certain embodiments, modified nucleosides may be useful for incorporation into oligonucleotides. In certain embodiment, modified nucleosides are incorporated into oligonucleosides at the 5'-end of the oligonucleotide.

b. Certain Internucleoside Linkages

Antisense oligonucleotides of the present invention can optionally contain one or more modified internucleoside linkages. The two main classes of linking groups are defined by the presence or absence of a phosphorus atom. Representative phosphorus containing linkages include, but are not limited to, phosphodiesters (P=O), phosphotriesters, methylphosphonates, phosphoramidate, and phosphorothioates (P=S). Representative non-phosphorus containing linking groups include, but are not limited to, methylenemethylimino (—CH2-N(CH3)-O—CH2-), thiodiester (—O—C(O)—S—), thionocarbamate (—O—C(O)(NH)—S—); siloxane (—O—Si(H)2-O—); and N,N'-dimethylhydrazine (—CH2-N(CH3)-N(CH3)-). Oligonucleotides having non-phosphorus linking groups are referred to as oligonucleosides. Modified linkages, compared to natural phosphodiester linkages, can be used to alter, typically increase, nuclease resistance of the oligonucleotides. In certain embodiments, linkages having a chiral atom can be prepared as racemic mixtures, as separate enantiomers. Representative chiral linkages include, but are not limited to, alkylphosphonates and phosphorothioates. Methods of preparation of phosphorous-containing and non-phosphorous-containing linkages are well known to those skilled in the art.

The antisense oligonucleotides described herein contain one or more asymmetric centers and thus give rise to enantiomers, diastereomers, and other stereoisomeric configurations that may be defined, in terms of absolute stereochemistry, as (R) or (S), such as for sugar anomers, or as (D) or (L) such as for amino acids et al. Included in the antisense compounds provided herein are all such possible isomers, as well as their racemic and optically pure forms.

In certain embodiments, antisense oligonucleotides have at least one modified internucleoside linkage. In certain embodiments, antisense oligonucleotides have at least 2 modified internucleoside linkages. In certain embodiments, antisense oligonucleotides have at least 3 modified internucleoside linkages. In certain embodiments, antisense oligonucleotides have at least 10 modified internucleoside linkages. In certain embodiments, each internucleoside linkage of an antisense oligonucleotide is a modified internucleoside linkage. In certain embodiments, such modified internucleoside linkages are phosphorothioate linkages.

c. Lengths

In certain embodiments, the present invention provides antisense oligonucleotides of any of a variety of ranges of lengths. In certain embodiments, the invention provides antisense compounds or antisense oligonucleotides comprising or consisting of X-Y linked nucleosides, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides antisense compounds or antisense oligonucleotides comprising or consisting of: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-29, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked nucleosides.

In certain embodiments, antisense compounds or antisense oligonucleotides of the present invention are 15 nucleosides in length. In certain embodiments, antisense compounds or antisense oligonucleotides of the present invention are 16 nucleosides in length. In certain embodiments, antisense compounds or antisense oligonucleotides of the present invention are 17 nucleosides in length. In certain embodiments, antisense compounds or antisense oligonucleotides of the present invention are 18 nucleosides in length. In certain embodiments, antisense compounds or antisense oligonucleotides of the present invention are 19 nucleosides in length. In certain embodiments, antisense compounds or antisense oligonucleotides of the present invention are 20 nucleosides in length.

d. Certain Oligonucleotide Motifs

In certain embodiments, antisense oligonucleotides have chemically modified subunits arranged in specific orientations along their length. In certain embodiments, antisense oligonucleotides of the invention are fully modified. In certain embodiments, antisense oligonucleotides of the invention are uniformly modified. In certain embodiments, antisense oligonucleotides of the invention are uniformly modified and each nucleoside comprises a 2'-MOE sugar moiety. In certain embodiments, antisense oligonucleotides of the invention are uniformly modified and each nucleoside comprises a 2'-OMe sugar moiety. In certain embodiments, antisense oligonucleotides of the invention are uniformly modified and each nucleoside comprises a morpholino sugar moiety.

In certain embodiments, oligonucleotides of the invention comprise an alternating motif. In certain such embodiments, the alternating modification types are selected from among 2'-MOE, 2'-F, a bicyclic sugar-modified nucleoside, and DNA (unmodified 2'-deoxy). In certain such embodiments, each alternating region comprises a single nucleoside.

In certain embodiments, oligonucleotides of the invention comprise one or more block of nucleosides of a first type and one or more block of nucleosides of a second type.

In certain embodiments, one or more alternating regions in an alternating motif include more than a single nucleoside of a type. For example, oligomeric compounds of the present invention may include one or more regions of any of the following nucleoside motifs:

$Nu_1$ $Nu_1$ $Nu_2$ $Nu_2$ $Nu_1$ $Nu_1$;
$Nu_1$ $Nu_2$ $Nu_2$ $Nu_1$ $Nu_2$ $Nu_2$;
$Nu_1$ $Nu_1$ $Nu_2$ $Nu_1$ $Nu_1$ $Nu_2$;
$Nu_1$ $Nu_2$ $Nu_2$ $Nu_1$ $Nu_2$ $Nu_1$ $Nu_1$ $Nu_2$ $Nu_2$;
$Nu_1$ $Nu_2$ $Nu_1$ $Nu_2$ $Nu_1$ $Nu_1$;
$Nu_1$ $Nu_1$ $Nu_2$ $Nu_1$ $Nut$ $Nu_1$ $Nu_2$;
$Nu_1$ $Nu_2$ $Nu_1$ $Nu_2$ $Nu_1$ $Nu_1$;
$Nu_1$ $Nu_2$ $Nu_2$ $Nu_1$ $Nu_1$ $Nu_2$ $Nu_2$ $Nu_1$ $Nu_2$ $Nu_1$ $Nu_2$ $Nu_1$ $Nu_1$;
$Nu_2$ $Nu_1$ $Nu_2$ $Nu_2$ $Nu_1$ $Nu_1$ $Nu_2$ $Nu_2$ $Nu_1$ $Nu_2$ $Nui Nu_2$ $Nu_1$ $Nu_1$; or
$Nu_1$ $Nu_2$ $Nu_1$ $Nu_2$ $Nu_2$ $Nu_1$ $Nu_1$ $Nu_2$ $Nu_2$ $Nu_1$ $Nu_2$ $Nu_1$ $Nu_2$ $Nu_1$ $Nu_1$;

wherein $Nu_1$ is a nucleoside of a first type and $Nu_2$ is a nucleoside of a second type. In certain embodiments, one of $Nu_1$ and $Nu_2$ is a 2'-MOE nucleoside and the other of $Nu_1$ and $Nu_2$ is a selected from: a 2'-OMe modified nucleoside, BNA, and an unmodified DNA or RNA nucleoside.

2. Oligomeric Compounds

In certain embodiments, the present invention provides oligomeric compounds. In certain embodiments, oligomeric compounds are comprised only of an oligonucleotide. In certain embodiments, an oligomeric compound comprises an oligonucleotide and one or more conjugate and/or terminal group. Such conjugate and/or terminal groups may be added to oligonucleotides having any of the chemical motifs discussed above. Thus, for example, an oligomeric compound comprising an oligonucleotide having region of alternating nucleosides may comprise a terminal group.

a. Certain Conjugate Groups

In certain embodiments, oligonucleotides of the present invention are modified by attachment of one or more conjugate groups. In general, conjugate groups modify one or more properties of the attached oligomeric compound including but not limited to, pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130.

Representative U.S. patents that teach the preparation of oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Conjugate groups may be attached to either or both ends of an oligonucleotide (terminal conjugate groups) and/or at any internal position.

b. Terminal Groups

In certain embodiments, oligomeric compounds comprise terminal groups at one or both ends. In certain embodiments, a terminal group may comprise any of the conjugate groups discussed above. In certain embodiments, terminal groups may comprise additional nucleosides and/or inverted abasic nucleosides. In certain embodiments, a terminal group is a stabilizing group.

In certain embodiments, oligomeric compounds comprise one or more terminal stabilizing group that enhances properties such as for example nuclease stability. Included in stabilizing groups are cap structures. The terms "cap structure" or "terminal cap moiety," as used herein, refer to chemical modifications, which can be attached to one or both of the termini of an oligomeric compound. Certain such terminal modifications protect the oligomeric compounds having terminal nucleic acid moieties from exonuclease degradation, and can help in delivery and/or localization within a cell. The cap can be present at the 5'-terminus (5'-cap) or at the 3'-terminus (3'-cap) or can be present on both termini. (for more details see Wincott et al., International PCT publication No. WO 97/26270; Beaucage and Tyer, 1993, Tetrahedron 49, 1925; U.S. Patent Application Publication No. US 2005/0020525; and WO 03/004602.

In certain embodiments, one or more additional nucleosides is added to one or both terminal ends of an oligonucleotide of an oligomeric compound. Such additional terminal nucleosides are referred to herein as terminal-group nucleosides. In a double-stranded compound, such terminal-group nucleosides are terminal (3' and/or 5') overhangs. In the setting of double-stranded antisense compounds, such terminal-group nucleosides may or may not be complementary to a target nucleic acid. In certain embodiments, the terminal group is a non-nucleoside terminal group. Such non-terminal groups may be any terminal group other than a nucleoside.

3. Antisense

In certain embodiments, oligomeric compounds of the present invention are antisense compounds. Accordingly, in such embodiments, oligomeric compounds hybridize with a target nucleic acid, resulting in an antisense activity.

a. Hybridization

In certain embodiments, the invention provides antisense compounds that specifically hybridize to a target nucleic acid when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

Thus, "stringent hybridization conditions" or "stringent conditions" means conditions under which an antisense compounds hybridize to a target sequence, but to a minimal number of other sequences. Stringent conditions are sequence-dependent and will be different in different circumstances, and "stringent conditions" under which antisense oligonucleotides hybridize to a target sequence are determined by the nature and composition of the antisense oligonucleotides and the assays in which they are being investigated.

It is understood in the art that incorporation of nucleotide affinity modifications may allow for a greater number of mismatches compared to an unmodified compound. Similarly, certain nucleobase sequences may be more tolerant to mismatches than other nucleobase sequences. One of ordinary skill in the art is capable of determining an appropriate number of mismatches between oligonucleotides, or between an antisense oligonucleotide and a target nucleic acid, such as by determining melting temperature (Tm). Tm or ΔTm can be calculated by techniques that are familiar to one of ordinary skill in the art. For example, techniques described in Freier et al. (Nucleic Acids Research, 1997, 25, 22: 4429-4443) allow one of ordinary skill in the art to evaluate nucleotide modifications for their ability to increase the melting temperature of an RNA:DNA duplex.

b. pre-mRNA Processing

In certain embodiments, antisense compounds provided herein are complementary to a pre-mRNA. In certain embodiments, such antisense compounds alter splicing of the pre-mRNA. In certain such embodiments, the ratio of one variant of a mature mRNA corresponding to a target pre-mRNA to another variant of that mature mRNA is altered. In certain such embodiments, the ratio of one variant of a protein expressed from the target pre-mRNA to another variant of the protein is altered. Certain oligomeric compounds and nucleobase sequences that may be used to alter splicing of a pre-mRNA may be found for example in U.S. Pat. Nos. 6,210,892; 5,627,274; 5,665,593; 5,916,808; 5,976,879; US2006/0172962; US2007/002390; US2005/0074801; US2007/0105807; US2005/0054836; WO 2007/090073; WO2007/047913, Hua et al., PLoS Biol 5(4):e73; Vickers et al., J. Immunol. 2006 Mar. 15; 176(6):3652-61; and Hua et al., American J. of Human Genetics (April 2008) 82, 1-15, each of which is hereby incorporated by reference in its entirety for any purpose. In certain embodiments antisense sequences that alter splicing are modified according to motifs of the present invention.

Antisense is an effective means for modulating the expression of one or more specific gene products and is uniquely useful in a number of therapeutic, diagnostic, and research applications. Provided herein are antisense compounds useful for modulating gene expression via antisense mechanisms of action, including antisense mechanisms based on target occupancy. In one aspect, the antisense compounds provided herein modulate splicing of a target gene. Such modulation includes promoting or inhibiting exon inclusion. Further provided herein are antisense compounds targeted to cis splicing regulatory elements present in pre-mRNA molecules, including exonic splicing enhancers, exonic splicing silencers, intronic splicing enhancers and intronic splicing silencers. Disruption of cis splicing regulatory elements is thought to alter splice site selection, which may lead to an alteration in the composition of splice products.

Processing of eukaryotic pre-mRNAs is a complex process that requires a multitude of signals and protein factors to achieve appropriate mRNA splicing. Exon definition by the spliceosome requires more than the canonical splicing signals which define intron-exon boundaries. One such additional signal is provided by cis-acting regulatory enhancer and silencer sequences. Exonic splicing enhancers (ESE), exonic splicing silencers (ESS), intronic splicing enhancers (ISE) and intron splicing silencers (NS) have been identified which either repress or enhance usage of splice donor sites or splice acceptor sites, depending on their site and mode of action (Yeo et al. 2004, Proc. Natl. Acad. Sci. U.S.A. 101(44):15700-15705). Binding of specific proteins (trans factors) to these regulatory sequences directs the splicing process, either promoting or inhibiting usage of particular splice sites and thus modulating the ratio of splicing products (Scamborova et al. 2004, Mol. Cell. Biol. 24(5):1855-1869; Hovhannisyan and Carstens, 2005, Mol. Cell. Biol. 25(1):250-263; Minovitsky et al. 2005, Nucleic Acids Res. 33(2):714-724).

4. Pharmaceutical Compositions

In certain embodiments, the present invention provides pharmaceutical compositions comprising one or more antisense compound. In certain embodiments, such pharmaceutical composition comprises a sterile saline solution and one or more antisense compound. In certain embodiments, such pharmaceutical composition consists of a sterile saline solution and one or more antisense compound.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments antisense compounds, can be utilized in pharmaceutical compositions by combining such oligomeric compounds with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in certain embodiments, employed in the methods described herein is a pharmaceutical composition comprising an antisense compound and a pharmaceutically acceptable diluent. In certain embodiments, the pharmaceutically acceptable diluent is PBS. In certain embodiments, the pharmaceutically acceptable diluent is artificial CSF.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid-based vectors have been used in nucleic acid therapies in a variety of methods. For example, in one method, the nucleic acid is introduced into preformed liposomes or lipoplexes made of mixtures of cationic lipids and neutral lipids. In another method, DNA complexes with mono- or poly-cationic lipids are formed without the presence of a neutral lipid.

Certain preparations are described in Akinc et al., *Nature Biotechnology* 26, 561-569 (1 May 2008), which is herein incorporated by reference in its entirety.

In certain embodiments, the pharmaceutically acceptable diluent is artificial CSF. In certain embodiments, artificial CSF is commercially available. In certain embodiments, artificial CSF is prepared according to a formulation provided by Harvard Apparatus, Inc. In certain embodiments, each 1 mL of artificial CSF contains the following ingredients:

| Ingredients | Grade | Quantity/ml |
| --- | --- | --- |
| Sodium dihydrogen phosphate dihydrate | USP, Ph. Eur. | 0.050 mg |
| Sodium phosphate dibasic anhydrous | USP, Ph. Eur. | 0.097 mg |
| Sodium chloride | USP, Ph. Eur. | 8.766 mg |
| Potassium chloride | USP, Ph. Eur. | 0.224 mg |
| Calcium chloride dihydrate | USP, Ph. Eur. | 0.206 mg |
| Magnesium chloride hexahydrate | USP, Ph. Eur. | 0.163 mg |
| Sodium hydroxide | NF, Ph. Eur. | As needed |
| Hydrochloric acid | NF, Ph. Eur. | As needed |
| Water for Injection | USP/Ph. Eur. | Q.S. |

In certain embodiments, the artificial CSF formulation vehicle comprises 1 mM phosphate buffer at pH 7.2, adequate sodium chloride to be isotonic, and physiological levels of electrolytes (e.g. potassium, calcium, and magnesium).

5. Certain Methods of Calculating the Amount of CSF Protein in a Subject

In certain embodiments, the present disclosure provides methods comprising measuring the amount of SMN protein in the cerebrospinal fluid of a subject. In certain embodiments, the subject has SMA. In certain embodiments, the method of determining the amount of SMN protein in a biological sample, e.g. cerebrospinal fluid, comprises (a) collecting a biological sample from a subject (e.g. cerebrospinal fluid), (b) contacting the biological sample with a capture antibody, (c) contacting the biological sample with a detection antibody, and (d) measuring the amount of detection antibody in the biological sample and calculating the amount of SMN protein in the biological sample.

In certain embodiments, the present disclosure provides a method of determining the amount of SMN protein in a biological sample comprising: (a) collecting a biological sample from a subject; (b) contacting the biological sample with a capture antibody; (c) contacting the biological sample with a detection antibody; (d) measuring the amount of detection antibody in the biological sample; and (e) calculating the amount of SMN protein in the biological sample.

6. Administration to a Subject

In certain embodiments, pharmaceutical compositions comprising one or more antisense compound are administered to a subject. In certain embodiments, such pharmaceutical compositions are administered by injection. In certain embodiments, such pharmaceutical compositions are administered by infusion.

In certain embodiments, pharmaceutical compositions are administered by injection or infusion into the CSF. In certain such embodiments, pharmaceutical compositions are administered by direct injection or infusion into the spine. In certain embodiments, pharmaceutical compositions are administered by injection or infusion into the brain. In certain embodiments, pharmaceutical compositions are administered by intrathecal injection or infusion rather than into the spinal cord tissue itself. Without being limited as to theory, in certain embodiments, the antisense compound released into the surrounding CSF and may penetrate into the spinal cord parenchyma. An additional advantage of intrathecal delivery is that the intrathecal route mimics lumbar puncture administration (i.e., spinal tap) already in routine use in humans.

In certain embodiments, pharmaceutical compositions are administered by intracerebroventricular (ICV) injection or infusion. Intracerebroventricular, or intraventricular, delivery of a pharmaceutical composition comprising one or more antisense compounds may be performed in any one or more of the brain's ventricles, which are filled with cerebrospinal fluid (CSF). CSF is a clear fluid that fills the ventricles, is present in the subarachnoid space, and surrounds the brain and spinal cord. CSF is produced by the choroid plexuses and via the weeping or transmission of tissue fluid by the brain into the ventricles. The choroid plexus is a structure lining the floor of the lateral ventricle and the roof of the third and fourth ventricles. Certain studies have indicated that these structures are capable of producing 400-600 ccs of fluid per day consistent with an amount to fill the central nervous system spaces four times in a day. In adult humans, the volume of this fluid has been calculated to be from 125 to 150 ml (4-5 oz). The CSF is in continuous formation, circulation and absorption. Certain studies have indicated that approximately 430 to 450 ml (nearly 2 cups) of CSF may be produced every day. Certain calculations estimate that production equals approximately 0.35 ml per minute in adults and 0.15 per minute in infant humans. The choroid plexuses of the lateral ventricles produce the majority of CSF. It flows through the foramina of Monro into the third ventricle where it is added to by production from the third ventricle and continues down through the aqueduct of Sylvius to the fourth ventricle. The fourth ventricle adds more CSF; the fluid then travels into the subarachnoid space through the foramina of Magendie and Luschka. It then circulates throughout the base of the brain, down around the spinal cord and upward over the cerebral hemispheres. The CSF empties into the blood via the arachnoid villi and intracranial vascular sinuses.

In certain embodiments, such pharmaceutical compositions are administered systemically. In certain embodiments, pharmaceutical compositions are administered subcutaneously. In certain embodiments, pharmaceutical compositions are administered intravenously. In certain embodiments, pharmaceutical compositions are administered by intramuscular injection.

In certain embodiments, pharmaceutical compositions are administered both directly to the CSF (e.g., IT and/or ICV injection and/or infusion) and systemically.

In certain embodiments, an antisense compound administered systemically enters neurons. In certain embodiments, systemically administered antisense compounds may penetrate the blood-brain barrier, particularly in young subjects where the blood-brain barrier is not fully formed (e.g., in subjects in eutero and/or in newborn subjects). In certain embodiments, some amount of systemically administered antisense compound may be taken up by nerve cells, even in subjects in which the blood-brain barrier is fully formed. For example, antisense compounds may enter a neuron at or near the neuromuscular junction (retrograde uptake). In certain embodiments, such retrograde uptake results in antisense activity inside the neuron, including, but not limited to, a motor neuron, and provides a therapeutic benefit by antisense activity inside the neuron.

In certain embodiments, systemic administration provides therapeutic benefit by antisense activity occurring in cells and/or tissues other than neurons. While evidence suggests that functional SMN inside neurons is required for normal neuron function, the consequence of reduced functional SMN in other cells and tissues is not well characterized. In certain embodiments, antisense activity in non-neuronal cells results in restoration of SMN function in those non-neuronal cells, which in turn results in therapeutic benefit.

In certain embodiments, improved SMN function in non-neuronal cells provides improved neuronal cell function, whether or not SMN function inside neurons is improved. For example, in certain embodiments, systemic administration of pharmaceutical compositions of the present invention results in antisense activity in muscle cells. Such antisense activity in muscle cells may provide a benefit to the motor-neurons associated with that muscle cell or to neurons generally. In such embodiments, the muscle cell having restored SMN function may provide a factor that improves neuronal viability and/or function. In certain embodiments, such antisense activity is independent of benefit from antisense activity occurring from antisense compounds inside neurons. In certain embodiments, systemic administration of pharmaceutical compositions of the present invention results in antisense activity in other non-neuronal cells, including cells not in immediate association with neurons. Such antisense activity in non-neuronal cells may improve function of neurons. For example, antisense activity in a non-neuronal cell (e.g., liver cell) may result in that cell producing a factor that improves function of neurons. Note: since the term "antisense activity" includes direct and indirect activities, a benefit to neuronal function is an "antisense activity" even if no antisense compound enters the neuron.

In certain embodiments, systemic administration of a pharmaceutical composition results in therapeutic benefit independent of direct or indirect antisense activities in neurons. Typically, in the setting of SMA, neuronal function is diminished, resulting in significant symptoms. Additional symptoms may result from diminished SMN activity in other cells. Certain such symptoms may be masked by the relative severity of symptoms from diminished neuronal function. In certain embodiments, systemic administration results in restored or improved SMN function in non-neuronal cells. In certain such embodiments, such restored or improved SMN function in non-neuronal cells has therapeutic benefit. For example, in certain instances, subjects having SMA have reduced growth. Such reduced growth may not result from diminished function in neuronal cells. Indeed, reduced growth may be related to impaired function of cells in another organ, such as the pituitary gland, and/or may be the result of SMN deficiencies throughout the cells of the body. In such embodiments, systemic administration may result in improved SMN activity in pituitary cells and/or other cells, resulting in improved growth. In certain instances, administration to the CSF restores sufficient neuronal function to allow a subject to live longer, however one or more symptoms previously unknown because subjects typically died before such symptoms appeared emerges, because the subject lives longer. Certain such emergent symptoms may be lethal. In certain embodiments, emergent symptoms are treated by systemic administration. Regardless of mechanism, in certain embodiments, a variety of symptoms of SMA, including, but not limited to symptoms previously masked by more severe symptoms associated with impaired neuronal function, may be treated by systemic administration.

In certain embodiments, systemic administration of pharmaceutical compositions of the present invention result in increased SMN activity in muscle cells. In certain embodiments, such improved SMN activity in muscle cells provides therapeutic benefit. Improved SMN activity in muscle alone has been reported to be insufficient to provide therapeutic benefit (e.g., Gravrilina, et al., Hum Mol Genet 2008 17(8): 1063-1075). In certain embodiments, the present invention provides methods that result improve SMN function in muscle and do provide therapeutic benefit. In certain instances, therapeutic benefit may be attributable to improved SMN function in other cells (alone or in combination with muscle cells). In certain embodiments, improved SMN function in muscle alone may provide benefit.

In certain embodiments, systemic administration results in improved survival.

7. Spinal Muscular Atrophy (SMA)

SMA is a genetic disorder characterized by degeneration of spinal motor neurons. SMA is caused by the homozygous loss of both functional copies of the SMN1 gene. However, the SMN2 gene has the potential to code for the same protein as SMN1 and thus overcome the genetic defect of SMA patients. SMN2 contains a translationally silent mutation (C→T) at position +6 of exon 7, which results in inefficient inclusion of exon 7 in SMN2 transcripts. Therefore, the predominant form of SMN2, one which lacks exon 7, is unstable and inactive. Thus, therapeutic compounds capable of modulating SMN2 splicing such that the percentage of SMN2 transcripts containing exon 7 is increased, would be useful for the treatment of SMA.

In certain embodiments, the present invention provides antisense compounds complementary to a pre-mRNA encoding SMN2. In certain such embodiments, the antisense compound alters splicing of SMN2. Certain sequences and regions useful for altering splicing of SMN2 may be found in PCT/US06/024469, which is hereby incorporated by reference in its entirety for any purpose. In certain embodiments, oligomeric compounds having any motif described herein have a nucleobase sequence complementary to intron 7 of SMN2. Certain such nucleobase sequences are exemplified in the non-limiting table below. In the nucleobase sequences exemplified in the non-limiting table below, all "C" residues represent 5-methylcytosines.

| Sequence | Length | SEQ ID NO |
|---|---|---|
| TGCTGGCAGACTTAC | 15 | 3 |
| CATAATGCTGGCAGA | 15 | 4 |
| TCATAATGCTGGCAG | 15 | 5 |
| TTCATAATGCTGGCA | 15 | 6 |
| TTTCATAATGCTGGC | 15 | 2 |
| ATTCACTTTCATAATGCTGG | 20 | 7 |
| TCACTTTCATAATGCTGG | 18 | 1 |
| CTTTCATAATGCTGG | 15 | 8 |
| TCATAATGCTGG | 12 | 9 |
| ACTTTCATAATGCTG | 15 | 10 |
| TTCATAATGCTG | 12 | 11 |
| CACTTTCATAATGCT | 15 | 12 |
| TTTCATAATGCT | 12 | 13 |
| TCACTTTCATAATGC | 15 | 14 |
| CTTTCATAATGC | 12 | 15 |
| TTCACTTTCATAATG | 15 | 16 |
| ACTTTCATAATG | 12 | 17 |
| ATTCACTTTCATAAT | 15 | 18 |
| CACTTTCATAAT | 12 | 19 |
| GATTCACTTTCATAA | 15 | 20 |
| TCACTTTCATAA | 12 | 21 |
| TTCACTTTCATA | 12 | 22 |
| ATTCACTTTCAT | 12 | 23 |
| AGTAAGATTCACTTT | 15 | 24 |

Antisense compounds of the present invention can be used to modulate the expression of SMN2 in a subject, such as a human. In certain embodiments, the subject has spinal muscular atrophy. In certain such subjects, the SMN1 gene is absent or otherwise fails to produce sufficient amounts of functional SMN protein. In certain embodiments, the antisense compounds of the present invention effectively modulate splicing of SMN2, resulting in an increase in exon 7 inclusion in SMN2 mRNA and ultimately in SMN2 protein that includes the amino acids corresponding to exon 7. Such alternate SMN2 protein resembles wild-type SMN protein. Antisense compounds of the present invention that effectively modulate expression of SMN2 mRNA or protein products of expression are considered active antisense compounds.

Modulation of expression of SMN2 can be measured in a bodily fluid, which may or may not contain cells; tissue; or organ of the animal. Methods of obtaining samples for analysis, such as body fluids (e.g., sputum, serum, CSF), tissues (e.g., biopsy), or organs, and methods of preparation of the samples to allow for analysis are well known to those skilled in the art. Methods for analysis of RNA and protein levels are discussed above and are well known to those skilled in the art. The effects of treatment can be assessed by measuring biomarkers associated with the target gene expression in the aforementioned fluids, tissues or organs, collected from an animal contacted with one or more compounds of the invention, by routine clinical methods known in the art.

Methods whereby bodily fluids, organs or tissues are contacted with an effective amount of one or more of the antisense compounds or compositions of the invention are also contemplated. Bodily fluids, organs or tissues can be contacted with one or more of the compounds of the invention resulting in modulation of SMN2 expression in the cells of bodily fluids, organs or tissues. An effective amount can be determined by monitoring the modulatory effect of the antisense compound or compounds or compositions on target nucleic acids or their products by methods routine to the skilled artisan.

The invention also provides an antisense compound as described herein, for use in any of the methods as described herein. For example, the invention provides an antisense compound comprising an antisense oligonucleotide complementary to a nucleic acid encoding human SMN2, for use in treating a disease or condition associated with survival motor neuron protein (SMN), such as spinal muscular atrophy (SMA). As a further example, the invention provides an antisense compound comprising an antisense oligonucleotide complementary to a nucleic acid encoding human SMN2, for use in treating a disease or condition associated with survival motor neuron protein (SMN) by administering the antisense compound directly into the central nervous system (CNS) or CSF.

The invention also provides the use of an antisense compound as described herein in the manufacture of a medicament for use in any of the methods as described herein. For example, the invention provides the use of an antisense compound comprising an antisense oligonucleotide complementary to a nucleic acid encoding human SMN2 in the manufacture of a medicament for treating a disease or condition associated with survival motor neuron protein (SMN), such as spinal muscular atrophy (SMA). As a further example, the invention provides the use of an antisense compound comprising an antisense oligonucleotide complementary to a nucleic acid encoding human SMN2 in the manufacture of a medicament for treating a disease or condition associated with survival motor neuron protein (SMN) by administration of the medicament directly into the central nervous system (CNS) or CSF.

In certain embodiments, oligomeric compounds having any motif described herein have a nucleobase sequence complementary to exon 7 of SMN2.

In certain embodiments, oligomeric compounds having any motif described herein have a nucleobase sequence complementary to intron 6 of SMN2.

In certain embodiments, an antisense compound comprises an antisense oligonucleotide having a nucleobase sequence comprising at least 10 nucleobases of the sequence: TCACTTTCATAATGCTGG (SEQ ID NO: 1). In certain embodiments, an antisense oligonucleotide has a nucleobase sequence comprising at least 11 nucleobases of such sequence. In certain embodiments, an antisense oligonucleotide has a nucleobase sequence comprising at least 12 nucleobases of such sequence. In certain embodiments, an antisense oligonucleotide has a nucleobase sequence comprising at least 13 nucleobases of such sequence. In certain embodiments, an antisense oligonucleotide has a nucleobase sequence comprising at least 14 nucleobases of such sequence. In certain embodiments, an antisense oligonucleotide has a nucleobase sequence comprising at least 15 nucleobases of such sequence. In certain embodiments, an antisense oligonucleotide has a nucleobase sequence comprising at least 16 nucleobases of such sequence. In certain embodiments, an antisense oligonucleotide has a nucleobase sequence comprising at least 17 nucleobases of such sequence. In certain embodiments, an antisense oligonucleotide has a nucleobase sequence comprising the nucleobases of such sequence. In certain embodiments, an antisense oligonucleotide has a nucleobase sequence consisting of the nucleobases of such sequence. In certain embodiments, an antisense oligonucleotide consists of 10-18 linked nucleosides and has a nucleobase sequence 100% identical to an equal-length portion of the sequence: TCACTTTCATAATGCTGG (SEQ ID NO: 1).

8. Certain Subjects

In certain embodiments, a subject has one or more indicator of SMA. In certain embodiments, the subject has reduced electrical activity of one or more muscles. In certain embodiments, the subject has a mutant SMN1 gene. In certain embodiment, the subject's SMN1 gene is absent or incapable of producing functional SMN protein. In certain embodiments, the subject is diagnosed by a genetic test. In certain embodiments, the subject is identified by muscle biopsy. In certain embodiments, a subject is unable to sit upright. In certain embodiments, a subject is unable to stand or walk. In certain embodiments, a subject requires assistance to breathe and/or eat. In certain embodiment, a subject is identified by electrophysiological measurement of muscle and/or muscle biopsy.

In certain embodiments, the subject has SMA type I. In certain embodiments, the subject has SMA type II. In certain embodiments, the subject has SMA type III. In certain embodiments, the subject has SMA type IV. In certain embodiments, the subject is diagnosed as having SMA in utero. In certain embodiments, the subject is diagnosed as having SMA within one week after birth. In certain embodiments, the subject is diagnosed as having SMA within one month of birth. In certain embodiments, the subject is diagnosed as having SMA by 3 months of age. In certain embodiments, the subject is diagnosed as having SMA by 6 months of age. In certain embodiments, the subject is diagnosed as having SMA by 1 year of age. In certain embodiments, the subject is diagnosed as having SMA between 1 and 2 years of age. In certain embodiments, the subject is diagnosed as having SMA between 1 and 15 years of age. In certain embodiments, the subject is diagnosed as having SMA when the subject is older than 15 years of age.

In certain embodiments, the first dose of a pharmaceutical composition according to the present invention is administered in utero. In certain such embodiments, the first dose is administered before complete development of the blood-brain-barrier. In certain embodiments, the first dose is administered to the subject in utero systemically. In certain embodiments, the first dose is administered in utero after formation of the blood-brain-barrier. In certain embodiments, the first dose is administered to the CSF.

In certain embodiments, the first dose of a pharmaceutical composition according to the present invention is administered when the subject is less than one week old. In certain embodiments, the first dose of a pharmaceutical composition according to the present invention is administered when the subject is less than one month old. In certain embodiments, the first dose of a pharmaceutical composition according to the present invention is administered when the subject is less than 3 months old. In certain embodiments, the first dose of a pharmaceutical composition according to the present invention is administered when the subject is less than 6 months old. In certain embodiments, the first dose of a pharmaceutical composition according to the present invention is administered when the subject is less than one year old. In certain embodiments, the first dose of a pharmaceutical composition according to the present invention is administered when the subject is less than 2 years old. In certain embodiments, the first dose of a pharmaceutical composition according to the present invention is administered when the subject is less than 15 years old. In certain embodiments, the first dose of a pharmaceutical composition according to the present invention is administered when the subject is older than 15 years old.

9. Certain Doses

In certain embodiments, the present invention provides dose amounts and frequencies. In certain embodiments, pharmaceutical compositions are administered as a bolus injection.

In certain embodiments, pharmaceutical compositions are administered as a single IT bolus lumbar puncture injection. In certain embodiments, the IT bolus lumbar puncture injection target site for needle insertion is the L3/L4 space. In certain embodiments, the IT bolus lumbar puncture injection target site for needle insertion is the L3/L4 space but may be 1 segment above or 1-2 segments below this level, if needed. In certain embodiments, the volume of the IT bolus lumbar puncture injection is 5 mL. In certain embodiments, the volume of the IT bolus lumbar puncture injection is 1 mL. In certain embodiments, the volume of the IT bolus lumbar puncture injection is 2 mL. In certain embodiments, the volume of the IT bolus lumbar puncture injection is 3 mL. In certain embodiments, the volume of the IT bolus lumbar puncture injection is 4 mL. In certain embodiments, the volume of the IT bolus lumbar puncture injection is 6 mL. In certain embodiments, the volume of the IT bolus lumbar puncture injection is 7 mL. In certain embodiments, the volume of the IT bolus lumbar puncture injection is 8 mL. In certain embodiments, the volume of the IT bolus lumbar puncture injection is 9 mL. In certain embodiments, the volume of the IT bolus lumbar puncture injection is 10 mL. In certain embodiments, the volume of the IT bolus lumbar puncture injection is 4.3 mL. In certain embodiments, the volume of the IT bolus lumbar puncture injection is 4.5 mL.

10. Administration of Certain Doses

In certain embodiments, the dose is selected to produce a desired tissue concentration. In certain embodiments, the desired tissue is spinal cord tissue. In certain embodiments, the desired spinal cord tissue concentration is between 1 µ/g and 10 µ/g. In certain embodiments, the desired spinal cord tissue concentration is between 1 µ/g and 15 µ/g. In certain embodiments, the desired spinal cord tissue concentration is between 1 µ/g and 14 µ/g. In certain embodiments, the desired spinal cord tissue concentration is between 1 µ/g and 13 µ/g. In certain embodiments, the desired spinal cord tissue concentration is between 1 µ/g and 12 µ/g. In certain embodiments, the desired spinal cord tissue concentration is between 1 µ/g and 11 µ/g. In certain embodiments, the desired spinal cord tissue concentration is between 1 µ/g and 9 µ/g. In certain embodiments, the desired spinal cord tissue concentration is between 1 µ/g and 8 µ/g. In certain embodiments, the desired spinal cord tissue concentration is between 1 µ/g and 7 µ/g. In certain embodiments, the desired spinal cord tissue concentration is between 1 µ/g and 6 µ/g. In certain embodiments, the desired spinal cord tissue concentration is between 1 µ/g and 5 µ/g. In certain embodiments, the desired spinal cord tissue concentration is between 1 µ/g and 4 µ/g. In certain embodiments, the desired spinal cord tissue concentration is between 1 µ/g and 3 µ/g. In certain embodiments, the desired spinal cord tissue concentration is between 1 µ/g and 2 µ/g. In certain embodiments, the desired spinal cord tissue concentration is between 1 µ/g and 30 µ/g. In certain embodiments, the desired spinal cord tissue concentration is between 1 µ/g and 25 µ/g. In certain embodiments, the desired spinal cord tissue concentration is between 1 µ/g and 20 µ/g. In certain embodiments, the desired spinal cord tissue concentration is between 1 µ/g and 18 µ/g.

11. Adjustment of Certain Doses

In certain embodiments, the dose is selected to produce a desired SMN protein concentration in the CSF and subsequent doses may be selected to increase or decrease the concentration of SMN in the CSF. For example, in certain embodiments, a sample of CSF may be taken from a patient having SMA and the sample analyzed to calculate the amount of SMN protein according to methods described herein. After calculation of the amount of baseline SMN protein, the patient is given a dose of ISIS 396443. In certain embodiments, the dose given to the patient is 12 mg of ISIS 396443. After receipt of the first dose of ISIS 396443, the patient may receive a subsequent dose of ISIS 396443.

Before receipt of the subsequent dose of ISIS 396443, a second sample of CSF may be taken from the patient and analyzed according to the methods or kits provided herein in order to determine the amount of SMN protein. The amount of SMN protein in the CSF may then be compared from the first and second samples from this comparison subsequent dose frequency and amount may be adjusted. For example, if the amount of SMN protein present in the second sample is much greater than the amount of SMN protein in the first sample, the dose frequency for each subsequent dose of ISIS 396443 may be decreased. For example, if the amount of SMN protein present in the second sample is much greater than the amount of SMN protein in the first sample, the dose amount for each subsequent dose of ISIS 396443 may be decreased. For example, if the amount of SMN protein present in the second sample is much greater than the amount of SMN protein in the first sample, the dose frequency and dose amount for each subsequent dose of ISIS 396443 may be decreased. Alternatively, if the amount of SMN protein present in the second sample is not much greater than the amount of SMN protein in the first sample, the dose frequency for each subsequent dose of ISIS 396443 may be increased. If the amount of SMN protein present in the second sample is not much greater than the amount of SMN protein in the first sample, the dose amount for each subsequent dose of ISIS 396443 may be increased.

12. Certain Routes of Administration

In certain embodiments, a dose is administered as an intrathecal injection by lumbar puncture. In certain embodiments, a single dose is administered as an intrathecal injection by lumbar puncture. In certain embodiments, a single dose of ISIS 396443 is administered as an intrathecal injection by lumbar puncture. In certain embodiments, a single 0.1 to 15 milligram dose of ISIS 396443 is administered as an intrathecal injection by lumbar puncture. In certain embodiments, a single 1 milligram dose of ISIS 396443 is administered as an intrathecal injection by lumbar puncture. In certain embodiments, a single 2 milligram dose of ISIS 396443 is administered as an intrathecal injection by lumbar puncture. In certain embodiments, a single 3 milligram dose of ISIS 396443 is administered as an intrathecal injection by lumbar puncture. In certain embodiments, a single 4 milligram dose of ISIS 396443 is administered as an intrathecal injection by lumbar puncture. In certain embodiments, a single 5 milligram dose of ISIS 396443 is administered as an intrathecal injection by lumbar puncture. In certain embodiments, a single 6 milligram dose of ISIS 396443 is administered as an intrathecal injection by lumbar puncture. In certain embodiments, a single 7 milligram dose of ISIS 396443 is administered as an intrathecal injection by lumbar puncture. In certain embodiments, a single 8 milligram dose of ISIS 396443 is administered as an intrathecal injection by lumbar puncture. In certain embodiments, a single 9 milligram dose of ISIS 396443 is administered as an intrathecal injection by lumbar puncture. In certain embodiments, a single 10 milligram dose of ISIS 396443 is administered as an intrathecal injection by lumbar puncture. In certain embodiments, a single 11 milligram dose of ISIS 396443 is administered as an intrathecal injection by lumbar puncture. In certain embodiments, a single 12 milligram dose of ISIS 396443 is administered as an intrathecal injection by lumbar puncture. In certain embodiments, a single 13 milligram dose of ISIS 396443 is administered as an intrathecal injection by lumbar puncture. In certain embodiments, a single 14 milligram dose of ISIS 396443 is administered as an intrathecal injection by lumbar puncture. In certain embodiments, a single 15 milligram dose of ISIS 396443 is administered as an intrathecal injection by lumbar puncture.

In certain embodiments, a single 4.8 milligram dose of ISIS 396443 is administered as an intrathecal injection by lumbar puncture. In certain embodiments, a single 5.16 milligram dose of ISIS 396443 is administered as an intrathecal injection by lumbar puncture. In certain embodiments, a single 5.40 milligram dose of ISIS 396443 is administered as an intrathecal injection by lumbar puncture. In certain embodiments, a single 7.2 milligram dose of ISIS 396443 is administered as an intrathecal injection by lumbar puncture. In certain embodiments, a single 7.74 milligram dose of ISIS 396443 is administered as an intrathecal injection by lumbar puncture. In certain embodiments, a single 8.10 milligram dose of ISIS 396443 is administered as an intrathecal injection by lumbar puncture.

In certain embodiments, a single 9.6 milligram dose of ISIS 396443 is administered as an intrathecal injection by lumbar puncture. In certain embodiments, a single 10.32 milligram dose of ISIS 396443 is administered as an intrathecal injection by lumbar puncture. In certain embodiments, a single 10.80 milligram dose of ISIS 396443 is administered as an intrathecal injection by lumbar puncture. In certain embodiments, a single 11.30 milligram dose of ISIS 396443 is administered as an intrathecal injection by lumbar puncture. In certain embodiments, a single 12 milligram dose of ISIS 396443 is administered as an intrathecal injection by lumbar puncture. In certain embodiments, a single 12.88 milligram dose of ISIS 396443 is administered as an intrathecal injection by lumbar puncture. In certain embodiments, a single 13.5 milligram dose of ISIS 396443 is administered as an intrathecal injection by lumbar puncture. In certain embodiments, a single 14.13 milligram dose of ISIS 396443 is administered as an intrathecal injection by lumbar puncture.

In certain embodiments, a single 10 milligram dose of ISIS 396443 is administered as an intrathecal injection by lumbar puncture. In certain embodiments, a single 11 milligram dose of ISIS 396443 is administered as an intrathecal injection by lumbar puncture. In certain embodiments, a single 12 milligram dose of ISIS 396443 is administered as an intrathecal injection by lumbar puncture. In certain embodiments, a single 13 milligram dose of ISIS 396443 is administered as an intrathecal injection by lumbar puncture. In certain embodiments, a single 14 milligram dose of ISIS 396443 is administered as an intrathecal injection by lumbar puncture. In certain embodiments, a single 15 milligram dose of ISIS 396443 is administered as an intrathecal injection by lumbar puncture. In certain embodiments, a single 16 milligram dose of ISIS 396443 is administered as an intrathecal injection by lumbar puncture. In certain embodiments, a single 17 milligram dose of ISIS 396443 is administered as an intrathecal injection by lumbar puncture. In certain embodiments, a single 18 milligram dose of ISIS 396443 is administered as an intrathecal injection by lumbar puncture. In certain embodiments, a single 19 milligram dose of ISIS 396443 is administered as an intrathecal injection by lumbar puncture. In certain embodiments, a single 20 milligram dose of ISIS 396443 is administered as an intrathecal injection by lumbar puncture.

In certain embodiments, where a dose of ISIS 396443 is administered as an intrathecal injection by lumbar puncture the use of a smaller gauge needle may reduce or ameliorate one or more symptoms associated with a lumbar puncture procedure. In certain embodiments, symptoms associated with a lumbar puncture include, but are not limited to, post-lumbar puncture syndrome, headache, back pain, pyrexia, constipation, nausea, vomiting, and puncture site pain. In certain embodiments, use of a 24 or 25 gauge needle for the lumbar puncture reduces or ameliorates one or more post lumbar puncture symptoms. In certain embodiments, use of a 21, 22, 23, 24 or 25 gauge needle for the lumbar puncture reduces or ameliorates post-lumbar puncture syndrome, headache, back pain, pyrexia, constipation, nausea, vomiting, and/or puncture site pain.

13. Certain Dose Concentrations and Injection Volumes

In certain embodiments, an active drug product, e.g. ISIS 396443, is combined with one or more pharmaceutically acceptable excipients or diluents. In certain embodiments, an active drug product, e.g. ISIS 396443, is combined with an artificial CSF diluent. In certain embodiments, ISIS 396443 is combined with an artificial CSF diluent. In certain embodiments, the concentration of ISIS 396443 in an artificial CSF diluent is 0.5 mg of ISIS 396443 per mL of solution. In certain embodiments, the concentration of ISIS 396443 in an artificial CSF diluent is 0.6 mg of ISIS 396443 per mL of solution. In certain embodiments, the concentration of ISIS 396443 in an artificial CSF diluent is 0.7 mg of ISIS 396443 per mL of solution. In certain embodiments, the concentration of ISIS 396443 in an artificial CSF diluent is 0.8 mg of ISIS 396443 per mL of solution. In certain embodiments, the concentration of ISIS 396443 in an artificial CSF diluent is 0.9 mg of ISIS 396443 per mL of solution. In certain embodiments, the concentration of ISIS 396443 in an artificial CSF diluent is 1.0 mg of ISIS 396443 per mL of solution. In certain embodiments, the concentration of ISIS 396443 in an artificial CSF diluent is 1.1 mg of ISIS 396443 per mL of solution. In certain embodiments, the concentration of ISIS 396443 in an artificial CSF diluent is 1.2 mg of ISIS 396443 per mL of solution. In certain embodiments, the concentration of ISIS 396443 in an artificial CSF diluent is 1.3 mg of ISIS 396443 per mL of solution. In certain embodiments, the concentration of ISIS 396443 in an artificial CSF diluent is 1.4 mg of ISIS 396443 per mL of solution. In certain embodiments, the concentration of ISIS 396443 in an artificial CSF diluent is 1.5 mg of ISIS 396443 per mL of solution. In certain embodiments, the concentration of ISIS 396443 in an artificial CSF diluent is 2.4 mg of ISIS 396443 per mL of solution.

In certain embodiments, the concentration of ISIS 396443 in an artificial CSF diluent is 0.2 mg of ISIS 396443 per mL of solution and the injection volume is 5.0 mL. In certain embodiments, the concentration of ISIS 396443 in an artificial CSF diluent is 0.6 mg of ISIS 396443 per mL of solution and the injection volume is 5.0 mL. In certain embodiments, the concentration of ISIS 396443 in an artificial CSF diluent is 1.2 mg of ISIS 396443 per mL of solution and the injection volume is 5.0 mL. In certain embodiments, the concentration of ISIS 396443 in an artificial CSF diluent is 1.8 mg of ISIS 396443 per mL of solution and the injection volume is 5.0 mL. In certain embodiments, the concentration of ISIS 396443 in an artificial CSF diluent is 2.0 mg of ISIS 396443 per mL of solution and the injection volume is 5.0 mL. In certain embodiments, the concentration of ISIS 396443 in an artificial CSF diluent is 2.4 mg of ISIS 396443 per mL of solution and the injection volume is 4.0 mL. In certain embodiments, the concentration of ISIS 396443 in an artificial CSF diluent is 2.4 mg of ISIS 396443 per mL of solution and the injection volume is 4.3 mL. In certain embodiments, the concentration of ISIS 396443 in an artificial CSF diluent is 2.4 mg of ISIS 396443 per mL of solution and the injection volume is 4.5 mL. In certain embodiments, the concentration of ISIS 396443 in an artificial CSF diluent is 2.4 mg of ISIS 396443 per mL of solution and the injection volume is 4.7 mL.

In certain embodiments, the concentration of ISIS 396443 in an artificial CSF diluent is 3 mg of ISIS 396443 per mL of solution and the injection volume is 4.0 mL. In certain embodiments, the concentration of ISIS 396443 in an artificial CSF diluent is 3 mg of ISIS 396443 per mL of solution and the injection volume is 4.3 mL. In certain embodiments, the concentration of ISIS 396443 in an artificial CSF diluent is 3 mg of ISIS 396443 per mL of solution and the injection volume is 4.5 mL. In certain embodiments, the concentration of ISIS 396443 in an artificial CSF diluent is 3 mg of ISIS 396443 per mL of solution and the injection volume is 4.7 mL.

In certain embodiments, a dose equivalent of ISIS 396443 is calculated based on a patient's age or weight. For example, in certain embodiments a dose may be 6 mg and the dose equivalent may be greater than 6 mg or less than 6 mg.

In certain embodiments, the dose and/or the volume of the injection will be adjusted based on the patient's age. In certain embodiments, the dose and/or the volume of the injection will be adjusted based on the patient's CSF volume. In certain embodiments, the dose and/or the volume of the injection will be adjusted based on the patient's age and/or estimated CSF volume. In certain embodiments, the volume of the injection is adjusted such that each patient will receive a 6 mg or 9 mg equivalent dose based on CSF volume scaling. (For example, see Matsuzawa J, Matsui M, Konishi T, Noguchi K, Gur R C, Bilker W, Miyawaki T. Age-related volumetric changes of brain gray and white matter in healthy infants and children. Cereb Cortex 2001 April; 11(4):335-342, which is hereby incorporated by reference in its entirety). In certain embodiments, the volume of the injection is adjusted such that each patient will receive a 12 mg equivalent dose based on CSF volume scaling. (For example, see Matsuzawa J, Matsui M, Konishi T, Noguchi K, Gur R C, Bilker W, Miyawaki T. Age-related volumetric changes of brain gray and white matter in healthy infants and children. Cereb Cortex 2001 April; 11(4):335-342, which is hereby incorporated by reference in its entirety).

14. Certain Dose Frequencies

In certain embodiments, multiple doses of ISIS 396443 are administered to a subject having one or more symptoms associated with SMA. In certain embodiments, two or more doses of ISIS 396443 are administered to a subject having one or more symptoms associated with SMA. In certain embodiments, three or more doses of ISIS 396443 are administered to a subject having one or more symptoms associated with SMA. In certain embodiments, multiple doses of ISIS 396443 are administered to a subject having one or more symptoms associated with SMA. In certain embodiments, multiple doses of ISIS 396443 are administered at the same interval to a subject having one or more symptoms associated with SMA. In certain embodiments, multiple doses of ISIS 396443 are administered at different intervals to a subject having one or more symptoms associated with SMA.

In certain embodiments, a first dose of ISIS 396443 is administered to a subject having one or more symptoms associated with SMA, a second dose of ISIS 396443 is administered 15 days after the first dose, a third dose of ISIS 396443 is administered 29 days after the first dose, a fourth dose of ISIS 396443 is administered 64 days after the first dose, a fifth dose of ISIS 396443 is administered 183 days after the first dose, and a sixth dose of ISIS 396443 is administered 302 days after the first dose.

In certain embodiments, doses of ISIS 396443 are administered at intervals to a subject having one or more symptoms associated with SMA. In certain embodiments, single doses of ISIS 396443 are administered at 15 day intervals to a subject having one or more symptoms associated with SMA. In certain embodiments, single doses of ISIS 396443 are administered at 29 day intervals to a subject having one or more symptoms associated with SMA. In certain embodiments, single doses of ISIS 396443 are administered at 85 day intervals to a subject having one or more symptoms associated with SMA.

In certain embodiments a first dose of ISIS 396443 is administered to a subject having one or more symptoms associated with SMA, and a second dose of ISIS 396443 is administered about 15 days after the first dose. In certain embodiments a first dose of ISIS 396443 is administered to a subject having one or more symptoms associated with SMA, a second dose of ISIS 396443 is administered about 15 days after the first dose, and a third dose of ISIS 396443 is administered about 85 days after the first dose. In certain embodiments a first dose of ISIS 396443 is administered to a subject having one or more symptoms associated with SMA, a second dose of ISIS 396443 is administered about 15 days after the first dose, and a third dose of ISIS 396443 is administered about 29 days after the first dose.

In certain embodiments a first dose of ISIS 396443 is administered to a subject having one or more symptoms associated with SMA, a second dose of ISIS 396443 is administered about 15 days after the first dose, a third dose of ISIS 396443 is administered about 29 days after the first dose, and a fourth dose of ISIS 396443 is administered about 211 days after the first dose.

In certain embodiments, single 3 mg doses of ISIS 396443 are administered at 15 day intervals to a subject having one or more symptoms associated with SMA. In certain embodiments, single 3 mg doses of ISIS 396443 are administered at 29 day intervals to a subject having one or more symptoms associated with SMA. In certain embodiments, single 6 mg doses of ISIS 396443 are administered at 85 day intervals to a subject having one or more symptoms associated with SMA.

In certain embodiments, single 9 mg doses of ISIS 396443 are administered at 29 day intervals to a subject having one or more symptoms associated with SMA. In certain embodiments, single 9 mg doses of ISIS 396443 are administered at 85 day intervals to a subject having one or more symptoms associated with SMA.

In certain embodiments, a first dose of ISIS 396443 is administered to a subject having one or more symptoms associated with SMA and a second dose of ISIS 396443 is administered 15 days after the first dose. In certain embodiments, a first dose of ISIS 396443 is administered to a subject having one or more symptoms associated with SMA and a second dose of ISIS 396443 is administered 29 days after the first dose. In certain embodiments, a first dose of ISIS 396443 is administered to a subject having one or more symptoms associated with SMA and a second dose of ISIS 396443 is administered about 1 month after the first dose. In certain embodiments, a first dose of ISIS 396443 is administered to a subject having one or more symptoms associated with SMA and a second dose of ISIS 396443 is administered about 4 weeks after the first dose. In certain embodiments, a first dose of ISIS 396443 is administered to a subject having one or more symptoms associated with SMA and a second dose of ISIS 396443 is administered 29 days after the first dose, and a third dose of ISIS 396443 is administered 85 days after the first dose. In certain embodiments, a first dose of ISIS 396443 is administered to a subject having one or more symptoms associated with SMA and a second dose of ISIS 396443 is administered 85 days after the first dose. In certain embodiments, a first dose of ISIS 396443 is administered to a subject having one or more symptoms associated with SMA and a second dose of ISIS 396443 is administered 85 days after the first dose. In certain embodiments, the first dose and the second dose are the same amount. In certain embodiments, the first dose and the second dose are different amounts. In certain embodiments, the first, second, and third dose are the same amount. In certain embodiments, the first, second, and third dose are different amounts.

In certain embodiments, a first dose of 3 mg of ISIS 396443 is administered to a subject having one or more symptoms associated with SMA, a second dose of 3 mg of ISIS 396443 is administered 29 days after the first dose, and a third dose of 3 mg of ISIS 396443 is administered 85 days after the first dose. In certain embodiments, a first dose of 6 mg of ISIS 396443 is administered to a subject having one or more symptoms associated with SMA, a second dose of 6 mg of ISIS 396443 is administered 29 days after the first dose, and a third dose of 6 mg of ISIS 396443 is administered 85 days after the first dose. In certain embodiments, a first dose of 9 mg of ISIS 396443 is administered to a subject having one or more symptoms associated with SMA, a second dose of 9 mg of ISIS 396443 is administered 29 days after the first dose, and a third dose of 9 mg of ISIS 396443 is administered 85 days after the first dose. In certain embodiments, a first dose of 12 mg of ISIS 396443 is administered to a subject having one or more symptoms associated with SMA, a second dose of 12 mg of ISIS 396443 is administered 29 days after the first dose, and a third dose of 12 mg of ISIS 396443 is administered 85 days after the first dose. In certain embodiments, a first dose of 15 mg of ISIS 396443 is administered to a subject having one or more symptoms associated with SMA, a second dose of 15 mg of ISIS 396443 is administered 29 days after the first dose, and a third dose of 15 mg of ISIS 396443 is administered 85 days after the first dose.

In certain embodiments, a first dose of 3 mg of ISIS 396443 is administered to a subject having one or more symptoms associated with SMA, a second dose of 3 mg of ISIS 396443 is administered 15 days after the first dose, and a third dose of 3 mg of ISIS 396443 is administered 85 days after the first dose. In certain embodiments, a first dose of 6 mg of ISIS 396443 is administered to a subject having one or more symptoms associated with SMA, a second dose of 6 mg of ISIS 396443 is administered 15 days after the first dose, and a third dose of 6 mg of ISIS 396443 is administered 85 days after the first dose. In certain embodiments, a first dose of 9 mg of ISIS 396443 is administered to a subject having one or more symptoms associated with SMA, a second dose of 9 mg of ISIS 396443 is administered 15 days after the first dose, and a third dose of 9 mg of ISIS 396443 is administered 85 days after the first dose. In certain embodiments, a first dose of 12 mg of ISIS 396443 is administered to a subject having one or more symptoms associated with SMA, a second dose of 12 mg of ISIS 396443 is administered 15 days after the first dose, and a third dose of 12 mg of ISIS 396443 is administered 85 days after the first dose. In certain embodiments, a first dose of 15 mg of ISIS 396443 is administered to a subject having one or more symptoms associated with SMA, a second dose of 15 mg of ISIS 396443 is administered 15 days after the first dose, and a third dose of 15 mg of ISIS 396443 is administered 85 days after the first dose.

In certain embodiments, a first dose of 3 mg or equivalent of ISIS 396443 is administered to a subject having one or more symptoms associated with SMA, a second dose of 3 mg or equivalent of ISIS 396443 is administered 15 days after the first dose, and a third dose of 3 mg or equivalent of ISIS 396443 is administered 85 days after the first dose. In certain embodiments, a first dose of 6 mg or equivalent of ISIS 396443 is administered to a subject having one or more symptoms associated with SMA, a second dose of 6 mg or equivalent of ISIS 396443 is administered 15 days after the first dose, and a third dose of 6 mg or equivalent of ISIS 396443 is administered 85 days after the first dose. In certain embodiments, a first dose of 9 mg or equivalent of ISIS 396443 is administered to a subject having one or more symptoms associated with SMA, a second dose of 9 mg or equivalent of ISIS 396443 is administered 15 days after the first dose, and a third dose of 9 mg or equivalent of ISIS 396443 is administered 85 days after the first dose. In certain embodiments, a first dose of 12 mg or equivalent of ISIS 396443 is administered to a subject having one or more symptoms associated with SMA, a second dose of 12 mg or equivalent of ISIS 396443 is administered 15 days after the first dose, and a third dose of 12 mg or equivalent of ISIS 396443 is administered 85 days after the first dose. In certain embodiments, a first dose of 15 mg or equivalent of ISIS 396443 is administered to a subject having one or more symptoms associated with SMA, a second dose of 15 mg or equivalent of ISIS 396443 is administered 15 days after the first dose, and a third dose of 15 mg or equivalent of ISIS 396443 is administered 85 days after the first dose.

In certain embodiments, a first dose of 3 mg of ISIS 396443 is administered to a subject having one or more symptoms associated with SMA, and a second dose of 3 mg of ISIS 396443 is administered six months after the first dose, and a third dose of 3 mg of ISIS 396443 is administered 12 months after the first dose. In certain embodiments, a first dose of 6 mg of ISIS 396443 is administered to a subject having one or more symptoms associated with SMA, a second dose of 6 mg of ISIS 396443 is administered six months after the first dose, and a third dose of 6 mg of ISIS 396443 is administered 12 months after the first dose. In certain embodiments, a first dose of 9 mg of ISIS 396443 is administered to a subject having one or more symptoms associated with SMA, a second dose of 9 mg of ISIS 396443 is administered six months after the first dose, and a third dose of 9 mg of ISIS 396443 is administered 12 months after the first dose. In certain embodiments, a first dose of 12 mg of ISIS 396443 is administered to a subject having one or more symptoms associated with SMA, a second dose of 12 mg of ISIS 396443 is administered six months after the first dose, and a third dose of 12 mg of ISIS 396443 is administered 12 months after the first dose. In certain embodiments, a first dose of 15 mg of ISIS 396443 is administered to a subject having one or more symptoms associated with SMA, a second dose of 15 mg of ISIS 396443 is administered six months after the first dose, and a third dose of 15 mg of ISIS 396443 is administered 12 months after the first dose.

In certain embodiments, a first dose of 3 mg or equivalent of ISIS 396443 is administered to a subject having one or more symptoms associated with SMA, and a second dose of 3 mg or equivalent of ISIS 396443 is administered 12 months after the first dose. In certain embodiments, a first dose of 6 mg or equivalent of ISIS 396443 is administered to a subject having one or more symptoms associated with SMA, and a second dose of 6 mg or equivalent of ISIS 396443 is administered 12 months after the first dose. In certain embodiments, a first dose of 9 mg or equivalent of ISIS 396443 is administered to a subject having one or more symptoms associated with SMA, and a second dose of 9 mg or equivalent of ISIS 396443 is administered 12 months after the first dose. In certain embodiments, a first dose of 12 mg or equivalent of ISIS 396443 is administered to a subject having one or more symptoms associated with SMA, and a second dose of 12 mg or equivalent of ISIS 396443 is administered 12 months after the first dose. In certain embodiments, a first dose of 15 mg or equivalent of ISIS 396443 is administered to a subject having one or more symptoms associated with SMA, and a second dose of 15 mg or equivalent of ISIS 396443 is administered 12 months after the first dose.

In certain embodiments, a first dose of 3 mg or equivalent of ISIS 396443 is administered to a subject having one or more symptoms associated with SMA, and a second dose of 3 mg or equivalent of ISIS 396443 is administered 13 months after the first dose. In certain embodiments, a first dose of 6 mg or equivalent of ISIS 396443 is administered to a subject having one or more symptoms associated with SMA, and a second dose of 6 mg or equivalent of ISIS 396443 is administered 13 months after the first dose. In certain embodiments, a first dose of 9 mg or equivalent of ISIS 396443 is administered to a subject having one or more symptoms associated with SMA, and a second dose of 9 mg or equivalent of ISIS 396443 is administered 13 months after the first dose. In certain embodiments, a first dose of 12 mg or equivalent of ISIS 396443 is administered to a subject having one or more symptoms associated with SMA, and a second dose of 12 mg or equivalent of ISIS 396443 is administered 13 months after the first dose. In certain embodiments, a first dose of 15 mg or equivalent of ISIS 396443 is administered to a subject having one or more symptoms associated with SMA, and a second dose of 15 mg or equivalent of ISIS 396443 is administered 13 months after the first dose.

In certain embodiments, a first dose of 3 mg or equivalent of ISIS 396443 is administered to a subject having one or more symptoms associated with SMA, and a second dose of 3 mg or equivalent of ISIS 396443 is administered 14 months after the first dose. In certain embodiments, a first dose of 6 mg or equivalent of ISIS 396443 is administered to a subject having one or more symptoms associated with SMA, and a second dose of 6 mg or equivalent of ISIS 396443 is administered 14 months after the first dose. In certain embodiments, a first dose of 9 mg or equivalent of ISIS 396443 is administered to a subject having one or more symptoms associated with SMA, and a second dose of 9 mg or equivalent of ISIS 396443 is administered 14 months after the first dose. In certain embodiments, a first dose of 12 mg or equivalent of ISIS 396443 is administered to a subject having one or more symptoms associated with SMA, and a second dose of 12 mg or equivalent of ISIS 396443 is administered 14 months after the first dose. In certain embodiments, a first dose of 15 mg or equivalent of ISIS 396443 is administered to a subject having one or more symptoms associated with SMA, and a second dose of 15 mg or equivalent of ISIS 396443 is administered 14 months after the first dose.

In certain embodiments, a first dose of 3 mg or equivalent of ISIS 396443 is administered to a subject having one or more symptoms associated with SMA, and a second dose of 3 mg or equivalent of ISIS 396443 is administered 15 months after the first dose. In certain embodiments, a first dose of 6 mg or equivalent of ISIS 396443 is administered to a subject having one or more symptoms associated with SMA, and a second dose of 6 mg or equivalent of ISIS 396443 is administered 15 months after the first dose. In certain embodiments, a first dose of 9 mg or equivalent of ISIS 396443 is administered to a subject having one or more symptoms associated with SMA, and a second dose of 9 mg or equivalent of ISIS 396443 is administered 15 months after the first dose. In certain embodiments, a first dose of 12 mg or equivalent of ISIS 396443 is administered to a subject having one or more symptoms associated with SMA, and a second dose of 12 mg or equivalent of ISIS 396443 is administered 15 months after the first dose. In certain embodiments, a first dose of 15 mg or equivalent of ISIS 396443 is administered to a subject having one or more symptoms associated with SMA, and a second dose of 15 mg or equivalent of ISIS 396443 is administered 15 months after the first dose.

In certain embodiments, a first dose of 3 mg or equivalent of ISIS 396443 is administered to a subject having one or more symptoms associated with SMA, and subsequent doses of 3 mg or equivalent of ISIS 396443 are administered at 6 month intervals thereafter. In certain embodiments, a first dose of 6 mg or equivalent of ISIS 396443 is administered to a subject having one or more symptoms associated with SMA, and subsequent doses of 6 mg or equivalent of ISIS 396443 are administered at 6 month intervals thereafter. In certain embodiments, a first dose of 9 mg or equivalent of ISIS 396443 is administered to a subject having one or more symptoms associated with SMA, and subsequent doses of 9 mg or equivalent of ISIS 396443 are administered at 6 month intervals thereafter. In certain embodiments, a first dose of 12 mg or equivalent of ISIS 396443 is administered to a subject having one or more symptoms associated with SMA, and subsequent doses of 12 mg or equivalent of ISIS 396443 are administered at 6 month intervals thereafter. In certain embodiments, a first dose of 15 mg or equivalent of ISIS 396443 is administered to a subject having one or more symptoms associated with SMA, and subsequent doses of 15 mg or equivalent of ISIS 396443 are administered at 6 month intervals thereafter.

In certain embodiments, a first dose of 3 mg or equivalent of ISIS 396443 is administered to a subject having one or more symptoms associated with SMA, and subsequent doses of 3 mg or equivalent of ISIS 396443 are administered at 12 month intervals thereafter. In certain embodiments, a first dose of 6 mg or equivalent of ISIS 396443 is administered to a subject having one or more symptoms associated with SMA, and subsequent doses of 6 mg or equivalent of ISIS 396443 are administered at 12 month intervals thereafter. In certain embodiments, a first dose of 9 mg or equivalent of ISIS 396443 is administered to a subject having one or more symptoms associated with SMA, and subsequent doses of 9 mg or equivalent of ISIS 396443 are administered at 12 month intervals thereafter. In certain embodiments, a first dose of 12 mg or equivalent of ISIS 396443 is administered to a subject having one or more symptoms associated with SMA, and subsequent doses of 12 mg or equivalent of ISIS 396443 are administered at 12 month intervals thereafter. In certain embodiments, a first dose of 15 mg or equivalent of ISIS 396443 is administered to a subject having one or more symptoms associated with SMA, and subsequent doses of 15 mg or equivalent of ISIS 396443 are administered at 12 month intervals thereafter.

In certain embodiments, a first dose of 3 mg or equivalent of ISIS 396443 is administered to a subject having one or more symptoms associated with SMA, and subsequent doses of 3 mg or equivalent of ISIS 396443 are administered at 13 month intervals thereafter. In certain embodiments, a first dose of 6 mg or equivalent of ISIS 396443 is administered to a subject having one or more symptoms associated with SMA, and subsequent doses of 6 mg or equivalent of ISIS 396443 are administered at 13 month intervals thereafter. In certain embodiments, a first dose of 9 mg or equivalent of ISIS 396443 is administered to a subject having one or more symptoms associated with SMA, and subsequent doses of 9 mg or equivalent of ISIS 396443 are administered at 13 month intervals thereafter. In certain embodiments, a first dose of 12 mg or equivalent of ISIS 396443 is administered to a subject having one or more symptoms associated with SMA, and subsequent doses of 12 mg or equivalent of ISIS 396443 are administered at 13 month intervals thereafter. In certain embodiments, a first dose of 15 mg or equivalent of ISIS 396443 is administered to a subject having one or more symptoms associated with SMA, and subsequent doses of 15 mg or equivalent of ISIS 396443 are administered at 13 month intervals thereafter.

In certain embodiments, a first dose of 3 mg or equivalent of ISIS 396443 is administered to a subject having one or more symptoms associated with SMA, and subsequent doses of 3 mg or equivalent of ISIS 396443 are administered at 14 month intervals thereafter. In certain embodiments, a first dose of 6 mg or equivalent of ISIS 396443 is administered to a subject having one or more symptoms associated with SMA, and subsequent doses of 6 mg or equivalent of ISIS 396443 are administered at 14 month intervals thereafter. In certain embodiments, a first dose of 9 mg or equivalent of ISIS 396443 is administered to a subject having one or more symptoms associated with SMA, and subsequent doses of 9 mg or equivalent of ISIS 396443 are administered at 14 month intervals thereafter. In certain embodiments, a first dose of 12 mg or equivalent of ISIS 396443 is administered to a subject having one or more symptoms associated with SMA, and subsequent doses of 12 mg or equivalent of ISIS 396443 are administered at 14 month intervals thereafter. In certain embodiments, a first dose of 15 mg or equivalent of ISIS 396443 is administered to a subject having one or more symptoms associated with SMA, and subsequent doses of 15 mg or equivalent of ISIS 396443 are administered at 14 month intervals thereafter.

In certain embodiments, a first dose of 3 mg or equivalent of ISIS 396443 is administered to a subject having one or more symptoms associated with SMA, and subsequent doses of 3 mg or equivalent of ISIS 396443 are administered at 15 month intervals thereafter. In certain embodiments, a first dose of 6 mg or equivalent of ISIS 396443 is administered to a subject having one or more symptoms associated with SMA, and subsequent doses of 6 mg or equivalent of ISIS 396443 are administered at 15 month intervals thereafter. In certain embodiments, a first dose of 9 mg or equivalent of ISIS 396443 is administered to a subject having one or more symptoms associated with SMA, and subsequent doses of 9 mg or equivalent of ISIS 396443 are administered at 15 month intervals thereafter. In certain embodiments, a first dose of 12 mg or equivalent of ISIS 396443 is administered to a subject having one or more symptoms associated with SMA, and subsequent doses of 12 mg or equivalent of ISIS 396443 are administered at 15 month intervals thereafter. In certain embodiments, a first dose of 15 mg or equivalent of ISIS 396443 is administered to a subject having one or more symptoms associated with SMA, and subsequent doses of 15 mg or equivalent of ISIS 396443 are administered at 15 month intervals thereafter.

In certain embodiments, a first dose of 3 mg of ISIS 396443 is administered to a subject having one or more symptoms associated with SMA, a second dose of 3 mg of ISIS 396443 is administered 15 days after the first dose, a third dose of 3 mg of ISIS 396443 is administered 29 days after the first dose, and a fourth dose of 3 mg of ISIS 396443 is administered 211 days after the first dose. In certain embodiments, a first dose of 6 mg of ISIS 396443 is administered to a subject having one or more symptoms associated with SMA, a second dose of 6 mg of ISIS 396443 is administered 15 days after the first dose, a third dose of 6 mg of ISIS 396443 is administered 29 days after the first dose, and a fourth dose of 6 mg of ISIS 396443 is administered 211 days after the first dose. In certain embodiments, a first dose of 9 mg of ISIS 396443 is administered to a subject having one or more symptoms associated with SMA, a second dose of 9 mg of ISIS 396443 is administered 15 days after the first dose, a third dose of 9 mg of ISIS 396443 is administered 29 days after the first dose, and a fourth dose of 9 mg of ISIS 396443 is administered 211 days after the first dose. In certain embodiments, a first dose of 12 mg of ISIS 396443 is administered to a subject having one or more symptoms associated with SMA, a second dose of 12 mg of ISIS 396443 is administered 15 days after the first dose, a third dose of 12 mg of ISIS 396443 is administered 29 days after the first dose, and a fourth dose of 12 mg of ISIS 396443 is administered 211 days after the first dose. In certain embodiments, a first dose of 15 mg of ISIS 396443 is administered to a subject having one or more symptoms associated with SMA, a second dose of 15 mg of ISIS 396443 is administered 15 days after the first dose, a third dose of 15 mg of ISIS 396443 is administered 29 days after the first dose, and a fourth dose of 15 mg of ISIS 396443 is administered 211 days after the first dose.

In certain embodiments, a first dose of 3 mg of ISIS 396443 is administered to a subject having one or more symptoms associated with SMA, a second dose of 3 mg of ISIS 396443 is administered 15 days after the first dose, a third dose of 3 mg of ISIS 396443 is administered 29 days after the first dose, a fourth dose of 3 mg of ISIS 396443 is administered 64 days after the first dose, a fifth dose of 3 mg of ISIS 396443 is administered 183 days after the first dose, and a sixth dose of 3 mg of ISIS 396443 is administered 302 days after the first dose.

In certain embodiments, a first dose of 6 mg of ISIS 396443 is administered to a subject having one or more symptoms associated with SMA, a second dose of 6 mg of ISIS 396443 is administered 15 days after the first dose, a third dose of 6 mg of ISIS 396443 is administered 29 days after the first dose, a fourth dose of 6 mg of ISIS 396443 is administered 64 days after the first dose, a fifth dose of 6 mg of ISIS 396443 is administered 183 days after the first dose, and a sixth dose of 6 mg of ISIS 396443 is administered 302 days after the first dose.

In certain embodiments, a first dose of 9 mg of ISIS 396443 is administered to a subject having one or more symptoms associated with SMA, a second dose of 9 mg of ISIS 396443 is administered 15 days after the first dose, a third dose of 9 mg of ISIS 396443 is administered 29 days after the first dose, a fourth dose of 9 mg of ISIS 396443 is administered 64 days after the first dose, a fifth dose of 9 mg of ISIS 396443 is administered 183 days after the first dose, and a sixth dose of 9 mg of ISIS 396443 is administered 302 days after the first dose.

In certain embodiments, a first dose of 12 mg of ISIS 396443 is administered to a subject having one or more symptoms associated with SMA, a second dose of 12 mg of ISIS 396443 is administered 15 days after the first dose, a third dose of 12 mg of ISIS 396443 is administered 29 days after the first dose, a fourth dose of 12 mg of ISIS 396443 is administered 64 days after the first dose, a fifth dose of 12 mg of ISIS 396443 is administered 183 days after the first dose, and a sixth dose of 12 mg of ISIS 396443 is administered 302 days after the first dose.

In certain embodiments, a first dose of 15 mg of ISIS 396443 is administered to a subject having one or more symptoms associated with SMA, a second dose of 15 mg of ISIS 396443 is administered 15 days after the first dose, a third dose of 15 mg of ISIS 396443 is administered 29 days after the first dose, a fourth dose of 15 mg of ISIS 396443 is administered 64 days after the first dose, a fifth dose of 15 mg of ISIS 396443 is administered 183 days after the first dose, and a sixth dose of 15 mg of ISIS 396443 is administered 302 days after the first dose.

In certain embodiments, a first dose of 18 mg of ISIS 396443 is administered to a subject having one or more symptoms associated with SMA, a second dose of 18 mg of ISIS 396443 is administered 15 days after the first dose, a third dose of 18 mg of ISIS 396443 is administered 29 days after the first dose, a fourth dose of 18 mg of ISIS 396443 is administered 64 days after the first dose, a fifth dose of 18 mg of ISIS 396443 is administered 183 days after the first dose, and a sixth dose of 18 mg of ISIS 396443 is administered 302 days after the first dose.

In certain embodiments, a first dose of 12 mg of ISIS 396443 is administered to a subject having one or more symptoms associated with SMA, a second dose is administered 12-18 days after the first dose, a third dose is administered 25-35 days after the first dose, a fourth dose is administered 60-70 days after the first dose, a fifth dose is administered 178-188 days after the first dose, a sixth dose is administered 298-308 days after the first dose is administered, and each subsequent dose thereafter is administered at six month intervals.

In certain embodiments, a first dose of 12 mg equivalent of ISIS 396443 is administered to a subject having one or more symptoms associated with Type I SMA, a second dose is administered 12-18 days after the first dose, a third dose is administered 25-35 days after the first dose, a fourth dose is administered 60-70 days after the first dose, a fifth dose is administered 178-188 days after the first dose, a sixth dose is administered 298-308 days after the first dose is administered, and each subsequent dose thereafter is administered at six month intervals.

Proposed dose frequency is approximate, for example, in certain embodiments if the proposed dose frequency is a dose at day 1 and a second dose at day 29, an SMA patient may receive a second dose 25, 26, 27, 28, 29, 30, 31, 32, 33, or 34 days after receipt of the first dose. In certain embodiments, if the proposed dose frequency is a dose at day 1 and a second dose at day 15, an SMA patient may receive a second dose 10, 11, 12, 13, 14, 15, 16, 17, 18, 19, or 20 days after receipt of the first dose. In certain embodiments, if the proposed dose frequency is a dose at day 1 and a second dose at day 85, an SMA patient may receive a second dose 80, 81, 82, 83, 84, 85, 86, 87, 88, 89, or 90 days after receipt of the first dose.

In certain embodiments, the dose and/or the volume of the injection will be adjusted based on the patient's age. In certain embodiments, the dose and/or the volume of the injection will be adjusted based on the patient's CSF volume. In certain embodiments, the dose and/or the volume of the injection will be adjusted based on the patient's age and/or estimated CSF volume. In certain embodiments, the volume of the injection is adjusted such that each patient will receive a 12 mg equivalent dose based on CSF volume scaling. (For example, see Matsuzawa J, Matsui M, Konishi T, Noguchi K, Gur R C, Bilker W, Miyawaki T. Age-related volumetric changes of brain gray and white matter in healthy infants and children. Cereb Cortex 2001 April; 11(4):335-342, which is hereby incorporated by reference in its entirety). In certain embodiments, the volume of the injection is adjusted such that each patient will receive a 12 mg equivalent dose based on CSF volume scaling. (For example, see Matsuzawa J, Matsui M, Konishi T, Noguchi K, Gur R C, Bilker W, Miyawaki T. Age-related volumetric changes of brain gray and white matter in healthy infants and children. Cereb Cortex 2001 April; 11(4):335-342, which is hereby incorporated by reference in its entirety).

15. Co-Administration

In certain embodiments, pharmaceutical compositions of the present invention are co-administered with at least one other pharmaceutical composition for treating SMA and/or for treating one or more symptom associated with SMA. In certain embodiments, such other pharmaceutical composition is selected from trichostatin-A, valproic acid, riluzole, hydroxyurea, and a butyrate or butyrate derivative. In certain embodiments, pharmaceutical compositions of the present invention are co-administered with trichostatin A. In certain embodiments, pharmaceutical compositions of the present invention are co-administered with a derivative of quinazoline, for example as described in Thurmond, et al., J. Med Chem. 2008, 51, 449-469. In certain embodiments, a pharmaceutical composition of the present invention and at least one other pharmaceutical composition are co-administered at the same time. In certain embodiments, a pharmaceutical composition of the present invention and at least one other pharmaceutical composition are co-administered at different times.

In certain embodiments, pharmaceutical compositions of the present invention are co-administered with a gene therapy agent. In certain such embodiments, the gene therapy agent is administered to the CSF and the pharmaceutical composition of the present invention is administered systemically. In certain such embodiments, the gene therapy agent is administered to the CSF and the pharmaceutical composition of the present invention is administered to the CSF and systemically. In certain embodiments, a pharmaceutical composition of the present invention and a gene therapy agent are co-administered at the same time. In certain embodiments, a pharmaceutical composition of the present invention and a gene therapy agent are co-administered at different times. Certain gene therapy approaches to SMA treatment have been reported (e.g.,Coady et al., PLoS ONE 2008 3(10): e3468; Passini et al., J Clin Invest 2010 Apr. 1, 120(4): 1253-64).

In certain embodiments, pharmaceutical compositions of the present invention are co-administered with at least one other therapy for SMA. In certain embodiments, such other therapy for SMA is surgery. In certain embodiments, such other therapy is physical therapy, including, but not limited to exercises designed to strengthen muscles necessary for breathing, such as cough therapy. In certain embodiments, other therapy is a physical intervention, such as a feeding tube or device for assisted breathing.

In certain embodiments, pharmaceutical compositions of the present invention are co-administered with one or more other pharmaceutical compositions that reduce an undesired side-effect of the pharmaceutical compositions of the present invention.

16. Phenotypic Effects

In certain embodiments, administration of at least one pharmaceutical composition of the present invention results in a phenotypic change in the subject. In certain embodiments, such phenotypic changes include, but are not limited to: increased absolute amount of SMN mRNA that includes exon 7; increase in the ratio SMN mRNA that includes exon 7 to SMN mRNA lacking exon 7; increased absolute amount of SMN protein that includes exon 7; increase in the ratio SMN protein that includes exon 7 to SMN protein lacking exon 7; improved muscle strength, improved electrical activity in at least one muscle; improved respiration; weight gain; and survival. In certain embodiments, at least one phenotypic change is detected in a motoneuron of the subject. In certain embodiments, administration of at least one pharmaceutical composition of the present invention results in a subject being able to sit-up, to stand, and/or to walk. In certain embodiments, administration of at least one pharmaceutical composition of the present invention results in a subject being able to eat, drink, and/or breathe without assistance. In certain embodiments, efficacy of treatment is assessed by electrophysiological assessment of muscle. In certain embodiments, administration of a pharmaceutical composition of the present invention improves at least one symptom of SMA and has little or no inflammatory effect. In certain such embodiment, absence of inflammatory effect is determined by the absence of significant increase in Aif1 levels upon treatment.

In certain embodiments, administration of at least one pharmaceutical composition of the present invention delays the onset of at least one symptom of SMA. In certain embodiments, administration of at least one pharmaceutical composition of the present invention slows the progression of at least one symptom of SMA. In certain embodiments, administration of at least one pharmaceutical composition of the present invention reduces the severity of at least one symptom of SMA.

In certain embodiments, administration of at least one pharmaceutical composition of the present disclosure to a subject having SMA results in the subject improving his or her Hammersmith Functional Motor Scale-Expanded (HFMSE). The HFMSE is a reliable and validated tool used to assess motor function in children with SMA. In certain embodiments, the HFMSE is used to assess responses on 33 motor function tasks, where each task is scored on a scale from 0 to 2. In certain embodiments, administration of at least one pharmaceutical composition of the present disclosure to a subject having SMA results in the subject improving his or her Pediatric Quality of Life Inventory (PedsQL™) Measurement 4.0 Generic Core Scales. In certain embodiments, administration of at least one pharmaceutical composition of the present disclosure to a subject having SMA results in the subject improving his or her Pediatric Quality of Life Inventory 3.0 Neuromuscular Modules. In certain embodiments, administration of at least one pharmaceutical composition of the present disclosure to a subject having SMA results in the subject improving his or her health-related quality of life. In certain embodiments, administration of at least one pharmaceutical composition of the present disclosure to a subject having SMA results in the subject improving his or her Compound Muscle Action Potential (CMAP). In certain embodiments, administration of at least one pharmaceutical composition of the present disclosure to a subject having SMA results in the subject improving his or her Motor Unit Number Estimation (MUNE). CMAP and MUNE are electrophysiological techniques that can be used to determine the approximate number of motor neurons in a muscle or group of muscles. MUNE methods also provide a means of measuring motor unit size, enabling tracking of the number of motor units and the compensatory phenomenon of collateral reinnervation. CMAP and MUNE are well validated methods for tracking disease progression in neuromuscular disorders such as spinal muscular atrophy and amyotrophic lateral sclerosis.

In certain embodiments, administration of the present invention results in an undesired side-effect. In certain embodiments, a treatment regimen is identified that results in desired amelioration of symptoms while avoiding undesired side-effects.

17. Dosage Units

In certain embodiments pharmaceutical compositions of the present invention are prepared as dosage units for administration. Certain such dosage units are at concentrations selected from 0.01 mg to 100 mg. In certain such embodiments, a pharmaceutical composition of the present invention comprises a dose of antisense compound selected from 0.01 mg, 0.1 mg, 0.5 mg, 1 mg, 5 mg, 10 mg, 20 mg, 25 mg, 50 mg, 75 mg, 100 mg, 150 mg, and 200 mg. In certain embodiments, a pharmaceutical composition is comprises a dose of oligonucleotide selected from 0.1 mg, 0.5 mg, 1 mg, 5 mg, 10 mg, 25 mg, and 50 mg.

18. Kits

In certain embodiments, the present disclosure provides kits comprising at least one pharmaceutical composition. In certain embodiments, such kits further comprise a means of delivery, for example a syringe or infusion pump.

In certain embodiments, the present disclosure provides kits comprising a means for measuring the amount of SMN protein in a sample of CSF. In certain embodiments, the present disclosure provides kits comprising one or more antibodies and provides a means for measuring the amount of SMN protein in a sample of CSF.

In certain embodiments, the present disclosure provides kits comprising a capture antibody and a detection antibody. In certain embodiments, the capture antibody recognizes an N-terminal epitope of the SMN2 protein. In certain embodiments, the capture antibody specifically binds to a polypeptide comprising the amino acid sequence: gggvpeq (SEQ ID NO: 25). In certain embodiments, the capture antibody specifically binds to a polypeptide comprising the amino acid sequence: mamssggsgg gypeqedsvl frr (SEQ ID NO: 26). In certain embodiments, the capture antibody is Millipore antibody MABE230. In certain embodiments, the detection antibody specifically binds to a polypeptide comprising the amino acid sequence: DNIKPKS (SEQ ID NO: 27). In certain embodiments, the detection antibody specifically binds to a polypeptide comprising the amino acid sequence: srspgnks dnikpksapw nsflp (SEQ ID NO: 28). In certain embodiments, the detection antibody is ProteinTech antibody #60154-1-Ig.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited herein is hereby incorporated by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified bases, such as "AT$^{me}$CGAUCG," wherein $^{me}$C indicates a cytosine base comprising a methyl group at the 5-position.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Compounds Targeting SMN2

The following oligonucleotides were synthesized using standard techniques previously reported.

| Reference # | Sequence | Length | Chemistry | SEQ ID NO |
|---|---|---|---|---|
| ISIS396443 | TCACTTTCA TAATGCTGG | 18 | Full 2'-MOE; full PS | 1 |
| ISIS396449 | TTTCATAAT GCTGGC | 15 | Full 2'-MOE; full PS | 2 |

PS = phosphorothioate internucleoside linkages
All C residues are 5-methylcytosines.

Example 2

Selection of Antibodies

A series of monoclonal SMN antibodies were evaluated for binding to His-tagged recombinant human SMN protein (ProteinTech, catalog #ag14333) using a Bio-Layer Interferometry system (BLItz, Fortebio Inc., Menlo Park, CA). The antibodies tested were BD Biosciences anti-SMN (catalog #610647), Millipore anti-SMN2 (catalog #MABE230), ProteinTech anti-SMN2 (catalog #60154-1-Ig), and ProteinTech anti-SMN2 (catalog #60154-2-Ig). A previously tested antibody, Enzo anti-SMN1 (catalog #ADI-NBA-202-200), was used as a positive control. The His-tagged recombinant human SMN protein was added to the BLItz instrument and immobilized on the BLI biosensor tip surface. In each run, a different antibody was added to the instrument and binding was measured over time. The resulting rate and dissociation constants ($k_a$, $k_d$, and $K_D$) were calculated, and the results are listed in Table 1. The results show that the ProteinTech antibody #60154-1-Ig and Millipore antibody MABE230 had the lowest $K_D$ values.

TABLE 1

| Bio-Layer Interferometry | | | |
|---|---|---|---|
| Antibody | $k_a$ (1/M · s) | $k_d$ (1/s) | $K_D$ (M) |
| Enzo ADI-NBA-202-200 | $1.23 \times 10^4$ | $<1 \times 10^{-7}$ | $<1 \times 10^{-10}$ |
| BD 610647 | $6.37 \times 10^5$ | $1.09 \times 10^2$ | $1.71 \times 10^{-4}$ |
| MABE230 | $1.05 \times 10^5$ | $<1 \times 10^{-7}$ | $<1 \times 10^{-12}$ |
| PT 60154-1-Ig | $1.18 \times 10^5$ | $<1 \times 10^{-7}$ | $<1 \times 10^{-12}$ |
| PT 60154-2-Ig | $8.84 \times 10^2$ | $<1 \times 10^{-7}$ | $<1 \times 10^{-9}$ |

Example 3

Selection of Antibody Orientation

The MABE230 and PT 60154-1-Ig antibodies from Example 1 were selected for use in an SMN detection assay using the Erenna Immunoassay System (Singulex, Alameda, CA). In order to determine the antibody orientation to be used, two sets of conditions were tested. In the first set of conditions tested, MABE230 was used as the capture antibody and PT 60154-1-Ig was used as the detection antibody (Table 2). In the second set of conditions tested, PT 60154-1-Ig was used as the capture antibody and MABE230 was used as the detection antibody (Table 3). In each case, the capture antibody was labeled with a chemical handle to facilitate binding to magnetic microparticles (MPs, Singulex), and the detection antibody was labeled with a fluorophore prior to use in the assay.

MPs coated with a ligand that binds the capture antibody label were mixed with 12.5 or 25 µg of capture antibody per mg of MPs, then diluted to 50 or 100 µg/mL in assay buffer containing Tris buffer, BSA, 0.25% surfactant and a comprehensive blocking cocktail (Singulex). His-tagged recombinant human SMN protein (ProteinTech, catalog #ag14333) was diluted to 2 or 10 pg/mL in standard diluent comprising Tris buffer and a high concentration of BSA (Singulex). 100 µL of the capture antibody-MP mixture and either 100 µL of the diluted human SMN recombinant protein or 100 µL of standard diluent were added to each well of a 96-well plate and incubated two hours at 25° C. in a Jitterbug shaker (Boekel Scientific, Feasterville, PA) set to speed 5. In order to remove unbound capture antibody, the MPs were then retained via a magnetic bed and washed once with buffered saline solution containing surfactant (wash buffer, Singulex) using a Hydroflex 96-well plate washer (Tecan, Switzerland). The detection antibody was diluted to 50, 100, 500, or 1,000 ng/mL in assay buffer, filtered through a 0.2 µm filter (catalog #4187, Pall, Port Washington, NY), and 20 µL of the diluted detection antibody was added to each well of the 96-well plate. The plate was incubated one hour at 25° C. in a Jitterbug shaker set to speed 5. In order to remove unbound detection antibody, the MPs were then retained via a magnetic bed and washed four times with wash buffer using the Hydroflex plate washer. In order to eliminate fluorescent signal from non-specific binding of the detection antibody to the 96-well plate, the samples were then transferred to a new 96-well plate, and the remaining buffer was aspirated. 10 µL of Elution Buffer B (Singulex) was then added to each well, incubated at least five minutes at 25° C. in a Jitterbug shaker set to speed 5. While the MPs were retained via a magnetic bed, the elution mixture containing the detection antibody was transferred to a 384-well plate containing 10 μL of Buffer D (neutralization buffer, Singulex) per well. The amount of detection antibody present in each well was determined via single molecule counting using the Erenna System. Each well was read on the Erenna System for 60 seconds.

In Tables 2 and 3, "Cap Ab" indicates capture antibody, "Det Ab" indicates detection antibody, "n" indicates the number of replicate runs completed, "DE" indicates average detected events for each set of replicates, "SD" indicates standard deviation, "CV %" indicates the percent coefficient of variation, and "LoD" indicates the limit of detection. The slope refers to the slope of the line generated by the two SMN analyte concentration points tested for each condition (0 and 2 pg/mL or 0 and 10 pg/mL). LoD was calculated by multiplying the standard deviation of the background signal by two and dividing it by the slope. Optimal conditions are those in which background signal is low and DE signal is high (giving a high slope) and in which LoD is low. The background signal is the average DE at 0 pg/mL SMN protein for each set of conditions tested.

TABLE 2

Erenna assay with MABE230 as capture antibody and PT 60154-4-Ig as detection antibody

| MPs (μg/well) | Det Ab (ng/mL) | Cap Ab/MP (μg/mg) | [SMN] (pg/mL) | n | DE | DE SD | DE CV % | Slope | LoD (pg/mL) |
|---|---|---|---|---|---|---|---|---|---|
| 10 | 1000 | 25 | 2 | 3 | 2668 | 174 | 7 | 1272 | 0.023 |
|  |  |  | 0 | 3 | 125 | 15 | 12 |  |  |
|  |  | 12.5 | 2 | 3 | 2919 | 82 | 3 | 1413 | 0.021 |
|  |  |  | 0 | 3 | 94 | 15 | 15 |  |  |
|  | 500 | 25 | 2 | 3 | 2396 | 234 | 10 | 1145 | 0.006 |
|  |  |  | 0 | 3 | 106 | 4 | 3 |  |  |
|  |  | 12.5 | 2 | 3 | 2116 | 121 | 6 | 1035 | 0.023 |
|  |  |  | 0 | 3 | 46 | 12 | 26 |  |  |
|  | 100 | 25 | 2 | 3 | 1128 | 56 | 5 | 525 | 0.043 |
|  |  |  | 0 | 3 | 78 | 11 | 15 |  |  |
|  |  | 12.5 | 2 | 3 | 1047 | 181 | 17 | 510 | 0.053 |
|  |  |  | 0 | 3 | 28 | 14 | 48 |  |  |
|  | 50 | 25 | 2 | 3 | 776 | 28 | 4 | 361 | 0.012 |
|  |  |  | 0 | 2 | 55 | 2 | 4 |  |  |
|  |  | 12.5 | 2 | 3 | 681 | 7 | 1 | 329 | 0.017 |
|  |  |  | 0 | 2 | 22 | 3 | 13 |  |  |
| 5 | 1000 | 25 | 2 | 3 | 2185 | 349 | 16 | 1052 | 0.099 |
|  |  |  | 0 | 3 | 81 | 52 | 64 |  |  |
|  |  | 12.5 | 2 | 3 | 2589 | 276 | 11 | 1274 | 0.013 |
|  |  |  | 0 | 3 | 41 | 8 | 20 |  |  |
|  | 500 | 25 | 2 | 3 | 1931 | 36 | 2 | 942 | 0.003 |
|  |  |  | 0 | 3 | 47 | 2 | 3 |  |  |
|  |  | 12.5 | 2 | 3 | 1952 | 128 | 7 | 967 | 0.007 |
|  |  |  | 0 | 3 | 19 | 4 | 19 |  |  |
|  | 100 | 25 | 2 | 3 | 817 | 4 | 1 | 391 | 0.030 |
|  |  |  | 0 | 3 | 35 | 6 | 16 |  |  |
|  |  | 12.5 | 2 | 2 | 753 | 95 | 13 | 370 | 0.006 |
|  |  |  | 0 | 3 | 13 | 1 | 9 |  |  |
|  | 50 | 25 | 2 | 3 | 560 | 22 | 4 | 267 | 0.004 |
|  |  |  | 0 | 3 | 27 | 1 | 2 |  |  |
|  |  | 12.5 | 2 | 3 | 450 | 48 | 11 | 217 | 0.028 |
|  |  |  | 0 | 3 | 17 | 3 | 18 |  |  |

TABLE 3

Erenna assay with PT 60154-4-Ig as capture antibody and MABE230 as detection antibody

| MPs (μg/well) | Det Ab (ng/mL) | Cap Ab/MP (μg/mg) | [SMN] (pg/mL) | n | DE | DE SD | DE CV % | Slope | LoD (pg/mL) |
|---|---|---|---|---|---|---|---|---|---|
| 10 | 1000 | 25 | 10 | 3 | 3368 | 173 | 5 | 329 | 0.034 |
|  |  |  | 0 | 2 | 74 | 6 | 8 |  |  |
|  |  | 12.5 | 10 | 3 | 3722 | 71 | 2 | 361 | 0.123 |
|  |  |  | 0 | 3 | 117 | 22 | 19 |  |  |
|  | 500 | 25 | 10 | 3 | 2135 | 91 | 4 | 209 | 0.006 |
|  |  |  | 0 | 3 | 43 | 1 | 1 |  |  |
|  |  | 12.5 | 10 | 3 | 2175 | 203 | 9 | 213 | 0.126 |
|  |  |  | 0 | 2 | 50 | 13 | 27 |  |  |
|  | 100 | 25 | 10 | 3 | 505 | 67 | 13 | 48 | 0.143 |
|  |  |  | 0 | 3 | 22 | 3 | 16 |  |  |
|  |  | 12.5 | 10 | 3 | 523 | 46 | 9 | 51 | 0.140 |
|  |  |  | 0 | 2 | 17 | 4 | 21 |  |  |

TABLE 3-continued

Erenna assay with PT 60154-4-Ig as capture antibody and MABE230 as detection antibody

| MPs (μg/well) | Det Ab (ng/mL) | Cap Ab/MP (μg/mg) | [SMN] (pg/mL) | n | DE | DE SD | DE CV % | Slope | LoD (pg/mL) |
|---|---|---|---|---|---|---|---|---|---|
|  | 50 | 25 | 10 | 3 | 269 | 30 | 11 | 25 | 0.368 |
|  |  |  | 0 | 3 | 24 | 5 | 19 |  |  |
|  |  | 12.5 | 10 | 3 | 302 | 32 | 11 | 29 | 0.438 |
|  |  |  | 0 | 2 | 12 | 6 | 55 |  |  |
| 5 | 1000 | 25 | 10 | 3 | 3441 | 167 | 5 | 339 | 0.083 |
|  |  |  | 0 | 3 | 48 | 14 | 29 |  |  |
|  |  | 12.5 | 10 | 3 | 3574 | 176 | 5 | 351 | 0.069 |
|  |  |  | 0 | 3 | 62 | 12 | 20 |  |  |
|  | 500 | 25 | 10 | 3 | 2044 | 149 | 7 | 202 | 0.045 |
|  |  |  | 0 | 3 | 24 | 5 | 19 |  |  |
|  |  | 12.5 | 10 | 3 | 1958 | 77 | 4 | 192 | 0.073 |
|  |  |  | 0 | 3 | 33 | 7 | 21 |  |  |
|  | 100 | 25 | 10 | 3 | 481 | 52 | 11 | 47 | 0.024 |
|  |  |  | 0 | 3 | 10 | 1 | 6 |  |  |
|  |  | 12.5 | 10 | 2 | 501 | 31 | 6 | 49 | 0.109 |
|  |  |  | 0 | 3 | 13 | 3 | 20 |  |  |
|  | 50 | 25 | 10 | 3 | 256 | 22 | 9 | 25 | 0.113 |
|  |  |  | 0 | 2 | 5 | 1 | 28 |  |  |
|  |  | 12.5 | 10 | 3 | 231 | 24 | 10 | 23 | 0.250 |
|  |  |  | 0 | 2 | 5 | 3 | 57 |  |  |

Example 4

Generation of Standard Curve Using Recombinant SMN Protein and Estimation of LLoQ Based on the results presented in Example 2, MABE230 was used as the capture antibody and PT60154-1-Ig was used as the detection antibody to generate a standard curve and estimate the lower limit of quantitation (LLoQ) of the assay. The Erenna assay was run using the protocol described in Example 2 except that fewer conditions were tested based on the Example 2 results: MPs were mixed with 12.5 μg of MABE230 capture antibody per mg of MPs and diluted to 50 μg/mL in assay buffer; and the detection antibody was diluted to 500, or 1,000 ng/mL in assay buffer. In order to generate the standard curve, 11 different concentrations of His-tagged recombinant human SMN protein in standard diluent (see Table 4) plus a control containing only standard diluent (0 pg/mL) were tested.

In Table 4, "Det Ab" indicates detection antibody, "n" indicates the number of replicate runs completed, "DE" indicates average detected events for each set of replicates, "CV %" indicates the percent coefficient of variation, "EP" indicates event photons, which is the sum of the photons counted in all of the detected events, and "ND" indicates not detected. The calculated SMN concentrations ("Calc [SMN]") were determined using the Erenna system SMD algorithm and Sgx Link software (Singulex), which takes into account detected events, event photons, and total photons in order to calculate analyte concentration across a wide dynamic range. "% recovery" is the percent of the calculated SMN concentration relative to the concentration of SMN analyte used.

TABLE 4

Standard curves generated with recombinant human SMN

| [SMN] (pg/mL) | n | DE | DE CV % | EP | EP CV % | Calc [SMN] (pg/mL) | Calc [SMN] CV % | % Recovery |
|---|---|---|---|---|---|---|---|---|
| 500 ng/mL Det Ab |  |  |  |  |  |  |  |  |
| 200.00 | 3 | 9463 | 3 | 18559403 | 4 | 201.61 | 8 | 101 |
| 66.67 | 3 | 12028 | 3 | 9530749 | 3 | 66.56 | 2 | 100 |
| 22.22 | 3 | 12224 | 5 | 3847763 | 18 | 26.20 | 16 | 118 |
| 7.41 | 3 | 5963 | 2 | 1047911 | 2 | 7.24 | 2 | 98 |
| 3.70 | 2 | 3190 | 0 | 496941 | 4 | 3.32 | 1 | 90 |
| 1.85 | 3 | 1846 | 15 | 267497 | 15 | 1.82 | 16 | 98 |
| 0.93 | 3 | 967 | 9 | 135432 | 9 | 0.93 | 9 | 101 |
| 0.46 | 3 | 562 | 15 | 77541 | 15 | 0.53 | 16 | 115 |
| 0.23 | 3 | 301 | 4 | 39971 | 4 | 0.27 | 4 | 115 |
| 0.12 | 3 | 154 | 13 | 19480 | 16 | 0.11 | 19 | 97 |
| 0.06 | 2 | 91 | 5 | 14178 | 19 | 0.083 | 72 | 144 |
| 0.00 | 3 | 33 | 26 | 5660 | 64 | ND | ND | ND |
| 1000 ng/mL Det A |  |  |  |  |  |  |  |  |
| 200.00 | 3 | 9361 | 4 | 20380681 | 2 | 200.58 | 3 | 100 |
| 66.67 | 3 | 11455 | 2 | 10594814 | 1 | 64.49 | 1 | 97 |
| 22.22 | 3 | 13136 | 1 | 4635858 | 9 | 24.68 | 9 | 111 |
| 7.41 | 3 | 7203 | 2 | 1320582 | 3 | 7.20 | 2 | 97 |

TABLE 4-continued

Standard curves generated with recombinant human SMN

| [SMN] (pg/mL) | n | DE | DE CV % | EP | EP CV % | Calc [SMN] (pg/mL) | Calc [SMN] CV % | % Recovery |
|---|---|---|---|---|---|---|---|---|
| 3.70 | 3 | 4327 | 5 | 706215 | 6 | 3.82 | 5 | 103 |
| 1.85 | 2 | 2137 | 3 | 312351 | 5 | 1.73 | 4 | 93 |
| 0.93 | 3 | 1170 | 7 | 170598 | 9 | 0.96 | 11 | 104 |
| 0.46 | 3 | 630 | 11 | 87395 | 11 | 0.48 | 11 | 104 |
| 0.23 | 3 | 330 | 4 | 44780 | 5 | 0.24 | 5 | 102 |
| 0.12 | 3 | 193 | 10 | 26294 | 10 | 0.12 | 14 | 104 |
| 0.06 | 3 | 125 | 19 | 15866 | 25 | 0.06 | 34 | 105 |
| 0.00 | 3 | 56 | 33 | 6807 | 32 | ND | ND | ND |

The standard curves for the 500 ng/mL and 1000 ng/mL detection antibody data sets were generated by plotting signal generated by the SMD algorithm against SMN concentration for the samples that generated less than 1,000 detected events. The slope of the standard curve for the 500 ng/mL detection antibody data set was 977, and the slope of the standard curve for the 1000 ng/mL detection antibody data set was 1210.

The LLoQ was defined as the lowest point on the standard curve with a calculated SMN concentration with a % recovery within 80-120% and CV %≤20%. Based on those criteria, the LLoQ was 0.12 pg/mL for both data sets. Since the LLoQ was the same for both concentrations of detection antibody tested, average CV %'s were also evaluated. Average CV % for DE was approximately equal (8.4%) for both detection antibody concentrations, but the average CV % for EP was 14.4% for 500 ng/mL detection antibody and 9.8% for 1000 ng/mL detection antibody. Due to the lower average EP CV % and greater slope of the standard curve, 1000 ng/mL detection antibody was used in subsequent experiments.

Example 5

Determination of the Lower Limit of Reliable Quantitation (LLoRQ)

The LLoQ of 0.12 pg/mL determined in Example 3 was verified by performing the assay with various SMN protein levels below and above 0.12 pg/mL. The Erenna assay was run using the general protocol described in Example 2. Specifically, MPs were mixed with 12.5 µg of MABE230 capture antibody per mg of MPs and diluted to 50 µg/mL in assay buffer; and the detection antibody was diluted to 1,000 ng/mL in assay buffer. The concentrations of SMN protein used are shown in Table 5 below.

In Table 5, "n" indicates the number of replicates, "DE" indicates average detected events, "SD" indicates standard deviation, and "CV %" indicates percent coefficient of variance. The calculated SMN concentrations ("Calc [SMN]") and % recovery were determined as in Example 3. The LLoRQ is defined as the analyte concentration at which recoveries are within 80-120% with less than 20 CV % for concentrations greater than one half of the LLoQ and recoveries are within 75-125% with less than 25 CV % for concentrations less than or equal to one half the LLoQ. The results in Table 5 show that the LLoQ of 0.12 pg/mL met these requirements and was determined to be the LLoRQ.

TABLE 5

Determination of LLoRQ

| [SMN] (pg/mL) | n | DE | DE SD | DE CV % | Calc [SMN] (pg/mL) | Calc [SMN] SD | Calc [SMN] CV % | % Recovery |
|---|---|---|---|---|---|---|---|---|
| 1.20 (10x LLoQ) | 2 | 1429 | 47 | 3 | 1.16 | 0.0412 | 4 | 96 |
| 0.60 (5x LLoQ) | 3 | 763 | 22 | 3 | 0.62 | 0.0147 | 2 | 103 |
| 0.24 (2x LLoQ) | 3 | 362 | 26 | 7 | 0.27 | 0.0224 | 8 | 114 |
| 0.12 (1x LLoQ) | 3 | 201 | 4 | 2 | 0.13 | 0.0035 | 3 | 109 |
| 0.06 (0.5x LLoQ) | 2 | 138 | 18 | 13 | 0.07 | 0.0170 | 23 | 122 |

Example 6

Prototype Sample Testing with Human Cerebral Spinal Fluid (CSF)

Prototype testing of the SMN assay with human CSF samples was completed using the assay conditions described in Example 4. Five different human CSF samples containing endogenous SMN protein were analyzed with and without spiked His-tagged recombinant human SMN protein at 5 or 10 pg/mL. The results are shown in Table 6 below. See Example 4 for a list of the abbreviations found in Table 6.

Each DE value shown is the average of two replicate samples. In Table 6, the % recovery was calculated by subtracting the calculated endogenous SMN concentration of the unspiked sample from the calculated total SMN concentration (including endogenous and recombinant SMN) of the spiked sample, dividing that result by the known concentration of spiked recombinant SMN, and multiplying that result by 100. Thus, the % recovery values refer only to the spiked, recombinant SMN protein and are not applicable to the unspiked samples that contain only endogenous SMN protein.

TABLE 6

Prototype testing of human CSF

| Human CSF sample No. | [SMN] spiked (pg/mL) | DE | DE SD | DE CV % | Calc [SMN] (pg/mL) | Calc [SMN] SD | Calc [SMN] CV % | % Recovery |
|---|---|---|---|---|---|---|---|---|
| 1 | 0.0 | 330 | 1 | 0 | 0.28 | 0.00 | 0 | n/a |
|  | 5.0 | 5072 | 389 | 8 | 5.10 | 0.47 | 9 | 96 |
|  | 10.0 | 9733 | 385 | 4 | 13.18 | 1.35 | 10 | 129 |
| 2 | 0.0 | 240 | 49 | 20 | 0.20 | 0.04 | 23 | n/a |
|  | 5.0 | 5312 | 7 | 0 | 5.39 | 0.02 | 0 | 104 |
|  | 10.0 | 9626 | 47 | 0 | 12.86 | 0.12 | 1 | 127 |
| 3 | 0.0 | 278 | 13 | 5 | 0.23 | 0.01 | 5 | n/a |
|  | 5.0 | 5982 | 110 | 2 | 6.27 | 0.09 | 1 | 121 |
|  | 10.0 | 9141 | 420 | 5 | 11.92 | 0.76 | 6 | 117 |
| 4 | 0.0 | 375 | 48 | 13 | 0.32 | 0.04 | 13 | n/a |
|  | 5.0 | 5812 | 34 | 1 | 6.10 | 0.11 | 2 | 116 |
|  | 10.0 | 8655 | 444 | 5 | 10.81 | 0.73 | 7 | 105 |
| 5 | 0.0 | 479 | 15 | 3 | 0.41 | 0.01 | 3 | n/a |
|  | 5.0 | 6074 | 322 | 5 | 6.46 | 0.43 | 7 | 121 |
|  | 10.0 | 9437 | 66 | 1 | 12.32 | 0.11 | 1 | 119 |

Example 7

Testing of Various Salt and Surfactant Concentrations

In order to evaluate assay performance in various salt and surfactant concentrations, recombinant human SMN was analyzed with 150, 450, 600, or 700 mM sodium chloride and 0.1, 0.25, 0.5, or 1% Triton-X detergent in the assay buffer using the protocol described in Example 4. The results are shown in Table 7, and the table abbreviations are listed in Example 4.

TABLE 7

Assay result with various salt and surfactant concentrations

| [NaCl] (mM) | [Surfactant] (%) | [SMN] (pg/mL) | n | DE | DE SD | DE CV % | slope | LOD (pg/mL) |
|---|---|---|---|---|---|---|---|---|
| 150 | 0.1 | 2 | 3 | 2104 | 254 | 12 | 1020 | 0.019 |
|  |  | 0 | 3 | 65 | 10 | 15 |  |  |
|  | 0.25 | 2 | 3 | 2411 | 165 | 7 | 1177 | 0.017 |
|  |  | 0 | 2 | 57 | 10 | 17 |  |  |
|  | 0.5 | 2 | 3 | 2565 | 252 | 10 | 1244 | 0.026 |
|  |  | 0 | 3 | 77 | 16 | 21 |  |  |
|  | 1 | 2 | 3 | 2211 | 231 | 10 | 1057 | 0.046 |
|  |  | 0 | 3 | 96 | 25 | 25 |  |  |
| 450 | 0.1 | 2 | 3 | 1546 | 139 | 9 | 744 | 0.009 |
|  |  | 0 | 3 | 59 | 3 | 5 |  |  |
|  | 0.25 | 2 | 2 | 2068 | 8 | 0 | 1003 | 0.003 |
|  |  | 0 | 2 | 61 | 1 | 2 |  |  |
|  | 0.5 | 2 | 3 | 1891 | 59 | 3 | 916 | 0.012 |
|  |  | 0 | 3 | 60 | 5 | 9 |  |  |
|  | 1 | 2 | 3 | 1501 | 268 | 18 | 715 | 0.022 |
|  |  | 0 | 2 | 72 | 8 | 11 |  |  |

TABLE 7-continued

Assay result with various salt and surfactant concentrations

| [NaCl] (mM) | [Surfactant] (%) | [SMN] (pg/mL) | n | DE | DE SD | DE CV % | slope | LOD (pg/mL) |
|---|---|---|---|---|---|---|---|---|
| 600 | 0.1 | 2 | 3 | 1075 | 103 | 10 | 516 | 0.004 |
|  |  | 0 | 3 | 44 | 1 | 2 |  |  |
|  | 0.25 | 2 | 3 | 1170 | 73 | 6 | 562 | 0.011 |
|  |  | 0 | 3 | 46 | 3 | 7 |  |  |
|  | 0.5 | 2 | 3 | 1115 | 101 | 9 | 525 | 0.069 |
|  |  | 0 | 3 | 66 | 18 | 27 |  |  |
|  | 1 | 2 | 3 | 1064 | 136 | 13 | 501 | 0.016 |
|  |  | 0 | 3 | 62 | 4 | 6 |  |  |
| 700 | 0.1 | 2 | 3 | 749 | 117 | 16 | 351 | 0.012 |
|  |  | 0 | 3 | 48 | 2 | 4 |  |  |
|  | 0.25 | 2 | 3 | 766 | 80 | 10 | 360 | 0.016 |
|  |  | 0 | 2 | 47 | 3 | 6 |  |  |
|  | 0.5 | 2 | 2 | 817 | 21 | 3 | 379 | 0.004 |
|  |  | 0 | 2 | 59 | 1 | 1 |  |  |
|  | 1 | 2 | 2 | 711 | 70 | 10 | 326 | 0.080 |
|  |  | 0 | 3 | 59 | 13 | 22 |  |  |

In order to maximize assay performance, the highest salt and surfactant concentrations that were not detrimental to assay performance were selected. High salt and surfactant concentrations decrease background and non-specific binding but can also cause reductions in slope, loss of assay sensitivity, and increase in LoD (Lower Limit of Detection). Thus, 150 mM salt and 0.25% surfactant were chosen or subsequent experiments, because those conditions achieved a high slope, low LoD, and low background (low detected events at 0 pg/mL SMN).

Example 8

Generation of Standard Curve and Verification of LLoQ

Based on the results presented in Example 6, 150 mM salt and 0.25% surfactant were used in the assay buffer to generate a standard curve and verify the lower limit of quantitation (LLoQ) of the assay. The Erenna assay was run using the protocol described in Example 4. In order to generate the standard curve, 11 different concentrations of His-tagged recombinant human SMN protein in standard diluent (see Table 8) plus a standard diluent only (0 pg/mL) control were tested.

In Table 8, "n" indicates the number of replicate runs completed, "DE" indicates average detected events for each set of replicates, "CV %" indicates the percent coefficient of variation, and "ND" indicates not detected. The calculated SMN concentrations and % recovery were determined as in Example 3.

TABLE 8

Standard curve generated with recombinant human SMN

| [SMN] (pg/mL) | n | DE | DE SD | DE CV % | Calc [SMN] (pg/mL) | Calc [SMN] SD | Calc [SMN] CV % | % Recovery |
|---|---|---|---|---|---|---|---|---|
| 100.00 | 2 | ND | ND | ND | 98.79 | 3.26 | 3 | 99 |
| 33.33 | 3 | ND | ND | ND | 33.98 | 1.31 | 4 | 102 |
| 11.11 | 3 | ND | ND | ND | 11.76 | 0.54 | 5 | 106 |
| 3.70 | 3 | ND | ND | ND | 3.72 | 0.18 | 5 | 100 |
| 1.85 | 2 | ND | ND | ND | 1.94 | 0.25 | 13 | 105 |
| 0.93 | 3 | 1015 | 115 | 11 | 0.82 | 0.10 | 12 | 89 |
| 0.46 | 2 | 605 | 20 | 3 | 0.48 | 0.02 | 3 | 104 |
| 0.23 | 3 | 314 | 31 | 10 | 0.24 | 0.03 | 11 | 103 |
| 0.12 | 2 | 190 | 4 | 2 | 0.13 | 0.00 | 2 | 112 |
| 0.06 | 3 | 111 | 6 | 5 | 0.06 | 0.01 | 9 | 100 |
| 0.03 | 3 | 74 | 4 | 5 | 0.02 | 0.00 | 16 | 82 |
| 0.00 | 2 | 50 | 1 | 3 | 0.01 | ND | ND | ND |

The standard curve was generated as in Example 3, using the data in Table 8. The slope of the standard curve was 1062, and the LLoQ was 0.03 pg/mL.

Example 9

Determination of Spike Recovery and Linearity of Dilution in Human CSF

The Erenna assay was performed as described in Example 7. Eight different human CSF samples were spiked with 0 or 1.2 pg/mL His-tagged recombinant human SMN protein, then analyzed to determine the % recovery of the spiked SMN protein, as in Example 5. Dilutions of the human CSF spiked with 1.2 pg/mL were then made and analyzed in order to determine the linearity of the assay. The experiment was repeated with various samples on separate days, and the results of both experiments are shown in Tables 9 and 10.

See Example 4 for a list of the abbreviations found in Tables 9 and 10. The % recovery was calculated as in Example 5. The % linearity of each dilution was determined by multiplying the calculated SMN concentration by two, then determining the percent of that result relative to the calculated SMN concentration corresponding to the dilution that was twice as concentrated.

TABLE 9

Spike recovery and linearity of dilution in human CSF

| Human CSF sample No. + spiked SMN or dilution | n | DE | DE SD | DE CV % | Calc [SMN] (pg/mL) | Calc [SMN] SD | Calc [SMN] CV % | % Recovery | % Linearity |
|---|---|---|---|---|---|---|---|---|---|
| 2 + 1.2 pg/mL | 3 | 1346 | 114 | 8 | 1.36 | 0.12 | 8 | 97 | n/a |
| 1:2 dilution | 3 | 651 | 29 | 4 | 0.66 | 0.03 | 5 | n/a | 97 |
| 1:4 dilution | 3 | 305 | 42 | 14 | 0.29 | 0.05 | 16 | n/a | 89 |
| 1:8 dilution | 3 | 185 | 14 | 7 | 0.15 | 0.02 | 11 | n/a | 106 |
| 2 + 0 pg/mL | 2 | 222 | 20 | 9 | 0.20 | 0.02 | 12 | n/a | n/a |
| 3 + 1.2 pg/mL | 3 | 1456 | 53 | 4 | 1.47 | 0.05 | 4 | 87 | n/a |
| 1:2 dilution | 3 | 714 | 110 | 15 | 0.72 | 0.11 | 15 | n/a | 98 |
| 1:4 dilution | 3 | 361 | 57 | 16 | 0.35 | 0.06 | 17 | n/a | 98 |
| 1:8 dilution | 3 | 216 | 29 | 14 | 0.19 | 0.03 | 18 | n/a | 108 |
| 3 + 0 pg/mL | 3 | 434 | 12 | 3 | 0.43 | 0.01 | 3 | n/a | n/a |
| 4 + 1.2 pg/mL | 2 | 1251 | 21 | 2 | 1.27 | 0.02 | 2 | 85 | n/a |
| 1:2 dilution | 2 | 692 | 28 | 4 | 0.70 | 0.03 | 4 | n/a | 111 |
| 1:4 dilution | 2 | 380 | 24 | 6 | 0.38 | 0.03 | 7 | n/a | 107 |
| 1:8 dilution | 2 | 186 | 27 | 14 | 0.16 | 0.03 | 21 | n/a | 83 |
| 4 + 0 pg/mL | 2 | 267 | 49 | 19 | 0.25 | 0.06 | 23 | n/a | n/a |
| 5 + 1.2 pg/mL | 2 | 1571 | 7 | 0 | 1.59 | 0.01 | 0 | 99 | n/a |
| 1:2 dilution | 2 | 788 | 14 | 2 | 0.80 | 0.01 | 2 | n/a | 101 |
| 1:4 dilution | 2 | 341 | 28 | 8 | 0.33 | 0.03 | 9 | n/a | 83 |
| 1:8 dilution | 2 | 206 | 6 | 3 | 0.23 | 0.07 | 33 | n/a | 136 |
| 5 + 0 pg/mL | 1 | 398 | n/a | n/a | 0.40 | n/a | n/a | n/a | n/a |
| 6 + 1.2 pg/mL | 2 | 1433 | 170 | 12 | 1.45 | 0.18 | 12 | 94 | n/a |
| 1:2 dilution | 2 | 682 | 90 | 13 | 0.69 | 0.09 | 13 | n/a | 95 |
| 1:4 dilution | 2 | 348 | 6 | 2 | 0.34 | 0.01 | 2 | n/a | 98 |
| 1:8 dilution | 2 | 194 | 27 | 14 | 0.17 | 0.03 | 19 | n/a | 97 |
| 6 + 0 pg/mL | 1 | 336 | n/a | n/a | 0.33 | n/a | n/a | n/a | n/a |

TABLE 10

Spike recovery and linearity of dilution in human CSF

| Human CSF sample No. + spiked SMN or dilution | n | DE | DE SD | DE CV % | Calc [SMN] (pg/mL) | Calc [SMN] SD | Calc [SMN] CV % | % Recovery | % Linearity |
|---|---|---|---|---|---|---|---|---|---|
| 2 + 1.2 pg/mL | 3 | 1669 | 97 | 6 | 1.55 | 0.10 | 6 | 115 | n/a |
| 1:2 dilution | 3 | 767 | 41 | 5 | 0.67 | 0.04 | 6 | n/a | 86 |
| 1:4 dilution | 3 | 369 | 10 | 3 | 0.30 | 0.01 | 3 | n/a | 91 |
| 1:8 dilution | 3 | 214 | 8 | 4 | 0.16 | 0.01 | 4 | n/a | 105 |
| 2 + 0 pg/mL | 3 | 230 | 17 | 7 | 0.17 | 0.02 | 9 | n/a | n/a |
| 3 + 1.2 pg/mL | 3 | 1709 | 160 | 9 | 1.59 | 0.17 | 10 | 99 | n/a |
| 1:2 dilution | 3 | 769 | 31 | 4 | 0.67 | 0.03 | 4 | n/a | 84 |
| 1:4 dilution | 3 | 406 | 11 | 3 | 0.34 | 0.01 | 3 | n/a | 100 |
| 1:8 dilution | 3 | 242 | 20 | 8 | 0.19 | 0.02 | 10 | n/a | 110 |
| 3 + 0 pg/mL | 3 | 469 | 44 | 9 | 0.40 | 0.04 | 10 | n/a | n/a |
| 7 + 1.2 pg/mL | 2 | 2078 | 50 | 2 | 1.98 | 0.06 | 3 | 77 | n/a |

TABLE 10-continued

Spike recovery and linearity of dilution in human CSF

| Human CSF sample No. + spiked SMN or dilution | n | DE | DE SD | DE CV % | Calc [SMN] (pg/mL) | Calc [SMN] SD | Calc [SMN] CV % | % Recovery | % Linearity |
|---|---|---|---|---|---|---|---|---|---|
| 1:2 dilution | 2 | 1005 | 134 | 13 | 0.89 | 0.13 | 14 | n/a | 90 |
| 1:4 dilution | 2 | 398 | 5 | 1 | 0.33 | 0.00 | 1 | n/a | 74 |
| 1:8 dilution | 2 | 254 | 26 | 10 | 0.20 | 0.02 | 12 | n/a | 119 |
| 7 + 0 pg/mL | 2 | 1174 | 41 | 3 | 1.06 | 0.04 | 3 | n/a | n/a |
| 1 + 1.2 pg/mL | 2 | 1475 | 9 | 1 | 1.35 | 0.01 | 1 | 92 | n/a |
| 1:2 dilution | 2 | 713 | 6 | 1 | 0.62 | 0.01 | 1 | n/a | 92 |
| 1:4 dilution | 2 | 400 | 21 | 5 | 0.33 | 0.02 | 6 | n/a | 107 |
| 1:8 dilution | 2 | 219 | 7 | 3 | 0.16 | 0.01 | 4 | n/a | 99 |
| 1 + 0 pg/mL | 2 | 306 | 38 | 12 | 0.25 | 0.04 | 15 | n/a | n/a |
| 8 + 1.2 pg/mL | 2 | 2554 | 54 | 2 | 2.51 | 0.06 | 2 | 120 | n/a |
| 1:2 dilution | 2 | 1060 | 69 | 6 | 0.94 | 0.07 | 7 | n/a | 75 |
| 1:4 dilution | 2 | 552 | 70 | 13 | 0.47 | 0.06 | 14 | n/a | 100 |
| 1:8 dilution | 2 | 232 | 67 | 29 | 0.18 | 0.06 | 36 | n/a | 74 |
| 8 + 0 pg/mL | 2 | 1190 | 91 | 8 | 1.07 | 0.09 | 8 | n/a | n/a |

Example 10

Determination of Intra-Assay and Inter-Assay Precision with Human CSF

In order to evaluate intra-assay precision, five human CSF samples were spiked with 0.6 pg/mL recombinant SMN protein, and six replicates of each sample were analyzed using the Erenna assay as described in Example 7. The results are shown in Table 11.

In order to evaluate inter-assay precision, the results from sample numbers 2 and 3 and their respective dilutions, shown in Tables 9 and 10 in Example 8 were analyzed. The results shown in Table 12 are the combined results for the two replicate experiments, which were performed on separate days.

In Table 11, "R" indicates a replicate, and other abbreviations in Tables 11 and 12 are listed in Example 4.

TABLE 11

Intra-assay precision with human CSF

| Human CSF sample No. + spiked SMN | R1 | R2 | R3 | R4 | R5 | R6 | Mean | SD | CV % |
|---|---|---|---|---|---|---|---|---|---|
| Detected Events (DE) | | | | | | | | | |
| 2 + 0.6 pg/mL | 1426 | 1351 | 1272 | 1080 | 1263 | 1341 | 1289 | 118 | 9 |
| 3 + 0.6 pg/mL | 1737 | 1458 | 1699 | 1567 | 1689 | 1786 | 1656 | 121 | 7 |
| 4 + 0.6 pg/mL | 1377 | 1389 | 1411 | 1396 | 1348 | 1423 | 1391 | 26 | 2 |
| 5 + 0.6 pg/mL | 1544 | 1618 | 1552 | 1640 | 1663 | 1812 | 1638 | 98 | 6 |
| 6 + 0.6 pg/mL | 1545 | 1539 | 1498 | 1557 | 1377 | 1513 | 1505 | 66 | 4 |
| Calc [SMN] (pg/mL) | | | | | | | | | |
| 2 + 0.6 pg/mL | 0.87 | 0.83 | 0.78 | 0.66 | 0.77 | 0.82 | 0.79 | 0.07 | 9 |
| 3 + 0.6 pg/mL | 1.07 | 0.90 | 1.04 | 0.96 | 1.04 | 1.10 | 10.2 | 0.07 | 7 |
| 4 + 0.6 pg/mL | 0.85 | 0.85 | 0.86 | 0.91 | 0.83 | 0.87 | 0.86 | 0.03 | 3 |
| 5 + 0.6 pg/mL | 0.95 | 0.99 | 0.95 | 1.01 | 1.02 | 1.11 | 1.00 | 0.06 | 6 |
| 6 + 0.6 pg/mL | 0.95 | 0.94 | 0.92 | 0.96 | 0.85 | 0.93 | 0.92 | 0.04 | 4 |

TABLE 12

Inter-assay precision with human CSF based on data shown in Tables 9 and 10

| Human CSF sample No. + spiked SMN or dilution | Calc [SMN] (pg/mL) | Calc [SMN] SD | Calc [SMN] CV % |
|---|---|---|---|
| 2 + 1.2 pg/mL | 1.46 | 0.13 | 9 |
| 1:2 | 0.67 | 0.01 | 1 |
| 1:4 | 0.30 | 0.01 | 3 |
| 1:8 | 0.16 | 0.00 | 2 |
| 2 + 0 pg/mL | 0.19 | 0.02 | 9 |
| 3 + 1.2 pg/mL | 1.53 | 0.08 | 5 |
| 1:2 | 0.70 | 0.04 | 5 |
| 1:4 | 0.35 | 0.01 | 4 |
| 1:8 | 0.19 | 0.00 | 2 |
| 3 + 0 pg/mL | 0.41 | 0.03 | 7 |

Example 11

Transgenic Mouse CSF Testing

CSF from eleven transgenic mice expressing human SMN1 was collected and pooled into four samples, then diluted with standard diluent in order for all samples to contain the same total volume. The concentration of human SMN protein in each sample was determined by performing the Erenna assay as described in Example 7. The results are shown in Table 13, and the abbreviations in Table 13 are listed in Example 4.

TABLE 13

Concentration of human SMN in transgenic mouse CSF

| Sample | n | DE | DE SD | DE CV % | Calc [SMN] (pg/mL) | Calc [SMN] SD | Calc [SMN] CV % | Dilution factor | Dilution corrected [SMN] (pg/mL) |
|---|---|---|---|---|---|---|---|---|---|
| 1 | 2 | 1517 | 30 | 2 | 1.45 | 0.03 | 2.3 | 9.8 | 14.2 |
| 2 | 2 | 970 | 57 | 6 | 0.88 | 0.06 | 6.5 | 8.0 | 7.0 |
| 3 | 2 | 3061 | 2 | 0 | 3.35 | 0.01 | 0.3 | 14.1 | 47.2 |
| 4 | 2 | 1000 | 59 | 6 | 0.91 | 0.06 | 6.8 | 8.1 | 7.4 |

Example 12

Human CSF Testing

The concentration of SMN protein in fifty-five undiluted human CSF samples was determined using the Erenna assay as described in Example 7. The results are shown in Table 14, and the abbreviations in Table 14 are listed in Example 4. Sample 28 produced an abnormally high value, possibly due to contamination with blood, and the sample was hemolyzed.

TABLE 14

Concentration of SMN human CSF

| Sample | n | DE | DE SD | DE CV % | Calc [SMN] (pg/mL) | Calc [SMN] SD | Calc [SMN] CV % |
|---|---|---|---|---|---|---|---|
| 9 | 2 | 343 | 8 | 2 | 0.26 | 0.01 | 3 |
| 10 | 2 | 575 | 47 | 8 | 0.47 | 0.04 | 9 |
| 11 | 2 | 671 | 51 | 8 | 0.56 | 0.05 | 8 |
| 12 | 2 | 970 | 117 | 12 | 0.83 | 0.11 | 13 |
| 13 | 2 | 343 | 11 | 3 | 0.26 | 0.01 | 4 |
| 14 | 2 | 538 | 18 | 3 | 0.44 | 0.01 | 3 |
| 15 | 2 | 950 | 23 | 2 | 0.81 | 0.02 | 3 |
| 16 | 2 | 776 | 24 | 3 | 0.65 | 0.02 | 3 |
| 17 | 2 | 551 | 52 | 9 | 0.45 | 0.05 | 10 |
| 18 | 2 | 373 | 16 | 4 | 0.28 | 0.01 | 5 |
| 19 | 2 | 1509 | 99 | 7 | 1.31 | 0.09 | 7 |
| 20 | 2 | 590 | 54 | 9 | 0.49 | 0.04 | 9 |
| 21 | 2 | 378 | 12 | 3 | 0.29 | 0.01 | 4 |
| 22 | 2 | 1357 | 53 | 4 | 1.18 | 0.05 | 4 |
| 23 | 2 | 1066 | 8 | 1 | 0.92 | 0.02 | 2 |
| 24 | 2 | 503 | 43 | 9 | 0.40 | 0.04 | 10 |
| 25 | 2 | 579 | 55 | 10 | 0.48 | 0.05 | 11 |
| 26 | 2 | 356 | 11 | 3 | 0.27 | 0.01 | 4 |
| 27 | 2 | 493 | 1 | 0 | 0.40 | 0.00 | 1 |
| 28 | 1 | 10974 | n/a | n/a | 16.97 | n/a | n/a |
| 29 | 2 | 783 | 90 | 11 | 0.57 | 0.07 | 12 |
| 30 | 2 | 823 | 1 | 0 | 0.70 | 0.00 | 0.1 |
| 31 | 2 | 680 | 55 | 8 | 0.49 | 0.05 | 10 |
| 32 | 1 | 386 | n/a | n/a | 0.26 | n/a | n/a |
| 33 | 2 | 686 | 8 | 1 | 0.57 | 0.01 | 1 |
| 34 | 2 | 506 | 45 | 9 | 0.41 | 0.04 | 10 |
| 35 | 2 | 861 | 64 | 7 | 0.63 | 0.05 | 8 |
| 36 | 2 | 572 | 47 | 8 | 0.47 | 0.04 | 9 |
| 37 | 2 | 398 | 77 | 19 | 0.27 | 0.06 | 22 |
| 38 | 2 | 656 | 121 | 18 | 0.47 | 0.09 | 20 |
| 39 | 2 | 690 | 99 | 14 | 0.50 | 0.08 | 16 |
| 40 | 2 | 472 | 22 | 5 | 0.33 | 0.02 | 5 |
| 41 | 2 | 524 | 52 | 10 | 0.37 | 0.04 | 11 |
| 42 | 2 | 1102 | 61 | 6 | 0.82 | 0.05 | 6 |
| 43 | 2 | 544 | 66 | 12 | 0.39 | 0.05 | 13 |
| 44 | 2 | 865 | 63 | 7 | 0.63 | 0.05 | 8 |
| 45 | 2 | 1127 | 77 | 7 | 0.85 | 0.06 | 7 |
| 46 | 2 | 338 | 18 | 5 | 0.23 | 0.01 | 6 |
| 47 | 2 | 428 | 34 | 8 | 0.30 | 0.03 | 9 |
| 48 | 2 | 630 | 37 | 6 | 0.45 | 0.03 | 6 |
| 49 | 2 | 1447 | 3 | 0 | 1.12 | 0.00 | 0.1 |
| 50 | 2 | 328 | 35 | 11 | 0.22 | 0.03 | 12 |
| 51 | 1 | 223 | n/a | n/a | 0.14 | n/a | n/a |
| 52 | 2 | 586 | 81 | 14 | 0.42 | 0.06 | 15 |
| 53 | 2 | 328 | 42 | 13 | 0.22 | 0.03 | 14 |
| 54 | 2 | 795 | 66 | 8 | 0.58 | 0.05 | 9 |
| 55 | 2 | 403 | 21 | 5 | 0.28 | 0.02 | 6 |
| 56 | 2 | 234 | 4 | 2 | 0.15 | 0.00 | 2 |
| 57 | 2 | 615 | 59 | 10 | 0.44 | 0.04 | 10 |
| 58 | 2 | 531 | 7 | 1 | 0.38 | 0.01 | 1 |
| 59 | 2 | 432 | 21 | 5 | 0.30 | 0.02 | 5 |
| 60 | 2 | 1109 | 43 | 4 | 0.83 | 0.03 | 4 |

TABLE 14-continued

Concentration of SMN human CSF

| Sample | n | DE | DE SD | DE CV % | Calc [SMN] (pg/mL) | Calc [SMN] SD | Calc [SMN] CV % |
|---|---|---|---|---|---|---|---|
| 61 | 2 | 1232 | 44 | 4 | 0.93 | 0.04 | 4 |
| 62 | 2 | 571 | 52 | 9 | 0.40 | 0.04 | 10 |
| 63 | 2 | 544 | 35 | 6 | 0.39 | 0.03 | 7 |

As determined in the above examples, the assay parameters met specified thresholds. The LoD was well below the target of 0.1 pg/mL SMN protein (see Examples 2 and 6), the LLoQ and LLoRQ of 0.12 pg/mL (see Examples 3 and 4) was sufficient to detect endogenous SMN protein levels in human CSF (see Examples 5, 8, and 11). The average intra-assay precision of 3-9% CV and average inter-assay precision of 1-9% CV were well within the target limit of 20% CV (see Example 9). The percent recovery of spiked recombinant human SMN protein (see Examples 3, 4, 5, 7, and 8) and the % linearity of sample dilutions (see Example 8) were within 80-12% for at least 80% of samples tested.

Example 13

Single Administration Study of ISIS 396443

A single dose of ISIS 396443 was administered intrathecally as a lumbar puncture bolus injection using a spinal anesthesia needle between 21 gauge and 25 gauge. Before patients received a dose of ISIS 396443, a sample of CSF was taken and the amount of SMN protein present in the sample was measured and used as the baseline concentration of SMN protein in the CSF. Additionally, before patients received a dose of ISIS 396443, each patient was evaluated according to the Hammersmith Motor Function Scale-Expanded (HFMSE), and this HFMSE score was used as each patient's baseline HFMSE score.

Between 9 and 14 months after each patient received a dose of ISIS 396443, samples of CSF were taken and the amount of SMN protein present in the sample was measured. The amount of SMN protein measured between 9 and 14 months was then compared to the baseline concentration of SMN protein measured before therapy commenced and these values are presented in Table 15 below under the "% increase from baseline SMN protein" heading. The percentage amounts given under the "% increase from baseline SMN protein" heading indicate the percent increase in the amount of SMN protein compared to baseline. Additionally, between 9 and 14 months after each patient received a dose of ISIS 396443, each patient was evaluated according to the Hammersmith Motor Function Scale-Expanded (HFMSE). The average change in HFMSE for all patients in a patient group relative to the baseline HFMSE measurement is presented in Table 15 below under the "Change in HFMSE at 9-14 months" heading.

Table 15 below illustrates that an increase in the amount of SMN protein present in the CSF was associated with a clinical improvement in subjects, as measured by an increase in Hammersmith motor scores. For example, patients in group 3, who received a 6 mg dose of ISIS 396443 had an average change in HFMSE of +2.5 and an increase in SMN protein relative to the baseline. Similarly, patients in group 4, who received a 9 mg dose of ISIS 396443 had an average change in HFMSE of +5.75 and an even greater increase in SMN protein relative to the baseline compared to patients in the 1 mg, 3 mg, and 6 mg group.

TABLE 15

Single Administration Study of ISIS 396443

| Patient Group | # Patients | Dose (mg) | Change in HFMSE at 9-14 months | % increase from baseline SMN protein |
|---|---|---|---|---|
| 1 | 6 | 1 | −1.7 | 62% |
| 2 | 6 | 3 | +0.5 | 38% |
| 3 | 6 | 6 | +2.5 | 118% |
| 4 | 10 | 9 | +5.75 | 160% |

Example 14

Multiple Dose Administration Study of ISIS 396443

In a Phase 1/2a multiple dose study involving 25 patients having SMA, patient therapy was commenced. Before patients received a dose of ISIS 396443, a sample of CSF was taken and the amount of SMN protein present in the sample was measured and used as the baseline concentration of SMN protein in the CSF. Additionally, before patients received a dose of ISIS 396443, each patient was evaluated according to the Hammersmith Motor Function Scale-Expanded (HFMSE), and this HFMSE score was used as each patient's baseline HFMSE score.

ISIS 396443 was administered intrathecally as a lumbar puncture bolus injection using a spinal anesthesia needle between 21 gauge and 25 gauge. The dose amounts, number of patients receiving each dose, and dose frequency for multiple doses are listed in the table below. Patients having SMA and receiving a dose of 3 mg or 6 mg received a second dose approximately 29 days after the first dose and received a third dose approximately 85 days after receiving the first dose. Patients having SMA and receiving a dose of 9 mg received a second dose of ISIS 396443 approximately 85 days after receiving a first dose. In the table below "ND" stands for no dose. For example, SMA patients that receive a dose of 9 mg of ISIS 396443 on day 1 receive a second 9 mg dose of ISIS 396443 on day 85 and no dose of ISIS 396443 on day 29. Proposed dose frequency is approximate, for example, if the dose frequency is a dose at day 1 and a second dose at day 29, an SMA patient may receive a second dose 25, 26, 27, 28, 29, 30, 31, 32, 33, or 34 days after receipt of the first dose.

A sample of CSF was collected from each patient during each subsequent dose. For example, if a patient were to receive a dose of ISIS 396443 at day 1, day 29, and day 85, a sample of CSF for analysis would be collected from the patient at day 1, day 29, and day 85. Additionally, each patient was evaluated according to the Hammersmith Motor Function Scale-Expanded (HFMSE) at day 1, day 29, and day 85, and 9 months out from their first dose.

TABLE 16

Multiple Dose Administration Study of ISIS 396443

| Patient Group | # Patients | Dose at Day 1 (mg) | Dose at Day 29 (mg) | Dose at Day 85 (mg) |
|---|---|---|---|---|
| 1 | 8 | 3 | 3 | 3 |
| 2 | 8 | 6 | 6 | 6 |
| 3 | 9 | 9 | ND | 9 |

At 3 months after each patient received their first dose of ISIS 396443, samples of CSF were taken and the amount of SMN protein present in the sample was measured. The average % of SMN protein in the CSF relative to the baseline SMN protein in the CSF (measured before SMA patients received the first dose of ISIS 396443) was analyzed for all patients in each patient group. The average % increase of SMN protein in the CSF relative to the baseline SMN protein in the CSF is presented in Table 17 below under the "% increase from baseline SMN protein" heading. The percentage amounts given under the "% increase from baseline SMN protein" heading indicate the percent increase in the amount of SMN protein compared to baseline. Nine (9) months after each patient received a dose of ISIS 396443, each patient was evaluated according to the Hammersmith Motor Function Scale-Expanded (HFMSE). The average change in HFMSE for all patients in a patient group is presented in Table 17 below under the "Change in HFMSE at 9-14 months" heading. Table 15 below illustrates that an increase in the amount of SMN protein present in the CSF was associated with a clinical improvement in subjects, as measured by an increase in Hammersmith motor scores.

TABLE 17

Multiple Dose Administration Study of ISIS 396443

| Patient Group | # Patients | Dose (mg) | Change in HFMSE at 9 months | % increase from baseline SMN protein |
|---|---|---|---|---|
| 1 | 8 | 3 | +1.5 | 23% |
| 2 | 8 | 6 | +2.3 | 15% |
| 3 | 9 | 9 | +3.7 | 114% |

This example shows consistent dose-dependent and time-dependent improvements in a motor function outcome relevant for SMA and a correlated increase in the amount of SMN protein in the CSF.

What is claimed is:

1. A method of treating spinal muscular atrophy (SMA) in a human subject in need thereof, the method comprising administering to the human subject by intrathecal bolus injection doses of a pharmaceutical composition comprising a pharmaceutically acceptable carrier and an antisense oligonucleotide consisting of 18 linked nucleosides, wherein the antisense oligonucleotide has a nucleobase sequence consisting of the nucleobase sequence SEQ ID NO:1, wherein each internucleoside linkage of the antisense oligonucleotide is a phosphorothioate linkage, wherein each nucleoside of the antisense oligonucleotide is a 2'-MOE nucleoside, and wherein each cytosine of the antisense oligonucleotide is a 5-methyl cytosine, wherein the doses comprise:

(i) a first dose of 12 mg of the antisense oligonucleotide;
(ii) a second dose of 12 mg of the antisense oligonucleotide administered approximately 12-18 days after administration of the first dose;
(iii) a third dose of 12 mg of the antisense oligonucleotide administered approximately 25-35 days after administration of the first dose, wherein the third dose is administered at least 14 days after the second dose;
(iv) a fourth dose of 12 mg of the antisense oligonucleotide administered approximately 60-70 days after administration of the first dose;
(v) a fifth dose of 12 mg of the antisense oligonucleotide administered approximately 178-188 days after administration of the first dose; and
(vi) a sixth dose of 12 mg of the antisense oligonucleotide administered approximately 298-308 days after administration of the first dose.

2. The method of claim 1, wherein the administration to the human subject comprises:

(i) the first dose of the antisense oligonucleotide;
(ii) the second dose of the antisense oligonucleotide administered approximately 12 days after administration of the first dose;

(iii) the third dose of the antisense oligonucleotide administered approximately 25 days after administration of the first dose;

(iv) the fourth dose of the antisense oligonucleotide administered approximately 60 days after administration of the first dose;

(v) the fifth dose of the antisense oligonucleotide administered approximately 178 days after administration of the first dose; and (vi) the sixth dose of the antisense oligonucleotide administered approximately 298 days after administration of the first dose.

3. A method of treating SMA in a human subject in need thereof, the method comprising administering to the human subject by intrathecal bolus injection doses of a pharmaceutical composition comprising a pharmaceutically acceptable carrier and an antisense oligonucleotide consisting of 18 linked nucleosides, wherein the antisense oligonucleotide has a nucleobase sequence consisting of the nucleobase sequence SEQ ID NO:1, wherein each internucleoside linkage of the antisense oligonucleotide is a phosphorothioate linkage, wherein each nucleoside of the antisense oligonucleotide is a 2'-MOE nucleoside, and wherein each cytosine of the antisense oligonucleotide is a 5-methyl cytosine, wherein the doses comprise:

(i) a first dose of 12 mg of the antisense oligonucleotide;

(ii) a second dose of 12 mg of the antisense oligonucleotide administered approximately 15 days after administration of the first dose;

(iii) a third dose of 12 mg of the antisense oligonucleotide administered approximately 29 days after administration of the first dose;

(iv) an additional dose of 12 mg of the antisense oligonucleotide administered approximately 183 days after administration of the first dose; and (v) an additional dose of 12 mg of the antisense oligonucleotide administered approximately 302 days after administration of the first dose.

4. The method of claim 3, wherein the human subject is further administered an additional dose of 12 mg of the antisense oligonucleotide approximately 64 days after administration of the first dose.

5. The method of claim 3, wherein the human subject is administered the antisense oligonucleotide using a spinal anesthesia needle.

6. The method of claim 3, wherein the antisense oligonucleotide is administered at a concentration of 2.4 mg/mL.

7. The method of claim 6, wherein the antisense oligonucleotide is administered in an injection volume of 5.0 mL.

8. The method of claim 7, wherein the human subject has (i) type I SMA; (ii) type II SMA; (iii) type III SMA; or (iv) type IV SMA.

9. The method of claim 7, wherein the human subject is administered the first dose of the antisense oligonucleotide when the human subject is less than one week old.

10. The method of claim 7, wherein the human subject is administered the first dose of the antisense oligonucleotide when the human subject is less than one month old.

11. The method of claim 7, wherein the human subject is administered the first dose of the antisense oligonucleotide when the human subject is less than 3 months old.

12. The method of claim 7, wherein the human subject is administered the first dose of the antisense oligonucleotide when the human subject is less than 6 months old.

13. The method of claim 7, wherein the human subject is administered the first dose of the antisense oligonucleotide when the human subject is less than 1 year old.

14. The method of claim 7, wherein the human subject is administered the first dose of the antisense oligonucleotide when the human subject is less than 2 years old.

15. The method of claim 7, wherein the human subject is administered the first dose of the antisense oligonucleotide when the human subject is less than 15 years old.

16. The method of claim 7, wherein the human subject is administered the first dose of the antisense oligonucleotide when the human subject is older than 15 years old.

17. The method of claim 3, wherein the human subject is a human subject having one or more symptoms associated with spinal muscular atrophy.

* * * * *